US007041295B2

(12) United States Patent
Delcayre

(10) Patent No.: US 7,041,295 B2
(45) Date of Patent: *May 9, 2006

(54) COMPOUNDS FOR TREATMENT OF INFECTIOUS AND IMMUNE SYSTEM DISORDERS AND METHODS FOR THEIR USE

(75) Inventor: Alain Delcayre, San Jose, CA (US)

(73) Assignee: Genesis Research & Development Corporation LTD, Auckland (NZ)

( * ) Notice: Subject to any disclaimer, the term of this patent is extended or adjusted under 35 U.S.C. 154(b) by 568 days.

This patent is subject to a terminal disclaimer.

(21) Appl. No.: 10/100,679

(22) Filed: Mar. 14, 2002

(65) Prior Publication Data

US 2003/0054013 A1 Mar. 20, 2003

Related U.S. Application Data

(63) Continuation-in-part of application No. 09/450,072, filed on Nov. 29, 1999, now Pat. No. 6,358,734, which is a continuation-in-part of application No. 09/351,348, filed on Jul. 12, 1999, now Pat. No. 6,436,898.

(51) Int. Cl.

*A01N 37/18* (2006.01)
*A61K 38/00* (2006.01)
*A61K 39/00* (2006.01)
*C07K 16/00* (2006.01)
*A61B 5/055* (2006.01)

(52) U.S. Cl. ................ 424/184.1; 530/300; 530/388.4; 424/9.34; 424/190.1; 514/2

(58) Field of Classification Search .................... 514/2; 530/300, 388.4, 350; 424/9.34, 184.1, 190.1
See application file for complete search history.

(56) References Cited

U.S. PATENT DOCUMENTS

| | | | |
|---|---|---|---|
| 6,410,720 B1 * | 6/2002 | Tan et al. | 536/23.7 |
| 6,436,898 B1 * | 8/2002 | Delcayre | 514/2 |
| 2004/0072224 A1 * | 4/2004 | Delcayre | 435/6 |

OTHER PUBLICATIONS

Bowie et al. Science Mar. 1990; 247:1306-10.*
Rudinger. Peptide Hormones 1976; Jun.:pp. 1-7.*
Strugnell et al. Immunl Cell Biol 1997;75:364-69.*
Encyclopedia Britannica online.*
JFT Griffin, Clinical Infectious Diseases, "Veterinary Tuberculosis Vaccine Development," Jun. 2000, 30(suppl) ;S223-8.*
MJ McCluskie et al., Molecular Medicine , "Route and Method od Delivery of DNA VaccineInfluence Immune Responses in Mice and Non-Human Primates," May 1999, vol. 5, pp. 287-300.*
PEM Fine, Genetics and tuberculosis, "Vaccines, genes and trials," 1998, 217, pp. 57-72.*
Swiss-Prot Accession No. P91408; Geisel C. et al., submitted Dec. 15, 1998.
PIR Accession No. T46707; Ilg, T. et al., submitted Feb. 18, 2000.
PIR Accession No. T28682; Parkhill, J. et al., submitted Oct. 15, 1999.
TREMBL Accession No. Q9S9B2; Raghavan, V. et al., submitted May 1, 2000.
Swiss-Prot Accession No. P06530; Kiss, A. et al., submitted Jan. 1, 1988.
Swiss-Prot Accession No. Q06965; Neidle, E.L. et al., submitted Oct. 1, 1996.
TREMBL Accession No. E968234; LeGoux, R. et al., submitted Nov. 1, 1998.
TREMBL Accession No. E1263321; Van, L.F. et al., submitted Nov. 1, 1998.
GenPept Accession No. CAB45489; James, K.D. et al., submitted Jun. 18, 1999.
GenPept Accession No. CAB07541; Dziadek, J. et al., submitted Mar. 19, 1997.
GenPept Accession No. BAA97474; Nakamura, Y., submitted Apr. 2, 1999.
Swiss-Prot Accession No. P41014; Ishizuka, M., submitted Aug. 1994.

(Continued)

*Primary Examiner*—Dave Trong Nguyen
*Assistant Examiner*—Maria Marvich
(74) *Attorney, Agent, or Firm*—Janet Sleath; Speckman Law Group PLLC

(57) ABSTRACT

The present invention provides polypeptides comprising an immunogenic epitope of a *M. vaccae* protein, polynucleotides encoding such polypeptides, and fusion proteins comprising at least one such polypeptide, together with genetic constructs comprising at least one inventive polynucleotide. Compositions comprising such polypeptides, polynucleotides, fusion proteins and/or genetic constructs may be employed in the treatment of infectious diseases and immune disorders.

5 Claims, 11 Drawing Sheets

OTHER PUBLICATIONS

GenPept Accession No. AAF10382; White, O. et al., submitted Nov. 8, 1999.

GenPept Accession No. AAD34368; Janoir, C., et al., submitted Feb. 22, 1999.

GenPept Accession No. AAC70256; Kuzio, J. et al., submitted Aug. 3, 1998.

GenPept Accession No. AAA72555; Tokunaga, T. et al., submitted 1985.

GenPept Accession No. AAB38132; Shago, M. et al., submitted Feb. 29, 1996.

GenPept Accession No. AAC32046; Zhu, W.M. et al., submitted Nov. 11, 1997.

* cited by examiner

Induction of protective immunity by ME/D vaccination

Proliferative responses by lymph node cells from mouse immunized subcutaneously with recombinant multi-epitope constructs IFN-γ production by lymph node cells from mice immunized subcutaneously with recombinant multi-epitope constructs Proliferative responses in mice immunized with ME/D by different routes Contribution of single epitopes to proliferative responses in mice immunized with ME/D by different routes Contribution of single epitopes to IFN-γ production in mice immunized with ME/D by different routes Titre and subclass of anti-ME antibody in the serum of mice immunized with ME DNA IFN-γ production by memory splenocytes of BALB/cByJ mice IFN-γ production and proliferative responses of human PBMC after *in vitro* stimulation with rME/A, rME/B and rME/D IFN-γ and proliferative responses of human PBMC after *in vitro* stimulation with recombinant single epitopes

COMPOUNDS FOR TREATMENT OF INFECTIOUS AND IMMUNE SYSTEM DISORDERS AND METHODS FOR THEIR USE

CROSS REFERENCE TO RELATED APPLICATIONS

This application is a continuation-in-part of U.S. patent application Ser. No. 09/450,072 filed Nov. 29, 1999, now U.S. Pat. No. 6,358,734, which is a continuation-in-part of U.S. patent application Ser. No. 09/351,348 filed Jul. 12, 1999, and claims priority to PCT International Patent Application PCT/NZ00/00121 filed Jul. 10, 2000.

TECHNICAL FIELD

The present invention relates generally to the detection, treatment and prevention of infectious diseases. In particular, the invention is related to compounds comprising immunogenic epitopes isolated from *Mycobacterium vaccae*, and the use of such compounds in vaccination or immunotherapy against infectious disease, including mycobacterial infections such as infection with *Mycobacterium tuberculosis* or *Mycobacterium avium*, and in certain treatments for immune disorders and cancer.

BACKGROUND OF THE INVENTION

The present invention relates generally to the treatment and prevention of infectious diseases, and to the treatment of certain immune disorders and cancers. In particular, the invention is related to compounds and methods for the treatment and prevention of mycobacterial infections, including infection with *Mycobacterium tuberculosis* or *Mycobacterium avium*.

Tuberculosis is a chronic, infectious disease that is caused by infection with *Mycobacterium tuberculosis* (*M. tuberculosis*). It is a major disease in developing countries, as well as an increasing problem in developed areas of the world, with about 8 million new cases and 3 million deaths each year. Although the infection may be asymptomatic for a considerable period of time, the disease is most commonly manifested as a chronic inflammation of the lungs, resulting in fever and respiratory symptoms. If left untreated, significant morbidity and death may result.

Although tuberculosis can generally be controlled using extended antibiotic therapy, such treatment is not sufficient to prevent the spread of the disease. Infected individuals may be asymptomatic, but contagious, for some time. In addition, although compliance with the treatment regimen is critical, patient behaviour is difficult to monitor. Some patients do not complete the course of treatment, which can lead to ineffective treatment and the development of drug resistant mycobacteria.

Inhibiting the spread of tuberculosis requires effective vaccination and accurate, early diagnosis of the disease. Currently, vaccination with live bacteria is the most efficient method for inducing protective immunity. The most common *mycobacterium* employed for this purpose is *Bacillus* Calmette-Guerin (BCG), an avirulent strain of *Mycobacterium bovis*. However, the safety and efficacy of BCG is a source of controversy and some countries, such as the United States of America, do not vaccinate the general public. Diagnosis of *M. tuberculosis* infection is commonly achieved using a skin test, which involves intradermal exposure to tuberculin PPD (protein-purified derivative). Antigen-specific T cell responses result in measurable induration at the injection site by 48–72 hours after injection, thereby indicating exposure to mycobacterial antigens. Sensitivity and specificity have, however, been a problem with this test, and individuals vaccinated with BCG cannot be distinguished from infected individuals.

A less well-known mycobacterium that has been used for immunotherapy for tuberculosis, and also leprosy, is *Mycobacterium vaccae*, which is non-pathogenic in humans. However, there is less information on the efficacy of *M. vaccae* compared with BCG, and it has not been used widely to vaccinate the general public. *M. bovis* BCG and *M. vaccae* are believed to contain antigenic compounds that are recognised by the immune system of individuals exposed to infection with *M. tuberculosis*.

Several patents and other publications disclose treatment of various conditions by administering mycobacteria, including *M. vaccae*, or certain mycobacterial fractions. International Patent Publication WO 91/02542 discloses treatment of chronic inflammatory disorders in which a patient demonstrates an abnormally high release of IL-6 and/or TNF or in which the patient's IgG shows an abnormally high proportion of agalactosyl IgG. Among the disorders mentioned in this publication are psoriasis, rheumatoid arthritis, mycobacterial disease, Crohn's disease, primary biliary cirrhosis, sarcoidosis, ulcerative colitis, systemic lupus erythematosus, multiple sclerosis, Guillain-Barre syndrome, primary diabetes mellitus, and some aspects of graft rejection. The therapeutic agent preferably comprises autoclaved *M. vaccae* administered by injection in a single dose.

U.S. Pat. No. 4,716,038 discloses diagnosis of, vaccination against and treatment of autoimmune diseases of various types, including arthritic diseases, by administering mycobacteria, including *M. vaccae*. U.S. Pat. No. 4,724,144 discloses an immunotherapeutic agent comprising antigenic material derived from *M. vaccae* for treatment of mycobacterial diseases, especially tuberculosis and leprosy, and as an adjuvant to chemotherapy. International Patent Publication WO 91/01751 discloses the use of antigenic and/or immunoregulatory material from *M. vaccae* as an immunoprophylactic to delay and/or prevent the onset of AIDS. International Patent Publication WO 94/06466 discloses the use of antigenic and/or immunoregulatory material derived from *M. vaccae* for therapy of HIV infection, with or without AIDS and with or without associated tuberculosis.

Traditional vaccines contain the disease-causing organism (or a component thereof) in either attenuated or killed form. As an alternative approach to traditional vaccines, DNA vaccines have been developed for diseases as diverse as AIDS, influenza, cancer and malaria. Clinical trials of DNA vaccines are in progress for a number of these diseases. A typical DNA vaccine consists of DNA encoding an antigen cloned in a non-active plasmid carrier. Expression of the antigen encoded by the vaccine DNA is usually under control of a strong promoter, such as human β-actin, Rous sarcoma virus (RSV) or CMV promoter (Ramsay A J, et al. *Immunology and Cell Biology* 75:360–363, 1997). The first experimental evidence that DNA vaccines were able to induce the desired immune response was produced by Tang et al. (Tang D-C, et al. *Nature* 356:152–154, 1992). In these experiments, mice inoculated with plasmids containing the gene encoding for human growth hormone developed specific primary antibody responses.

Immune responses to two DNA vaccines containing genes from *M. tuberculosis* have been evaluated in animal models. The first vaccine contained the gene coding for the GroEL stress protein (65 kDa protein; Tascon R E, et al. *Nature Med.* 2:888–892, 1996). Mice injected with this DNA vaccine were protected at a level equivalent to mice receiving the traditional BCG vaccine. The second DNA vaccine against *M. tuberculosis* contained DNA encoding an antigen from the antigen 85 complex and similar results to the study by Tang et al. were obtained (Huygen K, et al. *Nature Med.* 2:893–898, 1996). U.S. Pat. No. 5,736,524 discloses vaccination of domestic mammals or livestock against infection by *M. tuberculosis* or *M. bovis* by administering a polynucleotide tuberculosis vaccine comprising the *M. tuberculosis* antigen 85 gene operably linked to transcription regulatory elements.

The first human DNA vaccine trial was reported recently (Wang R, et al. Science 282:476–80, 1998). In this trial, an antigen from *Plasmodium falciparum*, the causative agent of malaria, was injected into healthy volunteers. The desired immune response was elicited, as demonstrated by the presence of cytotoxic T ($CD8^+$) lymphocytes (CTL), suggesting that the immune system would be able to clear parasites from infected patients. Safety and immunogenicity of a human DNA vaccine against HIV-1 infection was determined in a trial performed by McGregor et al. (*J. Infect. Dis.* 178:92–100, 1998). Experimental data from other DNA vaccine experiments has also suggested that antibodies, MHC class 1-restricted $CD8^+$ CTL and class II-restricted $CD4^+$ helper T cells are produced following injection with DNA vaccines (Ramsay, A J et al. *Immunology and Cell Biology* 75:360–363, 1997).

DNA vaccines have distinct advantages over more traditional vaccines containing killed or attenuated organisms. DNA vaccination induces immune responses that are long-lived and therefore only a single inoculation may be required. DNA encoding a number of antigens may be incorporated into a single plasmid thereby providing protection against a number of diseases. The technology for DNA vaccine production is relatively simple and the same technology can be used to produce all vaccines, with a resulting cheaper production cost. Delivery of efficacious traditional vaccines to the patient are dependent on maintaining an unbroken “cold chain” from manufacturer to clinic. DNA vaccines produced in solution or in dried form are not sensitive to storage conditions.

Recently, alternative ways of constructing and applying DNA vaccines have been developed. In one of the techniques, called Somatic Transgene Immunization (STI), the plasmid DNA carrying an immunoglobulin heavy chain gene under the control of tissue-specific regulatory elements was inoculated directly into the spleen of mice, with subsequent expression of the antigen on the surface of B-cells (Xiong S, et al. *Proc. Natl. Acad. Sci. USA* 94:6352–6357, 1997). These B cells produced antibodies against the expressed antigen, leading to an immune response. Subsequent studies showed that STI induced persistent immunologic memory for up to 2 years (Gerloni M, et al. *Vaccine* (2–3):293–297, 1998).

Expression Library Immunization (ELI) is another technique employing DNA vaccines (Barry M A, et al. *Nature* 377:632–635, 1995). In this technique, fragments of the complete genome of a pathogen are cloned into a vector and used as vaccine. Selection of protective antigen(s), particularly those inducing CTL, is done by screening and rescreening pools of clones until single clones can be identified. The polynucleotide or polypeptide identified may then be incorporated into a proven delivery system.

Progress on the development of an epitope-based vaccine for the treatment and prevention of HIV infection by scientists at Epimmune Inc. (San Diego, Calif.), has recently been published (Ishioka G Y, et al., *Journal of Immunology* 162:3915–3925, 1999).

There remains a need in the art for effective compounds and methods for preventing and treating infectious disorders, such as tuberculosis and other mycobacterial infections in humans and in domestic mammals or livestock, and for the treatment of certain immune system-related disorders.

SUMMARY OF THE INVENTION

Briefly stated, the present invention provides compounds and methods for the prevention and treatment of infectious diseases, such as mycobacterial infections, and for the treatment of immune disorders and cancers.

In a first aspect, isolated polynucleotides are provided that are derived from the *M. vaccae* genome. These polynucleotides encode polypeptide epitopes selected on the basis of their immunogenic properties as illustrated by results from a number of immunological assays. In specific embodiments, the inventive polynucleotides comprise a sequence selected from the group consisting of: (a) sequences provided in SEQ ID NO: 8–21; (b) sequences having at least 75%, 90% or 95% identical residues to a sequence of SEQ ID NO: 8–21 as determined using the computer algorithm BLASTN; and (c) complements of the sequences of (a) and (b).

In a second aspect, the invention provides isolated polypeptides comprising an immunogenic epitope of a *M. vaccae* antigen. In specific embodiments, the inventive polypeptides comprise a sequence selected from the group consisting of: (a) sequences provided in SEQ ID NO: 64–77; and (b) sequences having at least 75%, 90% or 95% identical residues to a sequence of SEQ ID NO: 64–77 as determined using the computer algorithm FASTX.

Genetic constructs comprising at least one of the inventive polynucleotides, and host cells transformed or transfected with such genetic constructs are also provided.

In another aspect, the present invention provides fusion proteins comprising at least one polypeptide of the present invention. In specific embodiments, such fusion proteins comprise a sequence of SEQ ID NO: 79–81 or 90–97. Polynucleotides encoding such fusion proteins are also provided. In certain embodiments, such polynucleotides comprise a sequence of SEQ ID NO: 56–58 or 82–89.

Within other aspects, the present invention provides compositions that comprise at least one of the inventive polypeptides, polynucleotides, fusion proteins or genetic constructs, and a physiologically acceptable carrier. The invention also provides compositions comprising at least one of the above polypeptides, polynucleotides, fusion proteins or genetic constructs and an immunostimulant.

In yet another aspect, methods are provided for enhancing an immune response in a patient, comprising administering to a patient an effective amount of one or more of the above compositions. In one embodiment, the immune response is a Th1 response.

In further aspects of this invention, methods are provided for the treatment of a disorder in a patient, comprising administering to the patient a composition of the present invention. In certain embodiments, the disorder is selected from the group consisting of immune disorders, infectious diseases and cancer.

These and other aspects of the present invention will become apparent upon reference to the following detailed description. All references disclosed herein are hereby incorporated by reference in their entirety as if each was incorporated individually.

DETAILED DESCRIPTION OF THE INVENTION

Figure 1:
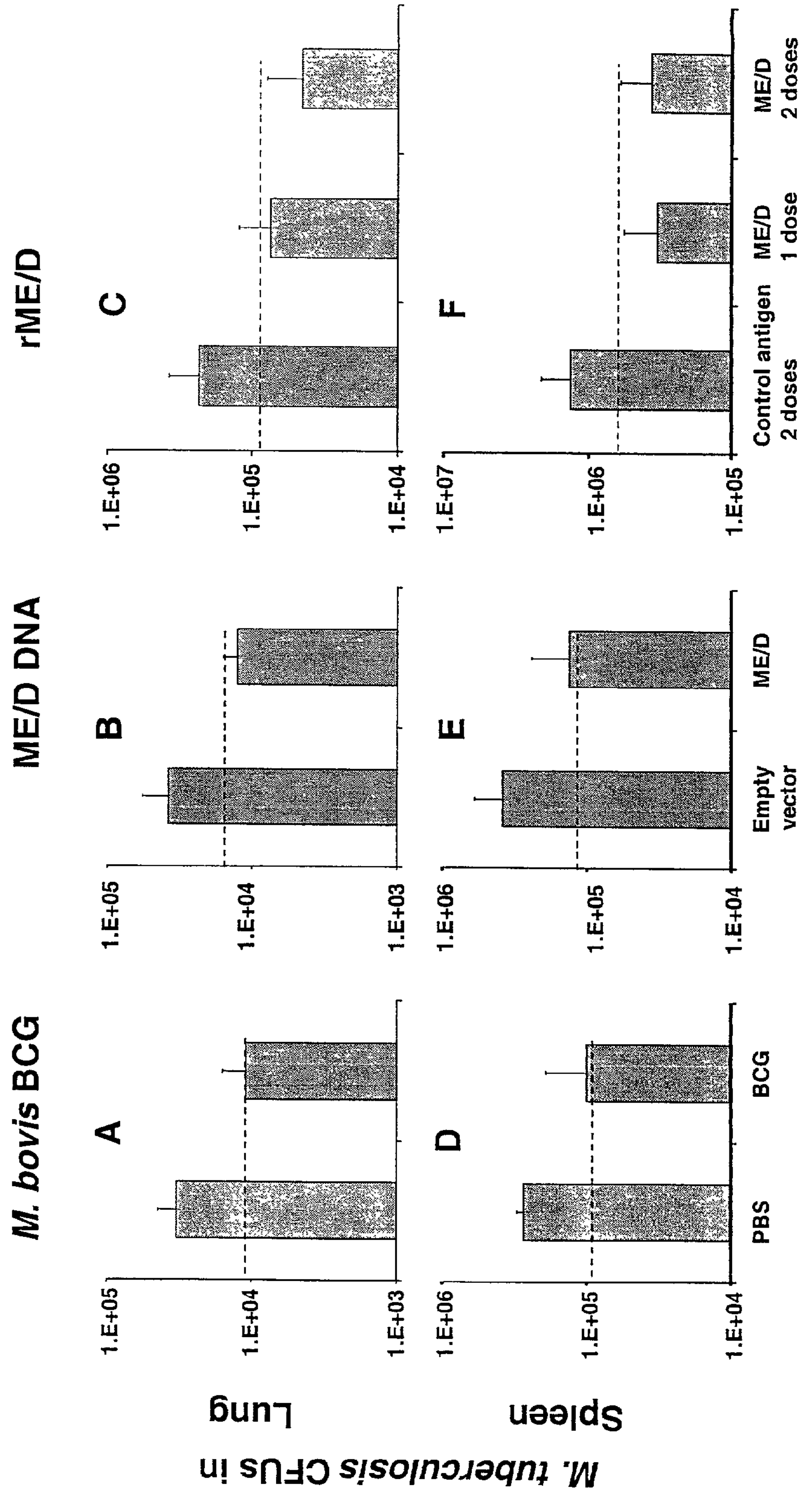
FIGS. 1A–F illustrate the induction of protective immunity, measured as a decrease in *M. tuberculosis* CFU in lung and spleen homogenates of BALB/cByJ mice, by vaccination with *M. bovis* BCG (FIGS. 1A and D, respectively), with ME/D DNA (FIGS. 1B and E, respectively), or with rME/D (FIGS. 1C and F, respectively).

As noted above, the present invention is generally directed to compositions and methods for preventing and treating disorders including infectious diseases and certain immune disorders and cancers. Examples of such disorders include, but are not limited to, mycobacterial infections, including *M. tuberculosis* and *M. avium* infections, and disorders in which the stimulation of a Th1 immune response is beneficial, including (but not limited to) psoriasis and allergic rhinitis.

Certain pathogens, such as *M. tuberculosis*, as well as certain cancers, are effectively contained by an immune attack directed by $CD4^+$ T cells, known as cell-mediated immunity. Other pathogens, such as poliovirus, also require antibodies, produced by B cells, for containment. These different classes of immune attack (T cell or B cell) are controlled by different subpopulations of $CD4^+$ T cells, commonly referred to as Th1 and Th2 cells.

The two types of Th cell subsets have been well characterized in a murine model and are defined by the cytokines they release upon activation. The Th1 subset secretes IL-2, IFN-γ and tumor necrosis factor, and mediates macrophage activation and delayed-type hypersensitivity response. The Th2 subset releases IL-4, IL-5, IL-6 and IL-10, which stimulate B cell activation. The Th1 and Th2 subsets are mutually inhibiting, so that IL-4 inhibits Th1-type responses, and IFN-γ inhibits Th2-type responses. Similar Th1 and Th2 subsets have been found in humans, with release of the identical cytokines observed in the murine model. Amplification of Th1-type immune responses is central to a reversal of disease state in many disorders, including disorders of the respiratory system such as tuberculosis, sarcoidosis, asthma, allergic rhinitis and lung cancers.

In one aspect, the compositions of the present invention include polypeptides that comprise at least one immunogenic epitope of a *M. vaccae* antigen, or a variant thereof. In specific embodiments, the inventive polypeptides comprise a sequence provided in SEQ ID NO: 61–77. Such polypeptides stimulate T cell proliferation, and/or interferon gamma secretion from T cells of individuals exposed to *M. tuberculosis.*

As used herein, the term "polypeptide" encompasses amino acid chains of any length, including full-length proteins (i.e., antigens), wherein the amino acid residues are linked by covalent peptide bonds. Thus, a polypeptide comprising an immunogenic epitope of one of the above antigens may consist entirely of the immunogenic epitope, or may contain additional sequences. The additional sequences may be derived from the native *M. vaccae* antigen or may be heterologous, and such sequences may (but need not) be immunogenic.

"Immunogenic," as used herein, refers to the ability to elicit an immune response in a patient, such as a human, or in a biological sample. In particular, an immunogenic epitope is that portion of a polypeptide that is capable of stimulating cell proliferation, interleukin-12 production or interferon-γ production in biological samples comprising one or more cells selected from the group of T cells, NK cells, B cells and macrophages, where the cells are derived from a mycobacteria-immune individual. In general, an immunogenic epitope will stimulate proliferation of PBMC from mycobacteria-immune individuals at levels at least two-fold greater than that observed in control PBMC, determined using assay techniques detailed below in Example 1. Alternatively, or additionally, an immunogenic epitope will stimulate the production of interferon-γ in PBMC from mycobacteria-immune individuals at levels that are at least two-fold greater than those observed in control cells as determined by at least a two-fold increase in OD in an ELISA assay as detailed in Example 1. A mycobacteria-immune individual is one who is considered to be resistant to the development of mycobacterial infection by virtue of having mounted an effective T cell response to *M. tuberculosis*, to environmental saprophytes, or to BCG. Such individuals may be identified based on a strongly positive (i.e., greater than about 10 mm diameter induration) intradermal skin test response to tuberculosis proteins (PPD), and an absence of any symptoms of tuberculosis infection. Polypeptides comprising at least an immunogenic epitope of one or more *M. vaccae* antigens may generally be used to induce protective immunity against tuberculosis in a patient and/or to stimulate an immune response in a patient.

In another aspect, the compositions of the present invention comprise isolated polynucleotides that encode polypeptides and/or fusion proteins comprising an immunogenic epitope of a *M. vaccae* antigen. In specific embodiments, the inventive polynucleotides comprise a sequence of SEQ ID NO: 8–21, 56–58 and 82–89. Complements of the inventive isolated polynucleotides, reverse complements of such isolated polynucleotides and reverse sequences of such isolated polynucleotides are also provided, together with variants of such sequences. The present invention also encompasses polynucleotide sequences that differ from the disclosed sequences but which, due to the degeneracy of the genetic code, encode a polypeptide which is the same as that encoded by a polynucleotide sequence disclosed herein.

The term "polynucleotide(s)," as used herein, means a single or double-stranded polymer of deoxyribonucleotide or ribonucleotide bases and includes DNA and corresponding RNA molecules, including HnRNA and mRNA molecules, both sense and anti-sense strands, and comprehends cDNA, genomic DNA and recombinant DNA, as well as wholly or partially synthesized polynucleotides. An HnRNA molecule contains introns and corresponds to a DNA molecule in a generally one-to-one manner. An mRNA molecule corresponds to an HnRNA and/or DNA molecule from which the introns have been excised. A polynucleotide may consist of an entire gene, or any portion thereof. Operable anti-sense polynucleotides may comprise a fragment of the corresponding polynucleotide, and the definition of "polynucleotide" therefore includes all such operable anti-sense fragments. Anti-sense polynucleotides and techniques involving anti-sense polynucleotides are well known in the art and are described, for example, in Robinson-Benion et al. "Antisense techniques," *Methods in Enzymol.* 254:363–375, 1995; and Kawasaki et al. *Artific. Organs* 20:836–848, 1996.

The definition of the terms "complement", "reverse complement" and "reverse sequence", as used herein, is best illustrated by the following example. For the sequence 5' AGGACC 3', the complement, reverse complement and reverse sequence are as follows:

```
complement            3' TCCTGG 5'
reverse complement    3' GGTCCT 5'
reverse sequence      5' CCAGGA 3'.
```

Preferably, sequences that are complements of a specifically recited polynucleotide sequence are complementary over the entire length of the specific polynucleotide sequence.

All the polynucleotides and polypeptides provided by the present invention are isolated and purified, as those terms are commonly used in the art. Preferably, the inventive polypeptides and polynucleotides are at least about 80% pure, more preferably at least about 90% pure, and most preferably at least about 99% pure.

The compositions and methods of this invention also encompass variants of the above polypeptides and polynucleotides. Variants may be naturally occurring allelic variants, or non-naturally occurring variants. As used herein, the term "variant" comprehends nucleotide or amino acid sequences different from the specifically identified sequences, wherein one or more nucleotides or amino acid residues is deleted, substituted, or added. Variants may be naturally occurring allelic variants, or non-naturally occurring variants. Variant sequences (polynucleotide or polypeptide) preferably exhibit at least 50%, more preferably at least 75%, more preferably yet at least 90%, and most preferably at least 95% identity to a sequence of the present invention. The percentage identity is determined by aligning the two sequences to be compared as described below, determining the number of identical residues in the aligned portion, dividing that number by the total number of residues in the inventive (queried) sequence, and multiplying the result by 100. By way of example only, assume a queried polynucleotide having 220 nucleic acids has a hit to a polynucleotide sequence in the EMBL database having 520 nucleic acids over a stretch of 23 nucleotides in the alignment produced by the BLASTN algorithm using the default parameters as described below. The 23 nucleotide hit includes 21 identical nucleotides, one gap and one different nucleotide. The percentage identity of the queried polynucleotide to the hit in the EMBL database is thus 21/220 times 100, or 9.5%. The percentage identity of polypeptide sequences may be determined in a similar fashion.

Polynucleotide and polypeptide sequences may be aligned, and percentages of identical residues in a specified region may be determined against another polynucleotide or polypeptide sequence, using computer algorithms that are publicly available. Two exemplary algorithms for aligning and identifying the similarity of polynucleotide sequences are the BLASTN and FASTA algorithms. Polynucleotides may also be analyzed using the BLASTX algorithm, which compares the six-frame conceptual translation products of a nucleotide query sequence (both strands) against a protein sequence database. The percentage identity of polypeptide sequences may be examined using the BLASTP algorithm. The BLASTN, BLASTP and BLASTX algorithms are available on the NCBI anonymous FTP server under /blast/ executables/ and are available from the National Center for Biotechnology Information (NCBI), National Library of Medicine, Building 38A, Room 8N805, Bethesda, Md. 20894, USA. The BLASTN algorithm Version 2.0.11 [Jan. 20, 2000], set to the parameters described below, is preferred for use in the determination of polynucleotide variants according to the present invention. The BLASTP algorithm, set to the parameters described below, is preferred for use in the determination of polypeptide variants according to the present invention. The use of the BLAST family of algorithms, including BLASTN, BLASTP and BLASTX, is described in the publication of Altschul, et al., *Nucleic Acids Res.* 25: 3389–3402, 1997.

The FASTA and FASTX algorithms are available on the Internet, and from the University of Virginia by contacting the Vice Provost for Research, University of Virginia, P.O. Box 9025, Charlottesville, Va. 22906–9025, USA. The FASTA algorithm, set to the default parameters described in the documentation and distributed with the algorithm, may be used in the determination of polynucleotide variants. The readme files for FASTA and FASTX Version 1.0x that are distributed with the algorithms describe the use of the algorithms and describe the default parameters. The use of the FASTA and FASTX algorithms is described in Pearson and Lipman, *Proc. Natl. Acad. Sci. USA* 85:2444–2448, 1988; and Pearson, *Methods in Enzymol.* 183:63–98, 1990.

The following running parameters are preferred for determination of alignments and similarities using BLASTN that contribute to the E values and percentage identity for polynucleotides: Unix running command with the following default parameters: blastall -p blastn -d embldb -e 10 -G O-E O -r 1 -v 30 -b 30 -i queryseq results; and parameters are: -p Program Name [String]; -d Database [String]; -e Expectation value (E) [Real]; -G Cost to open a gap (zero invokes default behavior) [Integer]; -E Cost to extend a gap (zero invokes default behavior) [Integer]; -r Reward for a nucleotide match (blastn only) [Integer]; -v Number of one-line descriptions (V) [Integer]; -b Number of alignments to show (B) [Integer]; -i Query File [File In]; -o BLAST report Output File [File Out] Optional.

The following running parameters are preferred for determination of alignments and similarities using BLASTP that contribute to the E values and percentage identity of polypeptide sequences: blastall -p blastp -d swissprotdb -e 10 -G O-E O -v 30 -b 30 -i queryseq -o results; the parameters are: -p Program Name [String]; -d Database [String]; -e Expectation value (E) [Real]; -G Cost to open a gap (zero invokes default behavior) [Integer]; -E Cost to extend a gap (zero invokes default behavior) [Integer]; -v Number of one-line descriptions (v) [Integer]; -b Number of alignments to show (b) [Integer]; -I Query File [File In]; -o BLAST report Output File [File Out] Optional.

The “hits” to one or more database sequences by a queried sequence produced by BLASTN, BLASTP, FASTA, or a similar algorithm, align and identify similar portions of sequences. The hits are arranged in order of the degree of similarity and the length of sequence overlap. Hits to a database sequence generally represent an overlap over only a fraction of the sequence length of the queried sequence. The BLASTN, FASTA and BLASTP algorithms also produce “Expect” values for polynucleotide and polypeptide alignments. The Expect value (E) indicates the number of hits one can “expect” to see over a certain number of contiguous sequences by chance when searching a database of a certain size. The Expect value is used as a significance threshold for determining whether the hit to a database indicates true similarity. For example, an E value of 0.1 assigned to a polynucleotide hit is interpreted as meaning that in a database of the size of the EMBL database, one might expect to see 0.1 matches over the aligned portion of the sequence with a similar score simply by chance. By this criterion, the aligned and matched portions of the sequences then have a probability of 90% of being related. For sequences having an E value of 0.01 or less over aligned and matched portions, the probability of finding a match by chance in the EMBL database is 1% or less using the BLASTN algorithm. E values for polypeptide sequences may be determined in a similar fashion using various polypeptide databases, such as the SwissProt database.

According to one embodiment, “variant” polynucleotides and polypeptides, with reference to each of the polynucleotides and polypeptides of the present invention, preferably comprise sequences having the same number or fewer nucleic or amino acids than each of the polynucleotides or polypeptides of the present invention and producing an E value of 0.01 or less when compared to the polynucleotide or polypeptide of the present invention. That is, a variant polynucleotide or polypeptide is any sequence that has at least a 99% probability of being the same as the polynucleotide or polypeptide of the present invention, measured as having an E value of 0.01 or less using the BLASTN, FASTA or BLASTP algorithms set at the default parameters. According to a preferred embodiment, a variant polynucleotide is a sequence having the same number or fewer nucleic acids than a polynucleotide of the present invention that has at least a 99% probability of being the same as the polynucleotide of the present invention, measured as having an E value of 0.01 or less using the BLASTN algorithm set at the default parameters. Similarly, according to a preferred embodiment, a variant polypeptide is a sequence having the same number or fewer amino acids than a polypeptide of the present invention that has at least a 99% probability of being the same as the polypeptide of the present invention, measured as having an E value of 0.01 or less using the BLASTP algorithm set at the default parameters.

In addition to having a specified percentage identity to an inventive polynucleotide or polypeptide sequence, variant polynucleotides and polypeptides preferably have additional structure and/or functional features in common with the inventive polynucleotide or polypeptide. Polypeptides having a specified degree of identity to a polypeptide of the present invention share a high degree of similarity in their primary structure and have substantially similar functional properties. In addition to sharing a high degree of similarity in their primary structure to polynucleotides of the present invention, polynucleotides having a specified degree of identity to, or capable of hybridizing to, an inventive polynucleotide preferably have at least one of the following features: (i) they contain an open reading frame or partial open reading frame encoding a polypeptide having substantially the same functional properties as the polypeptide encoded by the inventive polynucleotide; or (ii) they contain identifiable domains in common.

In certain embodiments, variant polynucleotides hybridize to a polynucleotide of the present invention under stringent conditions. As used herein, “stringent conditions” refers to prewashing in a solution of 6×SSC, 0.2% SDS; hybridizing at 65° C., 6×SSC, 0.2% SDS overnight; followed by two washes of 30 minutes each in 1×SSC, 0.1% SDS at 65° C. and two washes of 30 minutes each in 0.2×SSC, 0.1% SDS at 65° C.

The present invention also encompasses polynucleotides that differ from the disclosed sequences but that, as a consequence of the discrepancy of the genetic code, encode a polypeptide having similar enzymatic activity as a polypeptide encoded by a polynucleotide of the present invention. Thus, polynucleotides comprising sequences that differ from the polynucleotide sequences disclosed herein (or complements, reverse sequences, or reverse complements of those sequences) as a result of conservative substitutions are encompassed within the present invention. Additionally, polynucleotides comprising sequences that differ from the inventive polynucleotide sequences or complements, reverse complements, or reverse sequences as a result of deletions and/or insertions totaling less than 10% of the total sequence length are also contemplated by and encompassed within the present invention. Similarly, polypeptides comprising sequences that differ from the inventive polypeptide sequences as a result of amino acid substitutions, insertions, and/or deletions totaling less than 10% of the total sequence length are contemplated by and encompassed within the present invention, provided the variant polypeptide has similar activity to the inventive polypeptide.

A polypeptide of the present invention may be conjugated to a signal (or leader) sequence at the N-terminal end of the protein which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

As used herein, the term "x-mer," with reference to a specific value of "x," refers to a polynucleotide comprising at least a specified number ("x") of contiguous residues of any of the polynucleotides identified as SEQ ID NO: 8–21, 56–58 and 82–89. The value of x may be from about 20 to about 600, depending upon the specific sequence.

Polynucleotides of the present invention comprehend polynucleotides comprising at least a specified number of contiguous residues (x-mers) of any of the polynucleotides identified as SEQ ID NO: 8–21, 56–58 and 82–89 or their variants. According to preferred embodiments, the value of x is preferably at least 20, more preferably at least 40, more preferably yet at least 60, and most preferably at least 80. Thus, polynucleotides of the present invention include polynucleotides comprising a 20-mer, a 40-mer, a 60-mer, an 80-mer, a 100-mer, a 120-mer, a 150-mer, a 180-mer, a 220-mer a 250-mer, or a 300-mer, 400-mer, 500-mer or 600-mer of a polynucleotide identified as SEQ ID NO: 8–21, 56–58 and 82–89 or a variant of one of the polynucleotides identified as SEQ ID NO: 8–21, 56–58 and 82–89.

In general, the inventive polypeptides and polynucleotides, may be prepared using any of a variety of procedures. For example, polypeptides may be produced recombinantly by inserting a polynucleotide that encodes the polypeptide into an expression vector and expressing the polypeptide in an appropriate host. Any of a variety of expression vectors known to those of ordinary skill in the art may be employed. Expression may be achieved in any appropriate host cell that has been transformed or transfected with an expression vector containing a polynucleotide that encodes a recombinant polypeptide. Suitable host cells include prokaryotes, yeast and higher eukaryotic cells. Preferably, the host cells employed are *E. coli*, mycobacteria, insect, yeast or a mammalian cell line such as COS or CHO. The polynucleotides expressed in this manner may encode naturally occurring antigens, portions of naturally occurring antigens, or other variants thereof.

Polynucleotides of the present invention may be isolated by screening a *M. vaccae* genomic DNA library as described below in Example 1. Alternatively, polynucleotides encoding *M. vaccae* epitopes may be obtained by screening an appropriate *M. vaccae* cDNA or genomic DNA library for DNA sequences that hybridize to degenerate oligonucleotides derived from amino acid sequences of isolated epitopes. Suitable degenerate oligonucleotides may be designed and synthesized, and the screen may be performed as described, for example in Sambrook et al. *Molecular cloning: a laboratory manual* CSHL Press: Cold Spring Harbor, N.Y., 1989. Polymerase chain reaction (PCR) may be employed to isolate a nucleic acid probe from genomic DNA, or a cDNA or genomic DNA library, using techniques well known in the art. The library screen may then be performed using the isolated probe.

Regardless of the method of preparation, the epitopes described herein have the ability to induce an immunogenic response. More specifically, as discussed above, the epitopes have the ability to induce cell proliferation and/or cytokine production (for example, interferon-γ and/or interleukin-12 production) in T cells, NK cells, B cells or macrophages derived from a mycobacteria-immune individual.

The selection of cell type for use in evaluating an immunogenic response to an epitope will depend on the desired response. For example, interleukin-12 production is most readily evaluated using preparations containing T cells, NK cells, B cells and/or macrophages derived from mycobacteria-immune individuals may be prepared using methods well known in the art. For example, a preparation of peripheral blood mononuclear cells (PBMCs) may be employed without further separation of component cells. PBMCs may be prepared, for example, using density centrifugation through Ficol™ (Winthrop Laboratories, NY). T cells for use in the assays described herein may be purified directly from PBMCs. Alternatively, an enriched T cell line reactive against mycobacterial proteins, or T cell clones reactive to individual mycobacterial proteins, may be employed. Such T cell clones may be generated by, for example, culturing PBMCs from mycobacteria-immune individuals with mycobacterial proteins for a period of 2–4 weeks. This allows expansion of only the mycobacterial protein-specific T cells, resulting in a line composed solely of such cells. These cells may then be cloned and tested with individual proteins, using methods well known in the art, to more accurately define individual T cell specificity. Assays for cell proliferation or cytokine production in T cells, NK cells, B cells or macrophages may be performed, for example, using the procedures described below.

Among the immunogenic epitopes, polypeptides and/or polynucleotides of the present invention, those having superior therapeutic properties may be distinguished based on the magnitude of the responses in the above assays and based on the percentage of individuals for which a response is observed. In addition, epitopes having superior therapeutic properties will not stimulate cell proliferation or cytokine production in vitro in cells derived from more than about 25% of individuals that are not mycobacteria-immune, thereby eliminating responses that are not specifically due to mycobacteria-responsive cells. Thus, those antigens that induce a response in a high percentage of T cell, NK cell, B cell or macrophage preparations from mycobacteria-immune individuals (with a low incidence of responses in cell preparations from other individuals) have superior therapeutic properties.

Epitopes with superior therapeutic properties may also be identified based on their ability to diminish the severity of *M. tuberculosis* infection, or other mycobacterial infection, in experimental animals, when administered as a vaccine. Suitable vaccine preparations for use in experimental animals are described in detail below.

Portions and other variants of the inventive polypeptides may be generated by synthetic or recombinant means. Synthetic polypeptides having fewer than about 100 amino acids, and generally fewer than about 50 amino acids, may be generated using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain. See Merrifield, *J. Am. Chem. Soc.* 85:2149–2154, 1963. Equipment for automated synthesis of polypeptides is commercially available from suppliers such as Perkin Elmer/Applied BioSystems, Inc. (Foster City, Calif.), and may be operated according to the manufacturer's instructions. Variants of a native epitope may be prepared using standard mutagenesis techniques, such as oligonucleotide-directed site-specific mutagenesis. Sections of the DNA sequence may also be removed using standard techniques to permit preparation of truncated polypeptides.

The present invention also provides fusion proteins comprising a first and a second inventive polypeptide or, alternatively, a polypeptide of the present invention and a known *M. tuberculosis* antigen, such as the 38 kDa antigen described in Andersen and Hansen, *Infect. Immun.* 57:2481–2488, 1989, together with variants of such fusion proteins. In a related aspect, genetic constructs comprising a first and a second inventive polynucleotide are also provided. Preparation of a construct comprising multiple epitopes of the present invention and expression of the corresponding recombinant protein is detailed below in Example 4.

In general, a polynucleotide encoding a fusion protein of the present invention is constructed using known recombinant DNA techniques to assemble separate DNA sequences encoding the first and second polypeptides into an appropriate expression vector. The 3' end of a DNA sequence encoding the first polypeptide is ligated, with or without a peptide linker, to the 5' end of a DNA sequence encoding the second polypeptide so that the reading frames of the sequences are in phase to permit mRNA translation of the two DNA sequences into a single fusion protein that retains the biological activity of both the first and the second polypeptides.

A peptide linker sequence may be employed to separate the first and the second polypeptides by a distance sufficient to ensure that each polypeptide fold into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39–46, 1985; Murphy et al., *Proc. Natl. Acad. Sci. USA* 83:8258–8262, 1986; and U.S. Pat. Nos. 4,935,233 and 4,751,180. The linker sequence may be from 1 to about 50 amino acids in length. Peptide linker sequences are not required when the first and second polypeptides have non-essential N-terminal amino acid regions that can be used to separate the functional domains and prevent steric interference. The ligated DNA sequences encoding the fusion proteins are cloned into suitable expression systems using techniques known to those of ordinary skill in the art.

In another aspect, the present invention provides methods for using one or more of the inventive polypeptides or fusion proteins (or polynucleotides encoding such polypeptides or fusion proteins) to induce protective immunity against disorders such as tuberculosis in a patient. As used herein, a "patient" refers to any warm-blooded animal, preferably a human. A patient may be afflicted with a disease, or may be free of detectable disease or infection. In other words, protective immunity may be induced to prevent or treat disorders.

In related aspects, the *M. vaccae* polynucleotides and polypeptides of the present invention may be employed to activate T cells and NK cells; to stimulate the production of cytokines (in particular Th1 class of cytokines) in human PBMC; to produce anti-epitope antibodies; to induce long-term memory cells and/or to enhance an immune response against an antigen.

For use in such methods, the polypeptide, fusion protein or polynucleotide is generally present within a composition, such as a pharmaceutical composition or an immunogenic composition. Compositions may comprise one or more polypeptides, each of which may contain one or more of the above sequences (or variants thereof), and a physiologically acceptable carrier. Immunogenic compositions may comprise one or more of the above polypeptides and an immunostimulant, such as an adjuvant or a liposome, into which the polypeptide is incorporated. Such compositions may also contain other antigens and/or polypeptides, either incorporated into a fusion protein or present within a separate polypeptide. Examples of polypeptides which may be usefully employed in combination with the polypeptides of the present invention include other mycobacterial antigens and flt3 ligands, as disclosed in U.S. Pat. No. 5,554,512, the disclosure of which is hereby incorporated in its entirety.

Alternatively, a composition of the present invention may contain a polynucleotide encoding one or more polypeptides as described above, such that the polypeptide is generated in situ. In such compositions, the polynucleotide may be present within any of a variety of delivery systems known to those of ordinary skill in the art, including nucleic acid expression systems, bacterial and viral expression systems. Appropriate nucleic acid expression systems contain the necessary DNA/RNA sequences for expression in the patient (such as a suitable promoter and terminator signal). Bacterial delivery systems involve the administration of a bacterium (such as *Bacillus* Calmette-Guerin) that expresses an immunogenic epitope of the polypeptide on its cell surface. In a preferred embodiment, the DNA and/or RNA may be introduced using a viral expression system (e.g., vaccinia or other poxvirus, retrovirus, or adenovirus), that may involve the use of a non-pathogenic, or defective, replication competent virus. Techniques for incorporating DNA and/or RNA into such expression systems are well known in the art. The DNA may also be "naked," as described, for example, in Ulmer et al., *Science* 259:1745–1749, 1993 and reviewed by Cohen, *Science* 259:1691–1692, 1993. The uptake of naked DNA may be increased by coating the DNA onto biodegradable beads, which are efficiently transported into the cells. Methods for the administration of polynucleotide sequences comprising DNA and/or RNA include those disclosed in U.S. Pat. Nos. 5,580,859 and 5,589,466.

A polynucleotide composition as described above may be administered simultaneously with or sequentially to either a polypeptide of the present invention or a known mycobacterial antigen, such as the 38 kDa antigen from *M. tuberculosis*. For example, administration of DNA encoding a polypeptide of the present invention, may be followed by administration of an antigen in order to enhance the protective immune effect of the composition.

Routes and frequency of administration of the inventive compositions, as well as dosage, will vary from individual to individual and may parallel those currently being used in immunization using *M. bovis* BCG. In general, the compositions may be administered by injection (e.g., intradermal, intramuscular, intravenous or subcutaneous), intranasally (e.g., by aspiration) or orally. Between 1 and 3 doses may be administered for a 1–36 week period. Preferably, 3 doses are administered, at intervals of 3–4 months, and booster vaccinations may be given periodically thereafter. Alternate protocols may be appropriate for individual patients. A suitable dose is an amount of polypeptide or polynucleotide that, when administered as described above, is capable of raising an immune response in a patient sufficient to protect the patient from mycobacterial infection for at least 1–2 years. In general, the amount of polypeptide present in a dose (or produced in situ by the polynucleotide in a dose) ranges from about 1 pg to about 100 mg per kg of host, typically from about 10 pg to about 1 mg, and preferably from about 100 pg to about 1 μg. Suitable dose sizes will vary with the size of the patient, but will typically range from about 0.1 ml to about 5 ml.

While any suitable carrier known to those of ordinary skill in the art may be employed in the pharmaceutical compositions of this invention, the type of carrier will vary depending on the mode of administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactic galactide) may also be employed as carriers for the pharmaceutical compositions of this invention. Suitable biodegradable microspheres are disclosed, for example, in U.S. Pat. Nos. 4,897,268 and 5,075,109.

Any of a variety of immunostimulants, such as an adjuvant, may be employed in the compositions of this invention to non-specifically enhance the immune response. Most adjuvants contain a substance designed to protect the antigen from rapid catabolism, such as aluminum hydroxide or mineral oil, and a non-specific stimulator of immune responses, such as lipid A, *Bordetella pertussis, M. tuberculosis*, or, as discussed below, *M. vaccae*. Suitable adjuvants are commercially available as, for example, Incomplete Freund's Adjuvant (IFA) and Complete Freund's Adjuvant (Difco Laboratories, Detroit, Mich.), and Merck Adjuvant 65 (Merck and Company, Inc., Rahway, N.J.). Other suitable adjuvants include alum, biodegradable microspheres, monophosphoryl lipid A and Quil A.

The following examples are offered by way of illustration and not by way of limitation.

EXAMPLE 1

Cloning and Selection of Immunogenic *M. Vaccae* Epitopes

*M. vaccae* (ATCC Number 15483, Manassas, Va.) was cultured in medium 90 (yeast extract, 2.5 g/l; tryptone, 5 g/l; glucose, 1 g/l) at 37° C. for four days. Genomic DNA was isolated from these cells following standard protocols and then digested with restriction endonuclease Sau3A under conditions that produced DNA fragments of approximately 0.25 kb. The fragments were purified using the QIAquick PCR clean-up system (Qiagen, Venlo, The Netherlands).

To express the cloned *M. vaccae* DNA in three different reading frames, the pcDNA3 expression vector (Invitrogen, Carlsbad, Calif.) was modified by insertion of a human growth hormone signal peptide (to facilitate recombinant protein secretion) amplified with three different 3' primers. These primers allowed the insertion of one or two extra base pairs into the PCR product to shift the reading frame of the expressed polypeptide. The primers were AD105 (human growth hormone 5' primer; SEQ ID NO: 1) and the three human growth hormone (hGH) 3' primers AD106, AD107 and AD108 (SEQ ID NO: 2–4, respectively). From these PCR fragments, most of the hGH sequence downstream of the leader sequence cleavage site was removed by digestion with the restriction endonuclease BsgII. The hGH PCR fragments were then cloned into the pcDNA3 expression vector following digestion with the restriction endonucleases HindIII and BamHI. The nucleotide sequence of the inserted fragments are given in SEQ ID NO: 5–7, with the corresponding amino acid sequences being provided in SEQ ID NO: 61–63, respectively. Three expression libraries (one for each of the three reading frames) were constructed by cloning the 0.25 kb *M. vaccae* PCR fragments, prepared as described above, into the BamHI cloning site of the chimeric pcDNA3/human growth hormone vectors (pcDNA3-hGH1', pcDNA3-hGH2' and pcDNA3-hGH3'). Replica lift master plates were made of bacterial colonies transformed with the library constructs and stored. Plasmid DNA, prepared from these colonies, was divided into 500 pools, each containing DNA from 40 to 50 plasmids. The DNA was transfected into COS7 cells using lipofectamine (BRL Life Technologies, Gaithersburg Md.) and the immunogenic properties of the products of each group were determined by a spleen cell assay, wherein the production of IFN-γ in cultures of spleen cells obtained from mice primed with heat-killed *M. vaccae* was determined by ELISA as described below.

Plasmid pools that encoded recombinant polypeptides eliciting an immune response (as determined by the ability to increase IFN-γ production in the spleen cell assay), were subdivided into smaller pools containing 10 plasmids each and these pools were again transfected into COS7 cells. The culture supernatants of these cells were subjected to the spleen cell assay as described above.

After three rounds of screening, 120 plasmids were identified that encoded recombinant polypeptides stimulating spleen cells of heat-killed *M. vaccae*-immunised mice to produce IFN-γ. The 120 supernatants of COS7 cells transfected with these plasmids were screened in two additional assays, namely the mouse memory assay and the human peripheral blood mononuclear cell (PBMC) assay. In the mouse long-term memory assay, mice were injected with a sub-lethal dose of $10^4$ colony forming units (CFU) of *M. tuberculosis*. After 4 weeks, the mice were treated with antibiotics for a further 4 weeks to cure them of *M. tuberculosis* infection, followed by a resting period of 4 weeks. A second injection of live *M. tuberculosis* ($5\times10^5$ CFU) was given before the immunogenicity of the plasmid products was measured four days later using the spleen cell assay described above.

In the PBMC assay, the 120 supernatants of COS7 cells transfected with the plasmids were screened for the ability to induce T-cell proliferation and IFN-γ production in peripheral blood cells from mycobacteria-immune human donors. These donors were known to be PPD (purified protein derivative from *M. tuberculosis*) positive and their T cells were shown to proliferate and produce IFN-γ in response to PPD. Donor PBMCs and COS7 supernatants were cultured in medium comprising RPMI 1640 supplemented with 10% (v/v) autologous serum, penicillin (60 μg/ml), streptomycin (100 μg/ml), and glutamine (2 mM). After 3 days, 50 μl of medium was removed from each well for the determination of IFN-γ levels, as described below. The plates were cultured for a further 4 days and then pulsed with 1 μCi/well of tritiated thymidine for 18 hours, harvested and tritium uptake determined using a scintillation counter. Supernatants that stimulated proliferation in two replicates at levels two-fold greater than the proliferation observed in cells cultured in medium alone were considered positive.

IFN-γ was measured using an enzyme-linked immunosorbent assay (ELISA) as follows. ELISA plates were coated with a mouse monoclonal antibody directed to human IFN-γ (Endogen, Wobural, Mass.) by incubating the wells with 1 μg/ml antibody in phosphate-buffered saline (PBS) for 4 hours at 4° C. Wells were blocked with PBS containing 0.2% Tween 20 for 1 hour at room temperature. The plates were then washed four times in PBS/0.2% Tween 20, and samples diluted 1:2 in culture medium in the ELISA plates were incubated overnight at room temperature. The plates were again washed, and a biotinylated polyclonal rabbit anti-human IFN-γ serum (Endogen), diluted to 1 μg/ml in PBS, was added to each well. The plates were then incubated for 1 hour at room temperature, washed, and horseradish peroxidase-coupled avidin A (Vector Laboratories, Burlingame, Calif.) was added at a 1:4,000 dilution in PBS. After a further 1 hour incubation at room temperature, the plates were washed and orthophenylenediamine (OPD) substrate added. The reaction was stopped after 10 minutes with 10% (v/v) HCl. The optical density (OD) was determined at 490 nm. Supernatants that resulted in both replicates giving an OD two-fold greater than the mean OD from cells cultured in medium alone were considered positive.

From the results of these two assays, 59 plasmids were identified that encoded recombinant polypeptides containing immunogenic determinants, or epitopes. These epitopes were found to elicit an immune response in mice and humans, and are cross-reactive with *M. tuberculosis* immunogenic determinants inducing long term responses. These plasmids were tested for their ability to induce protective immunity in the mouse model of tuberculosis as follows. Each plasmid (100 μg of DNA) was injected IM in the tibialis anterior of anaesthetised mice, three times every three weeks. After nine weeks, the mice were challenged with *M. tuberculosis* ($5\times10^5$ CFU). Organ homogenates from lungs and spleens were prepared in week 12 and plated out on 7H9 medium supplemented with oleic acid-albumin-dextrose-catalase (OADC) to determine the number of CFU present in each homogenate. Results were recorded after a two-week incubation period.

Using the protocols described above, eight plasmids containing immunogenic epitopes were selected. After identification of the putative open reading frames (ORFs) in these constructs, the *M. vaccae* fragments comprising only the ORF-portion were sub-cloned into pcDNA3-hGH' as described above. These plasmids were called DNA5, DNA9, DNA26, DNA27, DNA29, DNA37, DNA44 and DNA45. Three ORFs, referred to as A, B and C, were identified in DNA9. Open reading frames B and C were in the reverse orientation and were discarded. ORF A was cloned separately and the resulting plasmid was called DNA9A. The determined genomic DNA sequences of the inserts of DNA5, DNA9A, DNA26, DNA27, DNA29, DNA37, DNA42, DNA44 and DNA45 are given in SEQ ID NO: 13–21, respectively, with the amino acid sequences of the corresponding ORFs being provided in SEQ ID NO: 69–77, respectively. More than one epitope was identified in the inserts of the plasmids DNA5 and DNA27. These epitopes were not separated by cloning and were tested as multiple epitopes in all the assays. The determined genomic DNA sequences of epitope 1, epitope 2 and epitope 3 of DNA5, and of epitope 1 and epitope 2 of DNA27 are given in SEQ ID NO: 8–12, respectively, with the corresponding amino acid sequences being provided in SEQ ID NO: 64–68, respectively. The determined epitope DNA sequences were compared to sequences in the EMBL DNA database using the FASTA computer algorithm. The corresponding protein sequences (DNA translated to protein in each of 6 reading frames) were compared to sequences in the SwissProt database using the computer algorithm FASTX. Comparisons of DNA sequences provided in SEQ ID NO: 8–21 to sequences in the EMBL DNA database (using FASTA) and amino acid sequences provided in SEQ ID NO: 64–77 to sequences in the SwissProt database (using FASTX) were made as of Mar. 21, 1999.

The predicted amino acid sequences of DNA5 epitope 2, DNA27 epitope 1, DNA9A, DNA29, DNA37, DNA44 and DNA45 (provided in SEQ ID NO: 65, 67, 70, 73, 74, 76 and 77, respectively) were found to have less than 50% identity, determined as described above, to sequences in the SwissProt database using FASTX. The predicted amino acid sequences of DNA5 epitopes 1 and 3 (provided in SEQ ID NO: 64 and 66, respectively) were found to have less than 75% identity, determined as described above, to sequences in the SwissProt database using FASTX. No matches were found to the predicted amino acid sequence of DNA27 epitope 2 and DNA26 (provided in SEQ ID NO: 68 and 71, respectively). Table 1, below, shows the results of the comparison of the inventive amino acid sequences with those in the SwissProt database using FASTX as described above, wherein "No. of identical residues" represents the number of identical residues within the aligned portion.

TABLE 1

| | SEQ ID NO: | Length (residues) | Length of alignment (residues) | No. of identical residues | % of identical residues |
|---|---|---|---|---|---|
| DNA5, epitope 1 | 64 | 13 | 11 | 8 | 61 |
| DNA5, epitope 2 | 65 | 32 | 31 | 10 | 32 |
| DNA5, epitope 3 | 66 | 26 | 25 | 14 | 53 |
| DNA9A | 70 | 75 | 68 | 24 | 32 |
| DNA26 | 71 | 97 | No Hits | | |
| DNA27, epitope 1 | 67 | 38 | 30 | 16 | 42 |
| DNA27, epitope 2 | 68 | 11 | No Hits | | |
| DNA29 | 73 | 46 | 40 | 17 | 37 |
| DNA37 | 74 | 87 | 80 | 26 | 32 |
| DNA44 | 76 | 44 | 35 | 17 | 38 |
| DNA45 | 77 | 59 | 52 | 21 | 35 |

EXAMPLE 2

Expression of Recombinant Epitopes in Prokaryotic and Eukaryotic Cells

Epitope DNA was subcloned into vectors for expression of polypeptides in bacterial and eukaryotic cells. The bacterial expression vector was a modified pET16 vector (Novagen, Madison, Wis.). Inserts from all the plasmids except for DNA9, were amplified with primers AD136 and AD133 (SEQ ID NO: 22 and 23, respectively) and cloned by blunt-end ligation into the pET16 vector that was EcoRI-digested and end-filled with DNA polymerase PfuI (Stratagene, La Jolla Calif.). The insert of DNA9A was amplified with AD250 and AD251 (SEQ ID NO: 24 and 25, respectively) and cloned into the pET16 vector as described above.

To express the polypeptides in eukaryotic cells, the pcDNA3 vector (Invitrogen) was modified to include a histidine tag at the 3' end of the cloning site. This was done by cloning the double-stranded oligonucleotide AD180/AD181 into pcDNA3 digested with BamHI and EcoRI. The sequences of oligonucleotides AD180 and AD181 are given in SEQ ID NO: 26 and 27, respectively. Plasmid inserts were amplified with the hGH-specific N-terminus 5' primer AD134 (SEQ ID NO: 28) and an epitope-specific 3' end primer, using the pcDNA3-hGH' constructs as DNA template. The sequences of the epitope-specific 3' primers AD151 (DNA5), AD153 (DNA26), AD154 (DNA27), AD155 (DNA29), AD158 (DNA42), AD159 (DNA44), AD160 (DNA45), AD167 (DNA37) and AD182 (DNA9) are listed in SEQ ID NO: 29–37, respectively.

This vector was again modified to remove excess sequence (42 nucleotides) between the hGH leader sequence and the expressed sequence, so that the hGH' sequence in this construct was reduced to the leader sequence and the first 5 N-terminal amino acids of the hGH sequence only. Using the pcDNA3-hGH3' construct as DNA template, the shortened fusion partner was amplified by PCR using primers AD105 (SEQ ID NO: 1) and AD222 (SEQ ID NO: 38). Cloning into pcDNA3-His was done at the HindIII and BamHI sites and the resulting construct was called pcDNA3-hGHls/His. The determined DNA sequence of the hGH-fusion partner cloned into pcDNA3-hGH-ls is given in SEQ ID NO: 39 and the corresponding amino acid sequence in SEQ ID NO: 78. The construct consisting of the insert from DNA9A was prepared by PCR amplification using primers AD223 and AD226 (SEQ ID NO: 40 and 41, respectively).

EXAMPLE 3

Immunogenicity of Recombinant Epitope Constructs

This example describes the results of immunogenicity studies performed with eight selected recombinant epitopes in either DNA or recombinant polypeptide form.

A. Stimulation of Human Peripheral Blood Mononuclear Cells (PBMC) to Proliferate and Secrete Interferon Gamma (IFN-γ) in vitro The recombinant epitopes (1 and 10 μg) expressed by the pET16 bacterial expression system were cultured with human PBMC at 37° C. After 48 hours, IFN-γ secretion was measured by enzyme-linked immunoassay (ELISA) following standard procedures. Parallel cultures were pulsed with tritiated thymidine and DNA synthesis was used to assess PBMC proliferation. For comparison, cells were also cultured with Purified Protein Derivative (PPD) from *M. tuberculosis* and with PBS as a negative control.

As shown in Table 2, all recombinant epitopes have the ability to stimulate IFN-γ production in at least some PBMC samples. Of the 12 PBMC samples tested, 10 were PPD positive, i.e., the PBMCs from these samples produced IFN-γ when cultured with PPD, and 2 were PPD-negative. PBMC responses were considered positive when the amount of IFN-γ produced was at least 3-fold higher than the IFN-γ produced by the PBS control samples. Recombinant epitopes 5 (corresponding to DNA5) and 44 (corresponding to DNA44) stimulated IFN-γ production in 100% of the $PPD^+$ samples. Recombinant epitope 27 (corresponding to DNA27) stimulated IFN-γ production in 80% of the $PPD^+$ samples. Recombinant epitopes 26 and 37 (corresponding to DNA26 and DNA37, respectively) stimulated IFN-γ production in 70% of the $PPD^+$ samples, whereas epitope 45 (corresponding to DNA45) stimulated 20% $PPD^+$ of the PBMC samples. PBMCs from $PPD^-$ samples did not respond significantly to any of the recombinant epitopes. This demonstrates that the epitopes are immunogenic in humans and trigger a recall response in samples from donors that were previously exposed to mycobacteria.

TABLE 2

Stimulation of IFN-γ production in human PBMC by recombinant epitopes

| Human | PBS | PPD | Recombinant Epitopes | | | | | |
|---|---|---|---|---|---|---|---|---|
| PBMC | control | control | 26 | 37 | 44 | 45 | 5 | 27 |
| G97022 | <0.1 | 0.16 | 0.3 | 0.3 | 0.4 | <0.1 | 0.5 | 0.1 |
| G97037 | <0.1 | 0.3 | 0.3 | 0.3 | 0.8 | 0.2 | 0.3 | 0.3 |
| G97001 | <0.1 | 4.5 | 0.6 | 1 | 3.5 | 0.2 | 1.8 | 1.7 |
| G97008 | <0.1 | 4.4 | 0.16 | 0.5 | 4 | <0.1 | 0.73 | 0.9 |
| G97011 | 0.25 | 4.9 | 0.9 | 0.5 | 1.2 | 0.25 | 2.8 | 1.2 |
| G97030 | <0.1 | 1.8 | 0.5 | 0.2 | 3.5 | 0.1 | 1.8 | 3 |
| G97033 | 0.12 | 4.5 | 0.5 | 0.25 | 3.4 | 0.2 | 1.7 | 1 |
| G97010 | <0.1 | >4 | >4 | >4 | >4 | 1 | >4 | >4 |
| G97028 | <0.1 | >4 | >4 | >4 | >4 | 1.2 | >4 | >4 |
| G97020 | <0.1 | 1 | 0.3 | 0.25 | >4 | <0.1 | 1.5 | 0.5 |
| G97032 | <0.1 | >4 | 0.5 | 1.2 | >4 | <0.1 | 1.4 | 0.5 |
| G97035 | <0.1 | 3.5 | 0.4 | 3.5 | >4 | <0.1 | 1 | 1 |

*Results are expressed as IFN-γ in ng/ml

Immunogenicity of the epitopes in humans was further demonstrated by the proliferative response of the human PBMC samples to both PPD and recombinant epitopes. The ability of the recombinant epitopes to stimulate PBMC proliferation was expressed as a stimulation index. A proliferation stimulus is considered positive when it is 5 times greater than the mean background proliferation produced by the medium-only control. As shown in Table 3, all recombinant epitopes were found to have the ability to stimulate PBMC proliferation in at least some of the human PBMC samples. Recombinant epitopes 26 and 27 stimulated PBMC proliferation in 92% of the samples, while recombinant epitopes 5, 37 and 44 stimulated proliferation in 83% of the samples. Epitope 45 stimulated PBMC proliferation in 17% of the samples. Stimulation of PBMC by PPD was 83%.

TABLE 3

Stimulation of PMBC proliferation

| Human | | Recombinant epitopes | | | | | |
|---|---|---|---|---|---|---|---|
| PBMC | PPD | 5 | 26 | 27 | 37 | 44 | 45 |
| G97022 | 5* | 12 | 14 | 3 | 20 | 20 | 1 |
| G97037 | 35 | 12 | 25 | 20 | 15 | 30 | 1 |
| G97001 | 5 | 6 | 6 | 5 | 8 | 7 | 1 |
| G97008 | 60 | 20 | 30 | 15 | 40 | 60 | 2 |
| G97011 | 40 | 33 | 30 | 27 | 30 | 30 | 3 |
| G97030 | 100 | 140 | 120 | 140 | 120 | 140 | 30 |
| G97033 | 20 | 12 | 12 | 11 | 10 | 15 | 1 |
| G97010 | 2 | 4 | 2 | 6 | 2 | 4 | 2 |
| G97028 | 60 | 48 | 60 | 40 | 55 | 52 | 12 |
| G97020 | 10 | 10 | 10 | 8 | 10 | 10 | 1 |
| G97032 | 45 | 30 | 35 | 33 | 38 | 42 | 2 |
| G97035 | 3 | 4 | 5 | 6 | 3 | 4 | 2 |

*Results of human PBMC proliferation are expressed as Stimulation Index.

B. Immunization of Mice with DNA Epitopes

Protective immunity against subsequent infection with *M. tuberculosis* was induced in BALB/cByJ mice after injection of DNA encoding eight of the recombinant epitopes in pcDNA-hGH'/His or pcDNA3-hGHls/His constructs.

Induction of protective immunity was considered positive when a mean 0.5 log reduction in CFU in lung homogenates, compared to the mean CFUs from non-immunized control mice, was observed following subsequent infection with *M. tuberculosis*. A plasmid without an insert was used as control. The reduction in CFUs after epitope DNA immunization was also compared with the known immunogenicity of *M. bovis* BCG. The results clearly show a reduction in CFUs in all the mice tested, suggesting the induction of protective immunity by the recombinant epitope DNA. In six of the groups, the reduction in CFUs was greater than 50% and in three of the groups the reduction was comparable to that induced by injection with *M. bovis* BCG.

TABLE 4

Protective immunity in mice induced by genetic immunization with eight pcDNA-hGH'/His and pcDNA3-hGHls/His constructs

| Epitope construct | SEQ ID NO: | Number of Mice | Number of mice with reduced CFUs | % Mice with Reduced CFUs |
|---|---|---|---|---|
| Control plasmid | | 14 | 2 | 14 |
| DNA5 | 13 | 11 | 4 | 36 |
| DNA9 | 14 | 13 | 7 | 55 |
| DNA26 | 15 | 10 | 7 | 70 |
| DNA27 | 16 | 13 | 7 | 55 |
| DNA29 | 17 | 13 | 7 | 55 |
| DNA37 | 18 | 13 | 8 | 62 |
| DNA44 | 20 | 13 | 6 | 46 |
| DNA45 | 21 | 13 | 8 | 62 |
| M. bovis BCG | | 23 | 17 | 74 |

The induction of cytotoxic T lymphocytes (CTL), cytokines (IFN-γ, IL-4, IL-6 and IL-10), and proliferative and antibody responses upon genetic immunization with eight pcDNA-hGH'/His or pcDNA3-hGHls/His constructs were assessed as follows.

CTL Assay:

Cytolytic (CTL) activity in spleen cells of DNA-immunized BALB/cByJ mice was measured following a standard two-step procedure using the MHC haplotype matching target cells, BALB-3T3 (ATCC No. CRL-163, American Type Culture Collection, Manassas, Va.). Target cells were prepared by transfecting BALB/3T3 cells with eight pcDNA-hGH'/His or pcDNA3-hGHls/His epitope DNA constructs. Stably transfected cell lines were produced by geneticin selection (G418; Gibco BRL Life Technologies) and single cells were isolated by limiting dilution. Clones expressing epitopes were selected by RT-PCR using primers AD105 and AD181 (SEQ ID NO: 1 and 27, respectively). Spleen cells of DNA-immunized mice were cultured in cDMEM enriched with 10% FCS in the presence of mytomycin-treated BALB-3T3 cells transfected with matching epitope DNA to re-stimulate cytotoxic T cells in vitro. Cultures were incubated at 37° C. under 10% $CO_2$ for 6 days. Cytolytic activities were monitored by incubating a fraction of each stimulated cell culture with DNA-matched target cells that were pulsed with $^{51}$Chromium, and measuring $^{51}$Chromium release in the supernatant of cell cultures. As shown in Table 5, specific CTL activity was detected in the spleens of mice immunized with four of the DNA constructs tested.

Cytokine and Proliferative Responses:

Cytokine production and proliferative responses of spleen cells from DNA-immunized BALB/cByJ mice were assessed following in vitro re-stimulation with recombinant epitopes. Cytokine and proliferative responses were measured by ELISA and 3H-thymidine pulse, respectively, as described above. As shown in Table 5, spleen cells from the six groups tested produced the Th1 cytokine IFN-γ. No Th2 cytokines (e.g. IL-4, IL-6 and IL-10) were detected in supernatants of stimulated cells. Proliferative responses were low and detected in spleen cells from two immunized groups only.

Antibody Responses

Blood samples from three DNA-immunized BALB/cByJ mice were collected two weeks after the last DNA injection and sera were prepared according to standard procedures. The presence of anti-epitope antibodies was determined by ELISA. The wells of a microtitre plate were coated with 500 ng of recombinant epitope. Antibody titres were measured by adding serial dilutions of serum into the wells. Bound antibodies were detected according to ELISA procedures as described above. As shown in Table 5, anti-epitope antibodies were detected in two blood samples tested. ELISA assays were also performed to determine whether the antibodies belonged to the IgG1 or IgG2a subclasses, using standard protocols. The results showed that the antibodies belonged to the IgG2a subclass, which is characteristic of a Th1 antibody response.

The data summarized in Table 5 indicate that immunization with epitope DNA induced an immune response in mice. Furthermore, the cellular and humoral responses detected in the DNA-immunized mice demonstrated that a Th1 response was generated.

TABLE 5

Cytotoxic lymphocyte induction, cytokine responses, proliferation and antibody production induced in mice by genetic immunization with eight pcDNA-hGH'/His or pcDNA3-hGHls/His constructs.

| Epitope constructs | SEQ ID NO: | CTL induction (% Specific lysis)* | Cytokine responses (IFN-γ in ng/ml)** | Proliferation (Stimulation Index) | Antibodies (titer) |
|---|---|---|---|---|---|
| DNA5 | 13 | 30 | 15 | not detected | not detected |
| DNA9A | 14 | 10 | NT*** | NT | NT |
| DNA26 | 15 | not detected | 30 | 7 | not detected |
| DNA27 | 16 | not detected | 33 | 3 | 1/100 |
| DNA29 | 17 | not detected | NT | NT | NT |
| DNA37 | 18 | not detected | 18 | not detected | not detected |
| DNA44 | 20 | 25 | 23 | not detected | 1/100 |
| DNA45 | 21 | 20 | 12 | not detected | not detected |

*Data shown is the mean % lysis from spleen cells of three mice. Non-specific lysis of control cells was deducted.
**Data shown is the mean IFN-γ in ng/ml obtained from triplicates of spleen cell cultures from three mice. Background IFN-γ produced by control cells was 5–7 ng/ml.
***NT = Not Tested

EXAMPLE 4

Cloning Strategy For *M. Vaccae* Multi-Epitope Constructs

The eight epitopes assayed in Example 4 were assembled to form multi-epitope constructs, of fusion proteins. Specifically, the DNA was amplified with primers containing a BglII 5'-extension and BamHI 3'-extension and was sequentially cloned into the BamHI site of pcDNA3/hGHls/His. The primers were AD223, AD226, AD229, AD230, AD231, AD232, AD233, AD234, AD235, AD236, AD256, AD258, AD259, AD260, AD261 and AD262 (SEQ ID NO: 40–55, respectively).

The insert of plasmid DNA9A was cloned first into the BamHI site of pcDNA3-hGHls/His. The BamHI site of the vector was reconstituted at the 3' end of the cloning junction only and all other inserts except DNA5 were sequentially cloned into the same site. The insert of plasmid DNA5 was cloned last by blunt ligation into the end-filled BamHI site of pcDNA3-hGHls/His. Following this protocol, various combinations of epitopes were cloned into the pcDNA3-hGHls/His vector. The determined DNA sequences of three multi-epitope constructs consisting of 8-mer multi-epitopes (called ME/A, ME/B and ME/D) are shown in SEQ ID NO: 56–58, respectively, and the predicted corresponding amino acid sequences in SEQ ID NO: 79–81, respectively. Each one of these multi-epitope constructs includes each one of the 8 epitopes, but in a different order.

For expression of multi-epitope recombinant proteins in bacteria, the inserts of plasmids ME/A, ME/B and ME/D were subcloned into the modified expression vector pET16. All 8-mer epitope DNA combinations had DNA9A and DNA5 at the 5' and 3' end, respectively. The plasmid inserts were amplified using primers AD272 and AD273 (SEQ ID NO: 59 and 60, respectively) and the purified amplified fragments cloned by blunt-end ligation into the pET16 vector that was EcoRI-digested and end-filled with DNA polymerase PfuI (Stratagene). Recombinant protein was expressed using *E. coli* host cells according to the manufacturer's protocol and purified using standard protocols.

EXAMPLE 5

Immunization of Mice with *M. Vaccae* Multi-Epitope Constructs

This example illustrates the protective immunity against subsequent infection with *M. tuberculosis* in BALB/cByJ mice after injection of multi-epitope constructs in either DNA or recombinant polypeptide form.

BALB/cByJ mice were divided into three groups of six mice that received different treatments. Mice in Group 1 were immunized intraperitoneally with one dose of 500 μg *M. bovis* BCG or PBS. Group 2 mice were immunized three times intramuscularly in the tibialis anterior with 100 μg ME/D DNA or empty vector DNA at three week intervals. Mice in Group 3 were immunized intraperitoneally at three week intervals with either 1 or 2 doses of 50 μg recombinant ME/D in IFA, or 50 μg control protein in IFA. The control protein GV14B consisted of a non-naturally occurring protein derived from DNA encoding the *M. vaccae*-homologue of mycobacterial Elongation factor G and cloned into pET16g3 in reverse orientation.

Three weeks after the last immunization, the mice were challenged with live *M. tuberculosis* ($5\times10^5$ CFU). Organ homogenates from lungs and spleens were prepared after a further three weeks and plated out on 7H9 medium supplemented with oleic acid-albumin-dextrose-catalase (OADC) to determine the number of CFU present in each homogenate. Results were recorded after a two-week incubation period.

Induction of protective immunity was considered positive when a mean 0.5 log reduction in CFU in lung and spleen homogenates, compared to the mean CFUs from non-immunized control mice, was observed following subsequent infection with *M. tuberculosis*. The reduction in CFUs after immunization with ME/D DNA or recombinant ME/D polypeptide was compared with the known immunogenicity of *M. bovis* BCG. The results (FIG. 1) show a reduction in CFUs in the lungs and spleens from mice immunized with the ME/D DNA as well as the recombinant ME/D construct. The protective immunity of the ME/D DNA and the rME/D polypeptide demonstrated by the reduction in both lung and spleen CFUs was greater than the reduction in lung CFU after immunization with single epitope constructs (Table 4).

EXAMPLE 6

Immunogenicity of *M. Vaccae* Multi-Epitope Constructs

This example describes the results of immunogenicity studies performed with three multi-epitope constructs in either DNA or recombinant polypeptide form.

A. Recombinant Multi-Epitope Constructs ME/A, ME/B and ME/D Stimulate Mouse Lymph Node Cells to Proliferate and Secrete IFN-γ in vitro The recombinant multi-epitope constructs, or fusion proteins, rME/A, rME/B and rME/D were screened for their ability to induce T-cell proliferation and IFN-γ in murine lymph node cells. For this assay, BALB/cByJ mice were immunized subcutaneously in each footpad with 10 μg of the recombinant multi-epitope constructs rME/A, rME/B or rME/C diluted in an equal volume of IFA. Mice from the control group received PBS in IFA. Mice were sacrificed after nine days and the lymph nodes removed. Lymph node cells were cultured in medium comprising DMEM supplemented with 10% (v/v) autologous serum, penicillin (60 μg/ml), streptomycin (100 μg/ml), and glutamine (2 mM) in the presence of 0, 0.125, 0.25 or 0.5 μM rME/A, rME/B or rME/D, as well as the control protein GV14B. After 3 days, 50 μl of medium was removed from each well for the determination of IFN-γ levels, as described above. The plates were cultured for a further 4 days and then pulsed with 1 μCi/well of tritiated thymidine for 18 hours. Cells were harvested and tritium uptake determined using a scintillation counter. Supernatants that stimulated proliferation in two replicates at levels two-fold greater than the proliferation observed in cells cultured in medium alone were considered positive.

Figure 2:
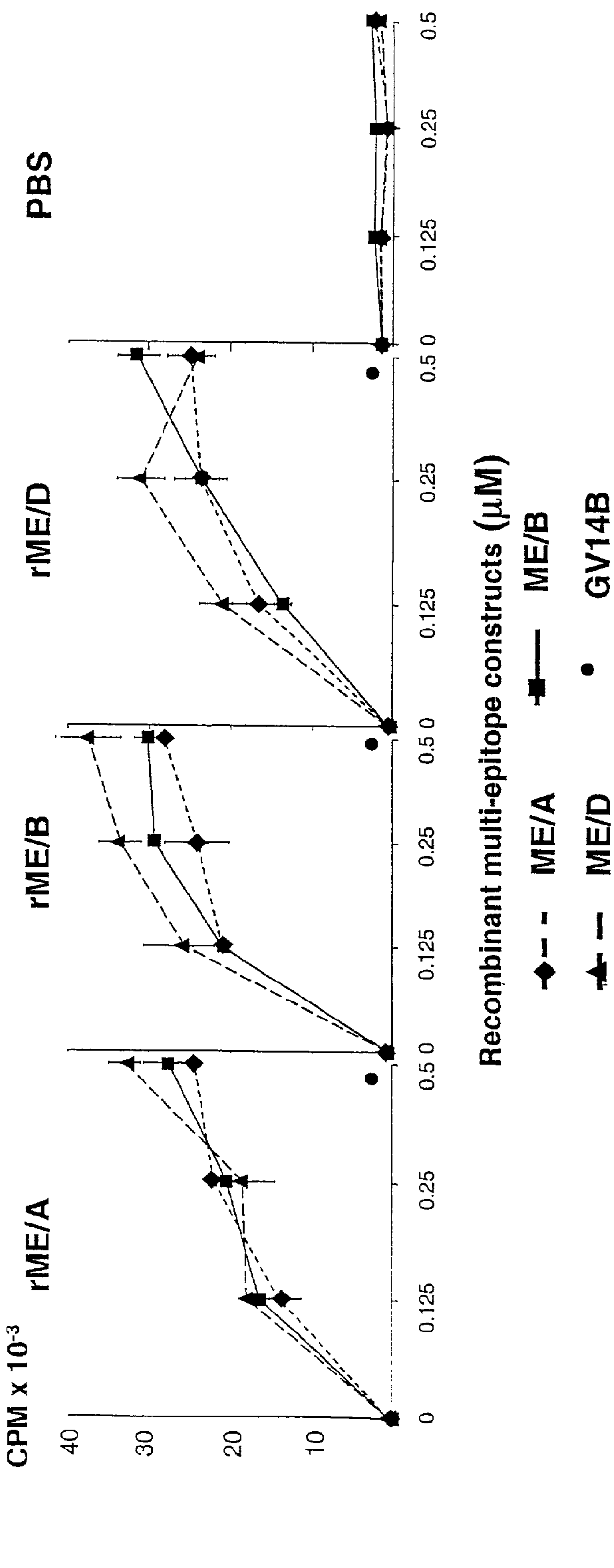
FIGS. 2A–D show the proliferative responses of lymph node cells from BALB/cByJ mice immunized subcutaneously with rME/A (FIG. 2A), rME/B (FIG. 2B) or rME/D (FIG. 2C). Control mice were immunized with PBS (FIG. 2D).

Results from the murine proliferation experiments are shown in FIGS. 2A–D. All three of the recombinant multi-epitope constructs, or fusion proteins, induced a proliferative response in lymph node cells from immunized mice. The levels of proliferation induced by the three recombinant multi-epitope constructs rME/A, rME/B and rME/D (FIGS. 2A, B and C, respectively) were similar, showing that the constructs were antigenically identical. No proliferation was obtained from control mice immunized with PBS (FIG. 2D).

Figure 3:
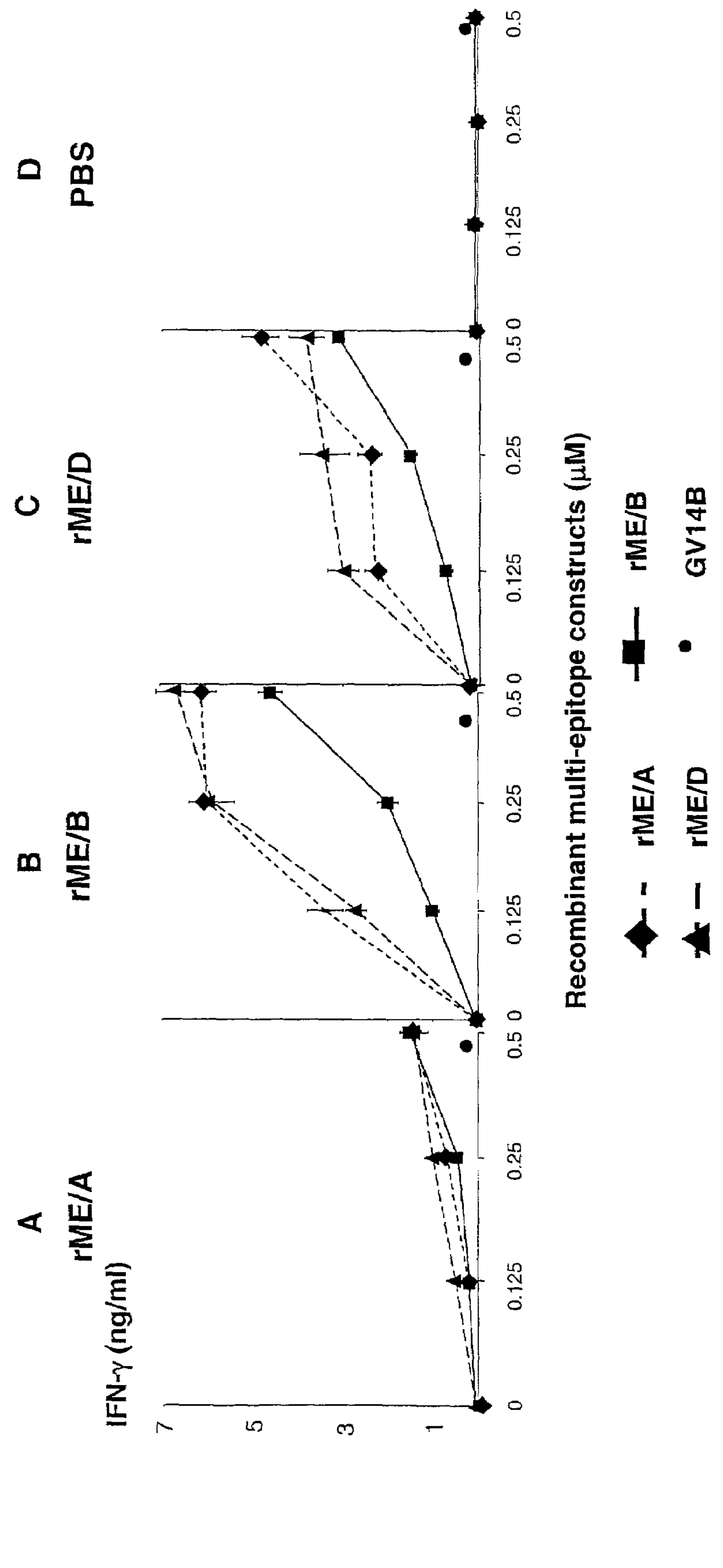
FIGS. 3A–D illustrate IFN-γ secretion by lymph node cells from BALB/cByJ mice immunized subcutaneously with recombinant multi-epitope constructs rME/A (FIG. 3A), rME/B (FIG. 3B) or rME/D (FIG. 3C). Control mice were immunized with PBS (FIG. 3D).

The levels of IFN-γ secreted by stimulated lymph node cells from mice immunized with rME/A, rME/B or rME/D are shown in FIGS. 3A–C, respectively. All three recombinant multi-epitope constructs stimulated IFN-γ secretion by lymph node cells, with the highest levels stimulated with rME/B (FIG. 3B). Cells from control mice stimulated with PBS secreted undetectable amounts of IFN-γ (FIG. 3D). These results indicate that immunization with the multi-epitope constructs induced a Th1 immune response in the mice.

B. Recombinant Multi-Epitope Construct ME/D and ME/D DNA Stimulate Lymph Node and Spleen Cells from Mice Immunized by Different Routes to Proliferate and Secrete IFN-γ in vitro In these experiments, lymph node or spleen cells from mice immunized subcutaneously, intraperitoneally or intramuscularly with the recombinant multi-epitope construct rME/D or the DNA form of the multi-epitope construct ME/D were stimulated to induce T-cell proliferation and IFN-γ production. BALB/cByJ mice were immunized either subcutaneously in each footpad with one dose of 10 μg rME/D in IFA, intraperitoneally with one dose of 50 μg rME/D in IFA, or intramuscularly with three doses at 3 week intervals with 100 μg ME/D DNA. Control mice were immunized with PBS by the three different immunization routes. After nine days, mice immunized by the subcutaneous and intraperitoneal routes were sacrificed and the lymph nodes (subcutaneous immunization) or spleen cells (intraperitoneal immunization) removed. Spleen cells from mice immunized by intramuscular injection were harvested 15 days after the last immunization. Proliferation and IFN-γ production by these cells were determined as described above.

Figure 4:
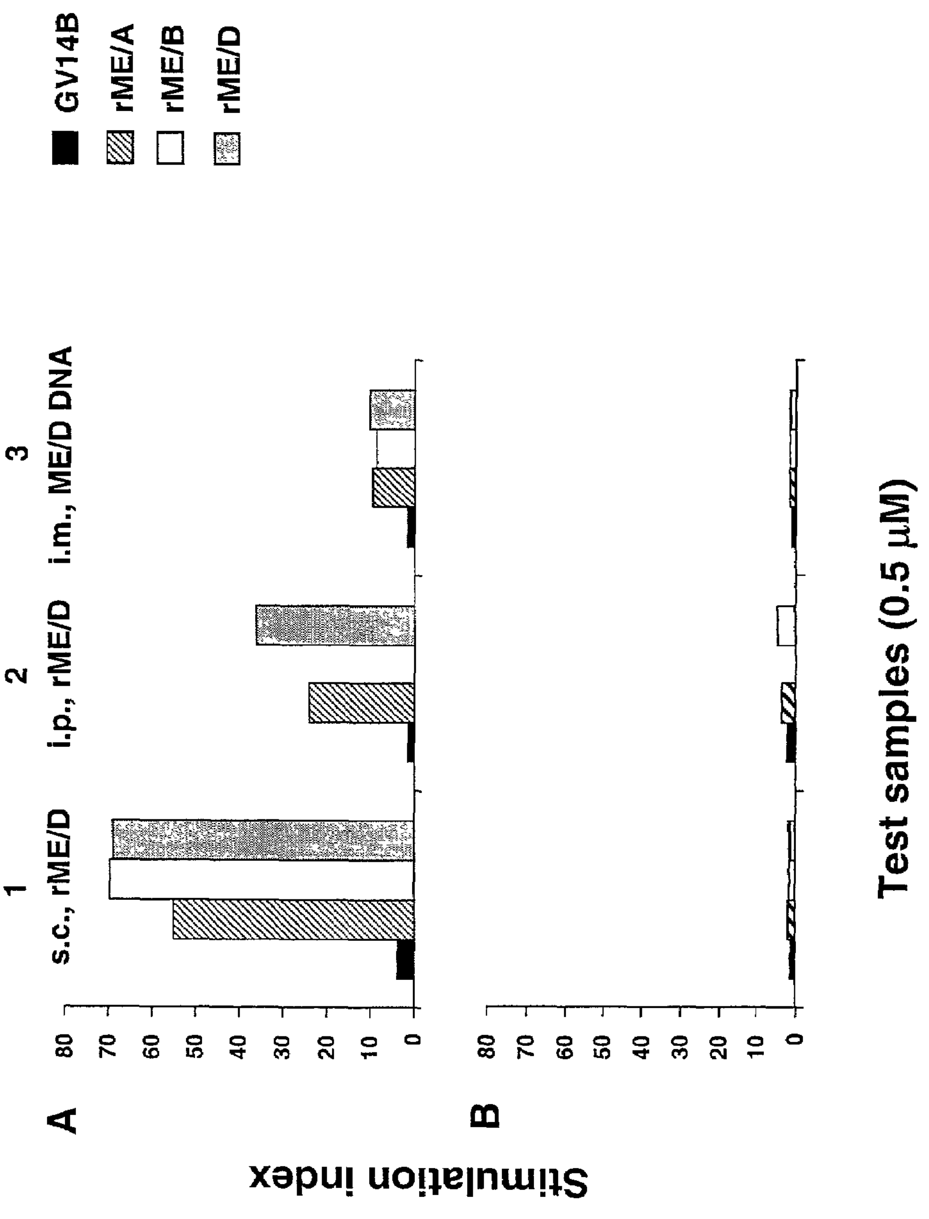
FIG. 4A demonstrates the proliferative responses of lymph node cells from BALB/cByJ mice immunized with rME/A, rME/D or ME/D DNA by three different routes of immunization. The proliferative response of lymph node cells from control mice immunized with PBS is shown in FIG. 4B.
Figure 5:
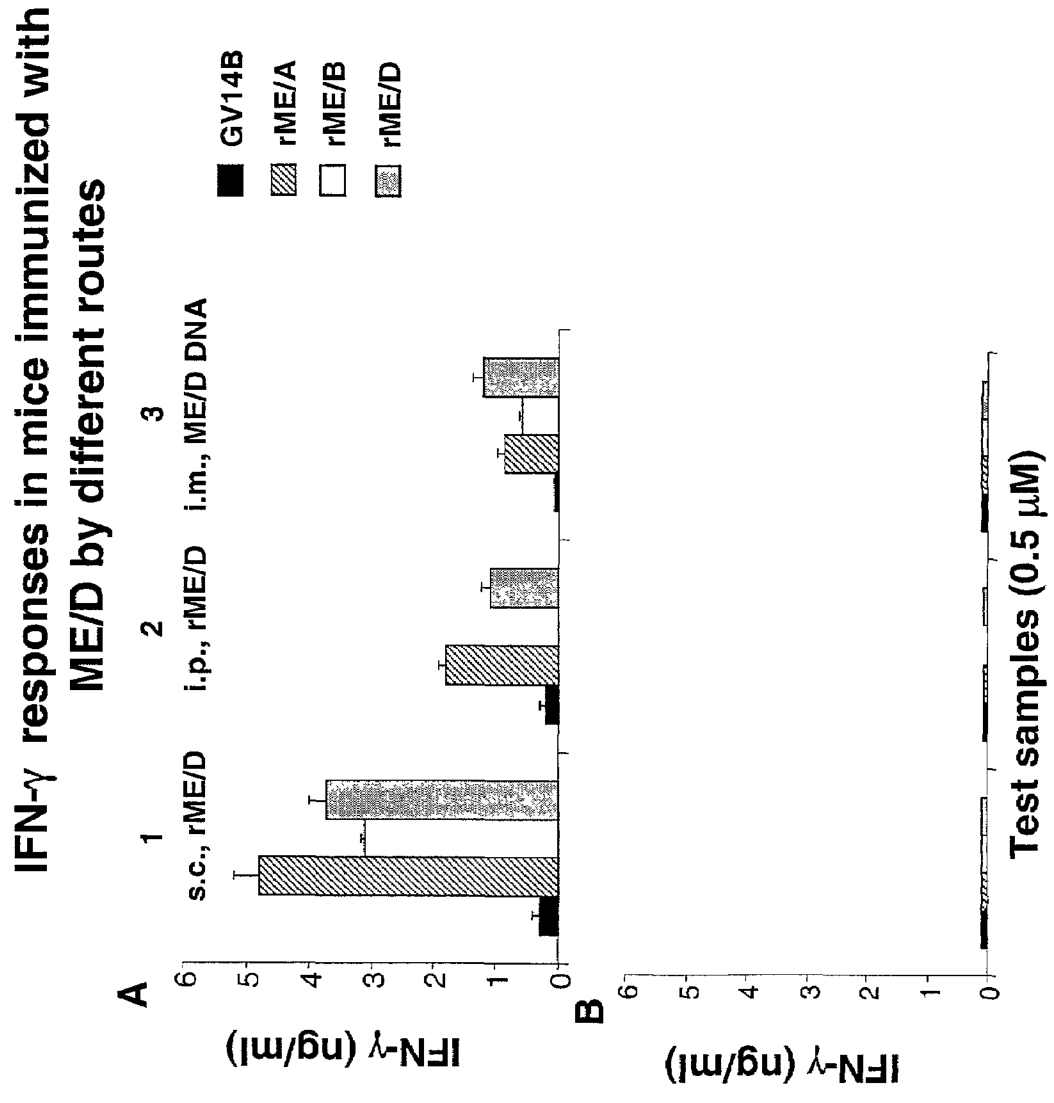
FIG. 5A demonstrates the level of IFN-γ secretion by lymph node cells from BALB/cByJ mice immunized with rME/A, rME/D or ME/D DNA by three different routes of immunization. The level of IFN-γ secretion by control mice immunized with PBS is shown in FIG. 5B.

Results from these experiments are presented in FIG. 4 and FIG. 5. In FIG. 4A, specific proliferative responses by lymph node and spleen cells from mice immunized with rME/D or ME/D DNA are shown. In comparison, FIG. 4B shows the low proliferation by cells from control mice. Similarly, lymph node and spleen cells from mice immunized with rME/D or ME/D DNA were stimulated to secrete IFN-γ (FIG. 5A) while low levels of IFN-γ was secreted by lymph node and spleen cells from control mice immunized with PBS.

Figure 6:
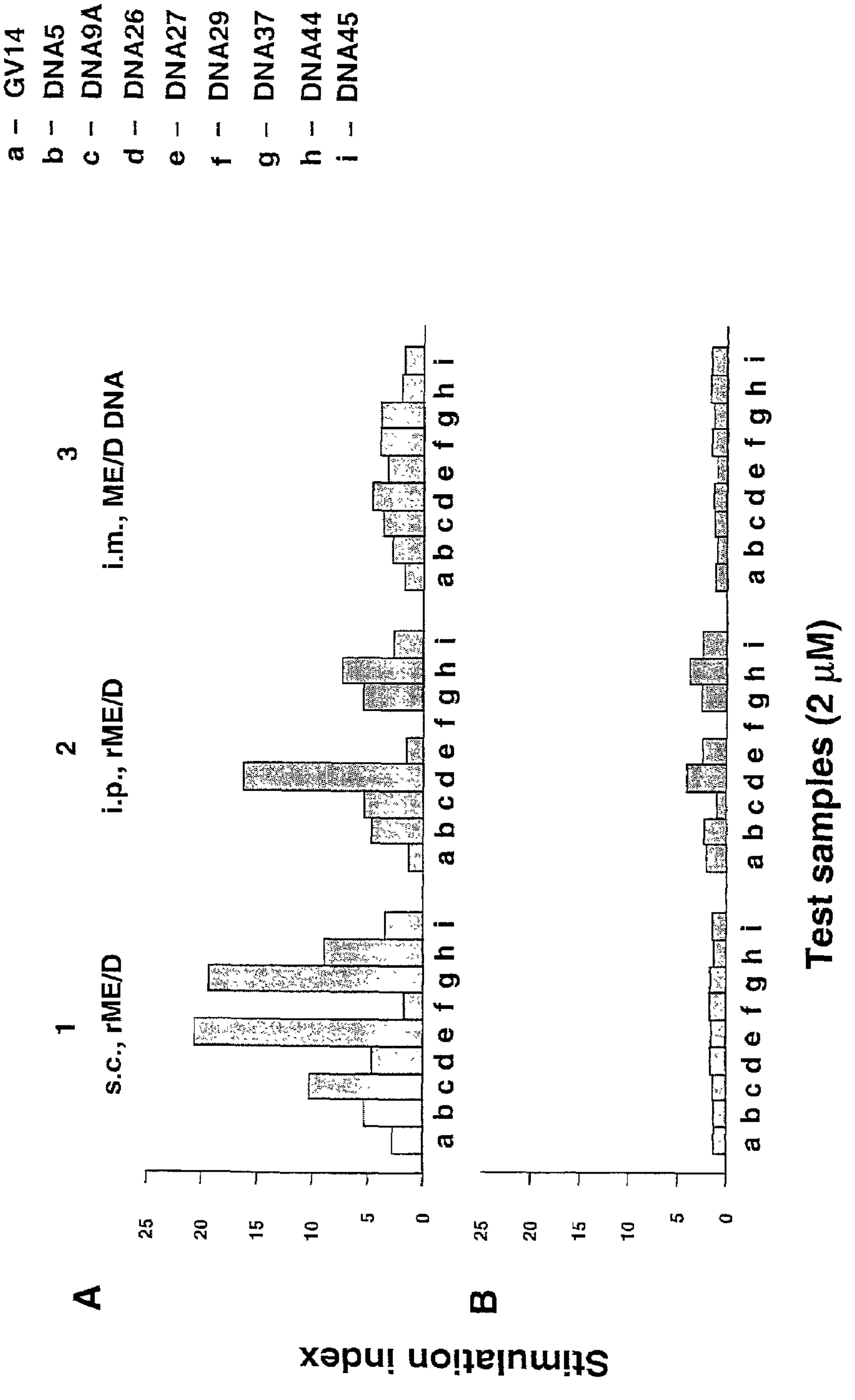
FIG. 6A show the contribution of single epitopes to the proliferative responses of lymph node cells from BALB/cByJ mice immunized with rME/A, rME/D or ME/D DNA by three different routes of immunization. The proliferative response of lymph node cells from control mice immunized with PBS is shown in FIG. 6B.
Figure 7:
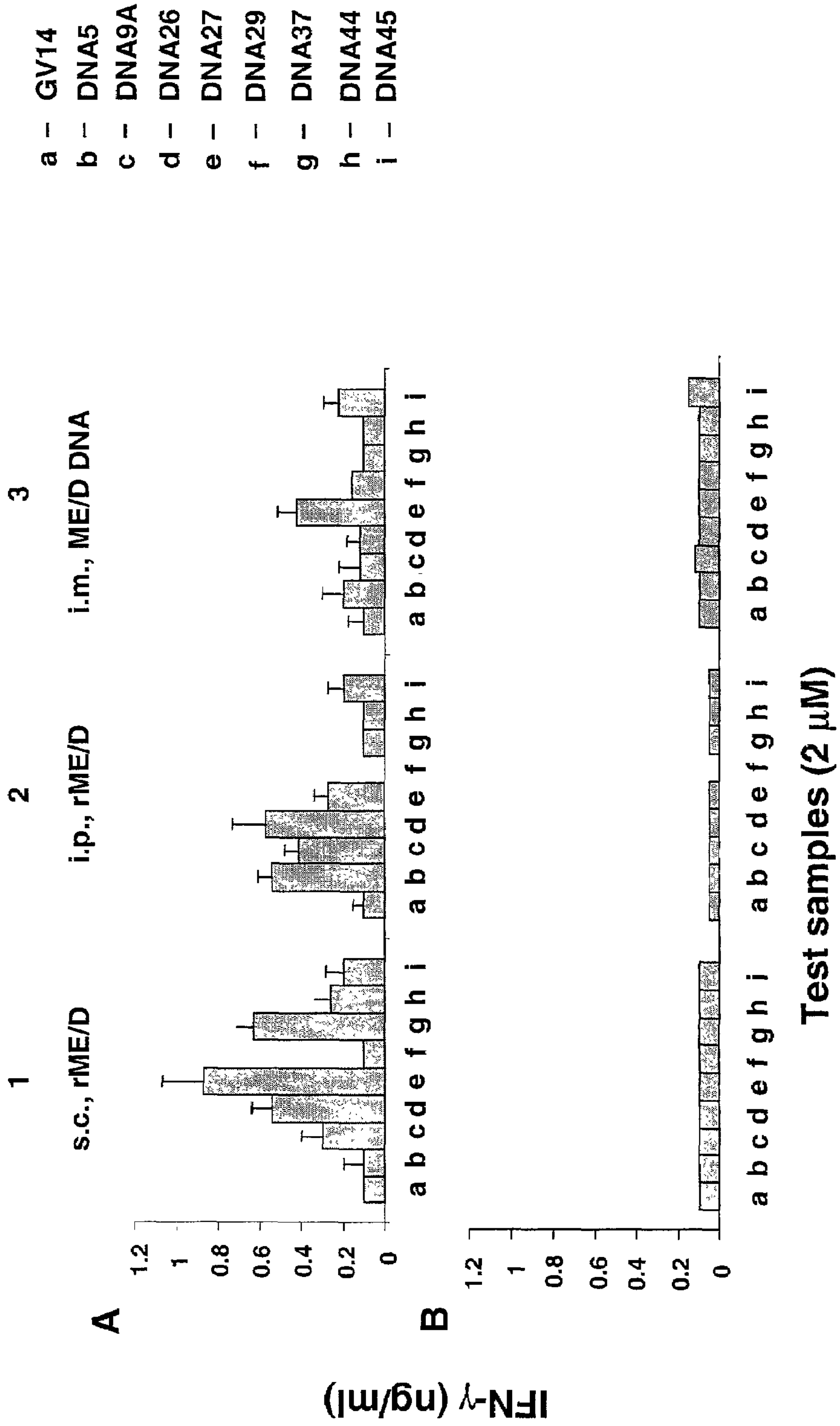
FIG. 7A demonstrates contribution of single epitopes to the level of IFN-γ secretion by lymph node cells from BALB/cByJ mice immunized with rME/A, rME/D or ME/D DNA by three different routes of immunization. The level of IFN-γ secretion by control mice immunized with PBS is shown in FIG. 7B.

C. Single Epitopes from Multi-Epitope Constructs Stimulate Lymph Node and Spleen Cells from Mice Immunized with Recombinant Multi-Epitope Construct rME/D or ME/D DNA by Different Routes to Proliferate and Secrete IFN-γ in vitro In these experiments, lymph node and spleen cells from mice immunized with the recombinant multi-epitope construct rME/D or the DNA form of the multi-epitope construct ME/D by different immunization routes were re-stimulated with the recombinant form of the single epitopes DNA5, DNA9A, DNA26, DNA27, DNA29, DNA37, DNA44 and DNA45. The experimental procedure was the same as outlined above. Results from these experiments are shown in FIGS. 6A–B and FIGS. 7A–B. Specific proliferative responses and IFN-γ secretion were detected in cells re-stimulated with epitopes DNA5, DNA9A, DNA26, DNA37 and DNA44 (FIG. 6A and FIG. 7A). Proliferation and IFN-γ production by epitopes DNA27, DNA29 and DNA45 were shown in at least one immunization group. Low levels of proliferation and IFN-γ production was observed in cells from control mice immunized with PBS (FIG. 6B and FIG. 7B). The data indicates that the epitopes are all individually antigenic when presented to the immune system as part of a multi-component immunogen.

D. Cytokine Production

The cytokine production by spleen cells from mice immunized with the DNA form of the multi-epitope construct ME/D and re-stimulated with rME/A or rME/D was determined as follows. BALB/cByJ mice were immunized intramuscularly with three doses at three week intervals of 100 μg ME/D DNA. Fifteen days after the last injection, mice were sacrificed and the spleen cells removed. The spleen cells were re-stimulated with rME/A, rME/D or the control protein GV14B and the supernatants screened for cytokine production following standard procedures. Cytokine production by the spleen cells is given in Table 6.

TABLE 6

Cytokines secreted by splenocytes from BALB/cByJ mice immunized with ME DNA

| | IL-2* | | | IL-4* | | | IL-6* | | |
|---|---|---|---|---|---|---|---|---|---|
| Plasmid | rME/A | rME/D | GV14B | rME/A | rME/D | GV14B | rME/A | rME/D | GV14B |
| ME/A | 122 | 125 | <50 | 42 | 56 | 39 | 147 | 196 | <30 |
| ME/B | 267 | 200 | <50 | 20 | <10 | <10 | 79 | 56 | <30 |
| ME/D | 96 | 77 | <50 | 13 | <10 | <10 | 131 | 98 | <30 |
| Control | <50 | <50 | <50 | <10 | <10 | <10 | <30 | <30 | <30 |

*Cytokine concentration measured in pg/ml, with a standard error of <10%

As shown in Table 6, IL-2 and IL-6 were secreted by spleen cells of mice stimulated with rME/A and rME/D. IL-2 is a cytokine secreted during a Th1-type immune response, providing further evidence that the multi-epitope constructs elicit a Th1-type immune response. The cytokine IL-6 plays an important role in the immunity of mice to tuberculosis (Ladel et al., *Infect. Imm.* 65: 4843–4849, 1997). No secretion of IL-4, a Th2-type cytokine, was detected.

E. Antibody Production

Figure 8:
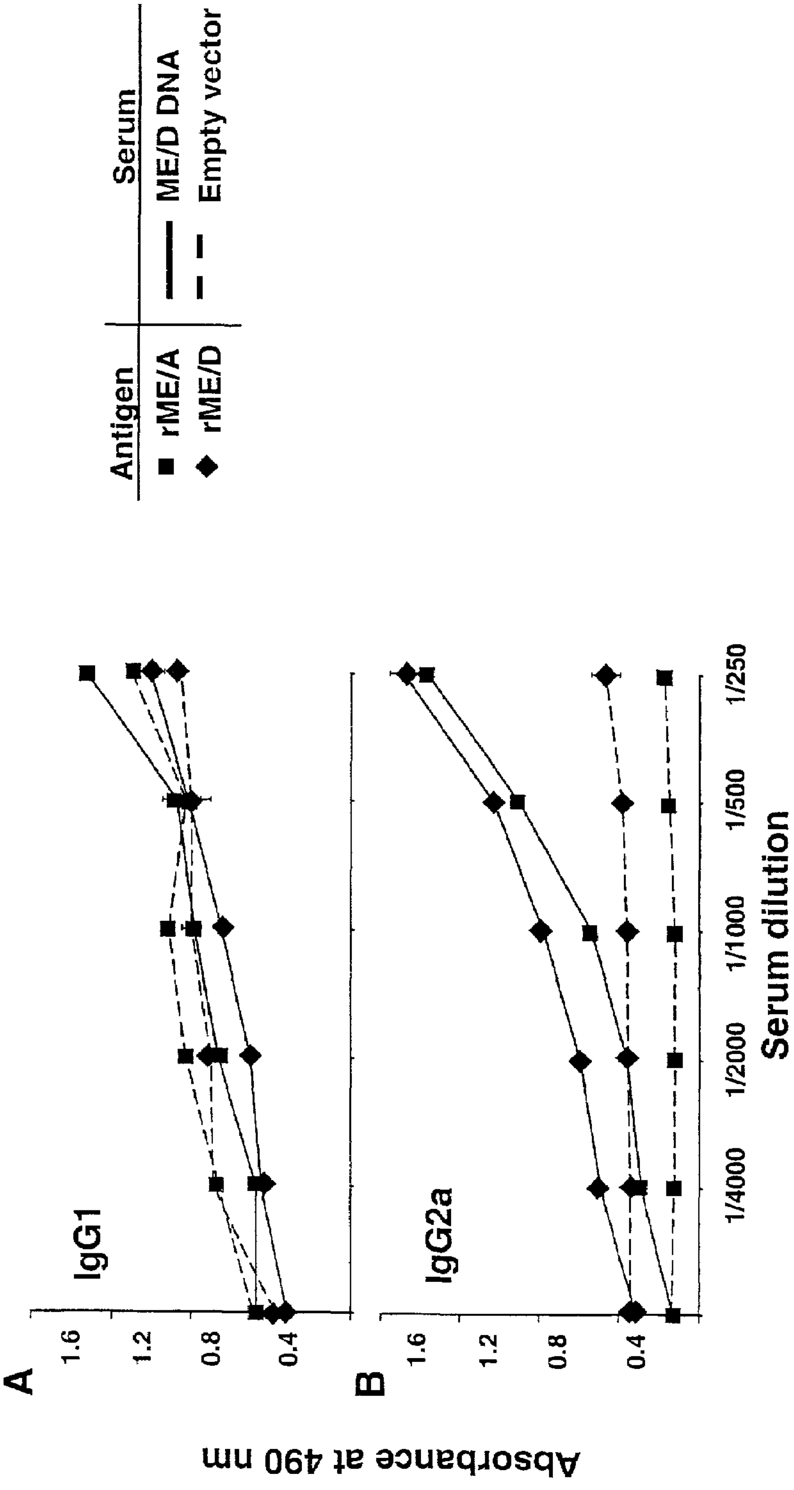
FIGS. 8A and B illustrate the titre and subclass of anti-ME antibodies in the serum of mice immunized with ME/D DNA that reacted with rME/A and rME/D in vitro. The titres of IgG1 antibodies are shown in FIG. 8A, with the titre of IgG2a antibodies being shown in FIG. 8B.

Blood samples from BALB/cByJ mice immunized with ME/D were collected two weeks after the last DNA injection and sera prepared according to standard procedures. The presence of anti-ME/D antibodies was determined by ELISA. As shown in FIG. 8B, high titres of IgG2a antibodies reacting with rME/A and rME/D were detected, but no IgG1 antibodies (FIG. 8A). The presence of IgG2a antibodies is characteristic of a Th1-type immune response.

F. Induction in Mice of Long-Term Memory Responses by Recombinant Epitopes and Recombinant Multi-Epitope Construct rME/D.

Figure 9:
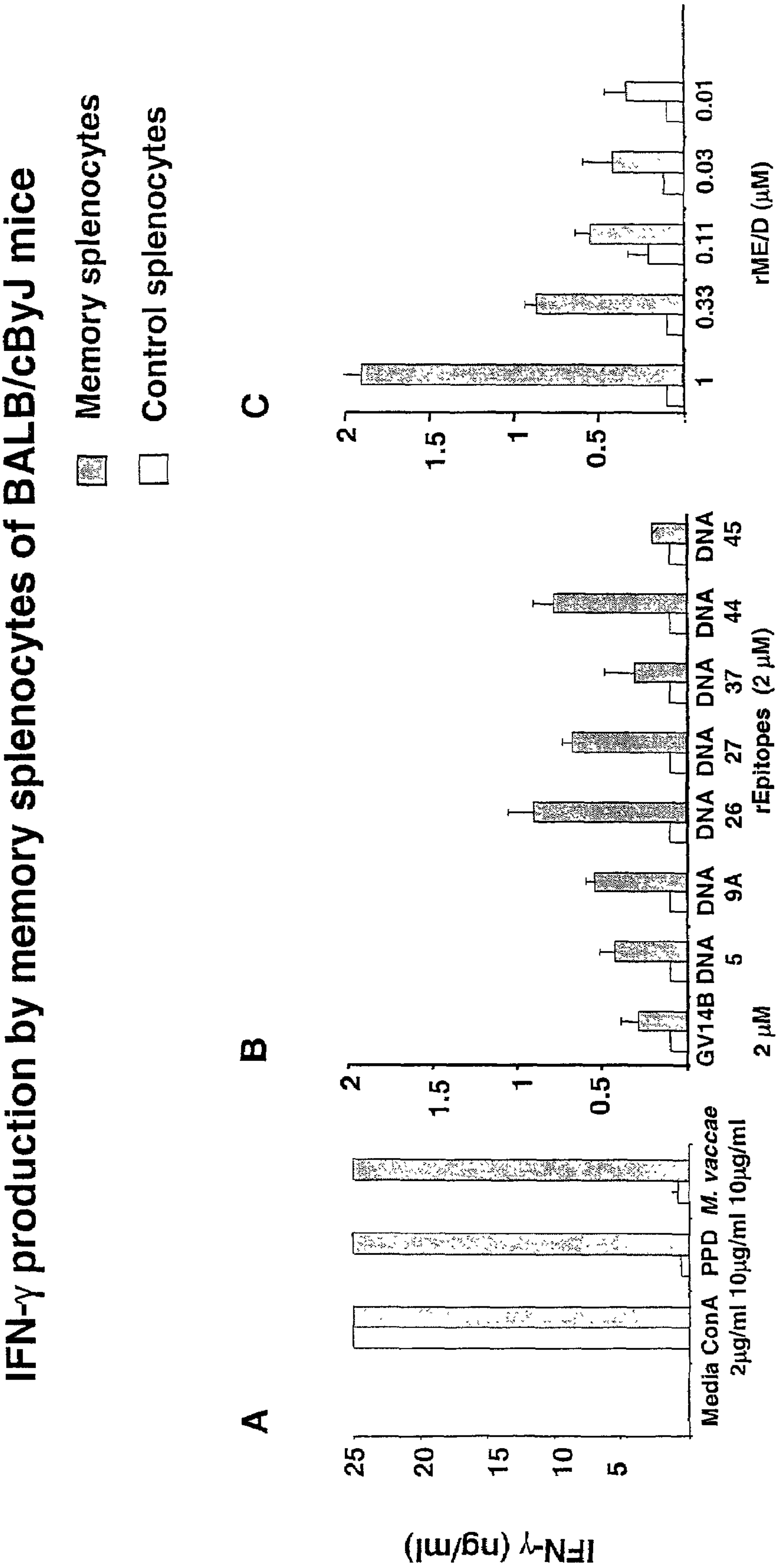
FIGS. 9A–C show the IFN-γ secretion by memory splenocytes from BALB/cByJ mice immunized with recombinant single epitopes (FIG. 9B) or rME/D (FIG. 9C). IFN-γ secretion by splenocytes after stimulation with controls is shown in FIG. 9A.

The induction of long-term memory responses in mice infected with *M. tuberculosis* and immunized with either recombinant single epitopes rDNA5, rDNA9A, rDNA26, rDNA27, rDNA37, rDNA44 or rDNA45, or recombinant multi-epitope construct ME/D was determined as follows. In the mouse long-term memory assay, BALB/cByJ mice were injected with a sub-lethal dose of $10^4$ colony forming units (CFU) of *M. tuberculosis*. After 4 weeks, the mice were treated with antibiotics for a further 4 weeks to cure them of *M. tuberculosis* infection, followed by a resting period of 8 weeks. A second injection of live *M. tuberculosis* ($5\times10^5$ CFU) was given before the immunogenicity of the recombinant constructs was measured three days later using the spleen cell assay described above. Spleen cells were stimulated with 2 μM of recombinant epitope or with 1, 0.33, 0.11, 0.03 or 0.01 μM rME/D. The levels of IFN-γ production determined in the spleen assay are shown in FIGS. 9A–C. Spleen cells from control mice were stimulated with the unrelated protein GV14B (FIG. 9B). Other controls in this experiments included stimulation with medium only, 2 μg/ml ConA, 10 μg/ml PPD and 10 μg/ml *M. vaccae* (FIG. 9A). Recombinant ME/D stimulated memory T cells from mice infected with *M. tuberculosis* to produce large amounts of IFN-γ in a dose-dependent manner (FIG. 9B). The production of IFN-γ in this assay is indicative of the cross-reactivity of ME/D with *M. tuberculosis* antigens that induced long-term immune responses. Antigenic determinants cross-reacting with the *M. tuberculosis* antigens appears to be located on epitopes DNA5, DNA9A, DNA26, DNA27 and DNA44 (FIG. 9B).

epitopes rDNA5, rDNA9A, rDNA26, rDNA27, rDNA29, rDNA37, rDNA44 or rDNA45, or 0.5 μM rME/A or rME/D. Cells in the control groups were stimulated with 2 μM of the protein GV14B or 10 μg/ml PPD. Cytokine responses was measured by ELISA following standard procedures. As shown in Table 7, below, human PBMC stimulated with the recombinant single epitopes, or with rME/A or rME/D produced the Th1 cytokines IFN-γ and TNF-α. These recombinant epitopes also induced secretion of IL-10. No IL-5, a Th2 cytokine, was detected in supernatants of stimulated cells. Low levels of cytokines were secreted in response to stimulation with the control antigen, and all cytokines tested were secreted by human PBMC after stimulation with PPD.

TABLE 7

Cytokine secreted by human PBMC after in vitro stimulation with recombinant single epitopes and rME

| | Recombinant single epitopes | | | | | | | | rME | | Controls | |
|---|---|---|---|---|---|---|---|---|---|---|---|---|
| | DNA | DNA | DNA | DNA | DNA | DNA | DNA | DNA | | | | |
| Cytokine | 5 | 9A | 26 | 27 | 29 | 37 | 44 | 45 | rME/A | rME/D | GV14B | PPD |
| IFN-γ | 4.7 | 2.8 | 4.1 | 0.06 | 3.6 | 4.3 | 0.45 | 0.78. | 4.4 | 3.2 | <0.05 | 3.96 |
| TNF-α | 4.6 | <0.05 | 1.2 | 0.1 | 3.5 | 2.3 | 0.5 | <0.05 | 3.9 | 3.8 | 0.2 | 0.85 |
| IL-10 | 0.75 | <0.05 | 0.9 | 0.15 | 0.98 | 0.83 | 0.59 | <0.05 | 1.17 | 1.12 | 0.07 | 0.34 |
| IL-5 | 0.08 | <0.05 | <0.05 | 0.06 | <0.05 | <0.05 | <0.05 | <0.05 | <0.05 | <0.05 | <0.05 | 0.06 |

EXAMPLE 7

Figure 10:
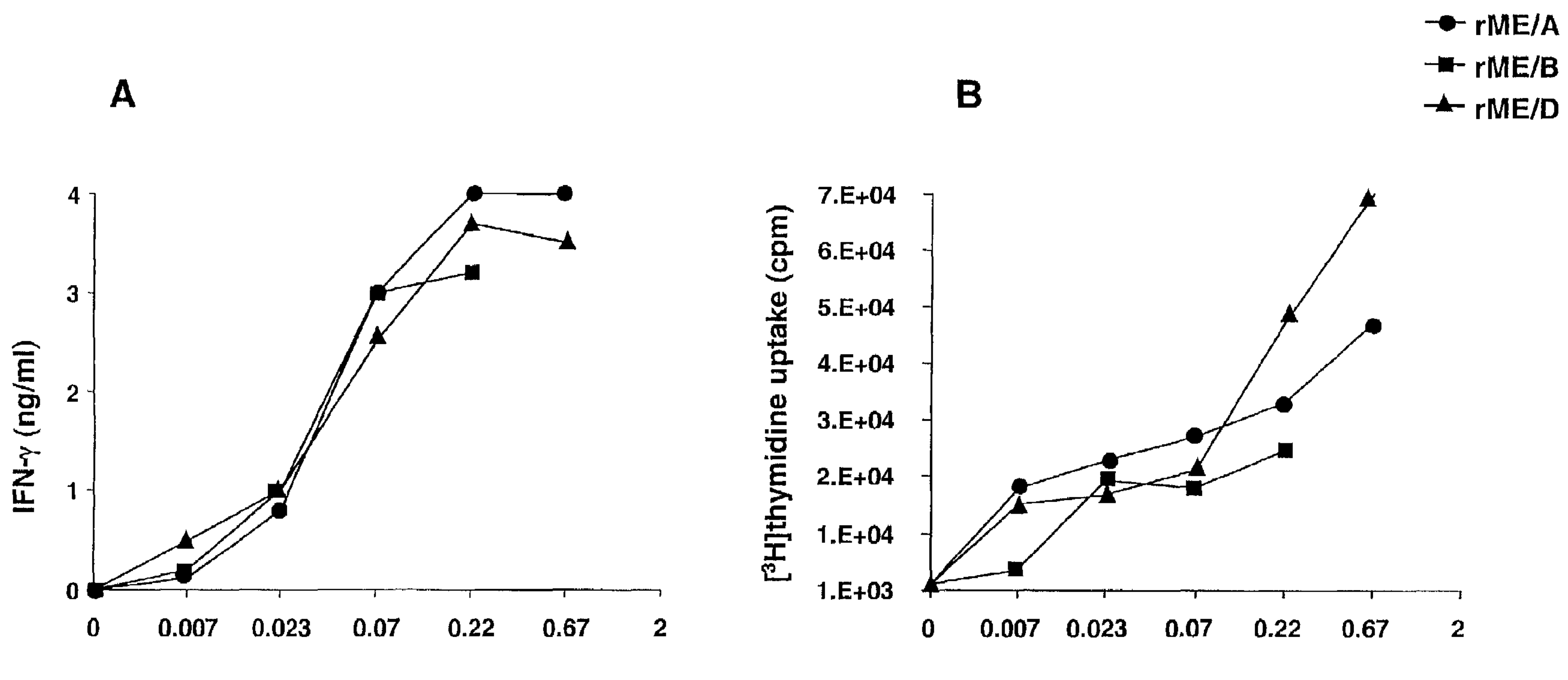
FIGS. 10A and B demonstrate the IFN-γ secretion (FIG. 10A) and proliferative response (FIG. 10B) by human PBMC after stimulation in vitro with rME/A, rME/B or rME/D.
Figure 11:
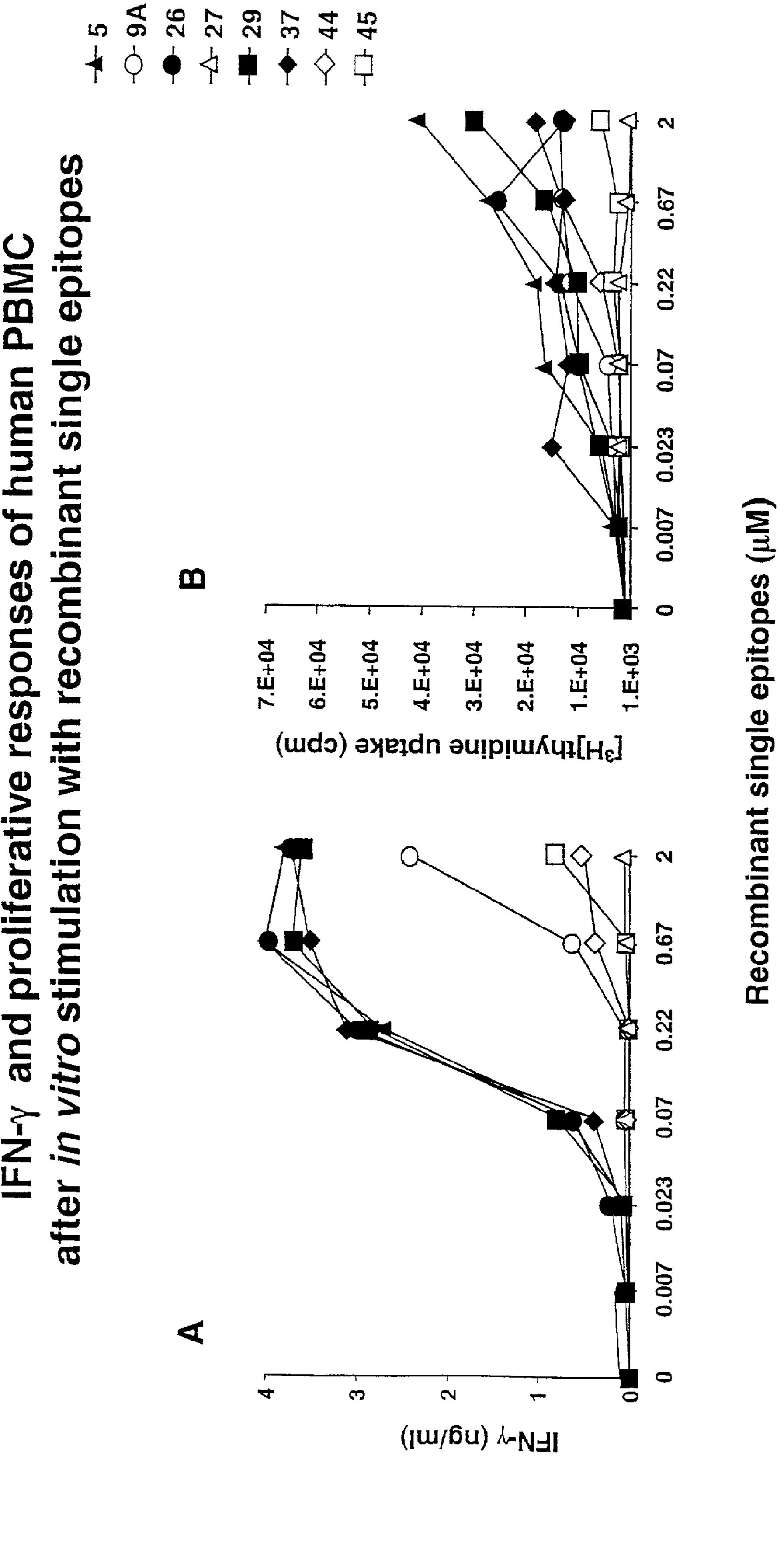
FIGS. 11A and B demonstrate the IFN-γ secretion (FIG. 11A) and proliferative response (FIG. 11B) by human PBMC after stimulation in vitro with eight recombinant single epitopes.

Effect of Stimulation of Human Peripheral Blood Mononuclear Cells (PBMC) with Recombinant Single Epitopes and Recombinant Multi-Epitope Constructs A. Stimulation of Human Peripheral Blood Mononuclear Cells (PBMC) to Proliferate and Secrete Interferon Gamma (IFN-γ) in vitro The recombinant epitopes and recombinant multi-epitope constructs expressed by the pET16 bacterial expression system were cultured with human PBMC at 37° C. After 48 hours, IFN-γ secretion was measured by enzyme-linked immunoassay (ELISA) as described above. Parallel cultures were pulsed with tritiated thymidine and DNA synthesis was used to assess PBMC proliferation. Results of these experiments are shown in FIGS. 10A–B and FIGS. 11A–B. The recombinant multi-epitope constructs stimulated human PBMC to secrete IFN-γ and proliferate (FIGS. 10A and B, respectively). These responses were dose-dependent and of greater magnitude than the responses induced by the individual recombinant epitopes (FIGS. 11A and B).

B. Stimulation of Human PBMC by Recombinant Single Epitopes and Recombinant Multi-Epitope Constructs rME/A and rME/D to Secrete Cytokines in vitro Cytokine production of human PBMC were assessed following in vitro re-stimulation with recombinant single epitopes or recombinant rME/A or rME/D as follows. Cells were stimulated with 2 μM of the recombinant single

EXAMPLE 8

Stimulation of Lymphocyte Proliferation in Cynomolgus Monkeys after Immunization with Recombinant rME/D Three groups each consisting of four cynomolgus monkeys were immunized to test the immunogenicity of the recombinant multi-epitope construct rME/D. Proliferation of lymphotytes was measured in a PBMC proliferation assay. The monkeys in Group I were immunized intradermally with PBS in incomplete Freund's adjuvant (IFA) in a total volume of 0.1 ml. Monkeys in Group II were immunized intradermally with 33 μg rME/D in IFA (total volume 0.1 ml) and monkeys in Group III were immunized intradermally with 10 μg rME/D in IFA (total volume 0.1 ml). Two immunizations were given, at week 0 and week 6. Blood samples were taken from each monkey 12 weeks after immunization.

Whole blood from each monkey was diluted 1:5 and stimulated with control medium (RPMI 1640 supplemented with 10% (v/v) autologous serum, penicillin (60 μg/ml), streptomycin (100 μg/ml), and glutamine (2 mM)) containing either the positive control phytohaemaglutinin (PHA, at 10 μg/ml), PPD (10 μg/ml), *M. vaccae* at 10 μg/ml, rME/D at 1 μg/ml or control recombinant protein GV-14B at 1 μg/ml in a total culture volume of 1 ml. The plates were cultured for 72 hours and then pulsed with 1 μCi/well of tritiated thymidine for a further 18 hours, harvested and tritium uptake determined using a scintillation counter. Lymphocyte proliferation results are shown in Table 8.

TABLE 8

Lymphocyte proliferation in blood samples of cynomolgus monkeys stimulated with PHA, PPD, *M. vaccae*, rME/D or rGV-14B.

| Group | Monkey No. | PHA 10 μ/ml | PPD 10 μ/ml | *M. vaccae* 10 μg/ml | rME/D 1 μg/ml | rGV-14B 1 μg/ml |
|---|---|---|---|---|---|---|
| 1 | 1 | 18* | 1.3 | 0.73 | 1.36 | 0.77 |
| | 2 | 57 | 2.3 | 1.6 | 2.4 | 1.5 |
| | 3 | 32 | 1.6 | 1.5 | 1.6 | 1.0 |
| | 4 | 26 | 2.2 | 1.4 | 1.6 | 0.91 |
| 2 | 1 | 23 | 1.6 | 0.91 | 15 | 0.79 |
| | 2 | 70 | 2.1 | 2.0 | 20 | 2.2 |
| | 3 | 13 | 1.0 | 1.9 | 12 | 2.8 |
| | 4 | 40 | 3.1 | 2.5 | 25 | 3.3 |
| 3 | 1 | 35 | 1.2 | 1.9 | 18 | 2.4 |
| | 2 | 81 | 1.0 | 1.4 | 32 | 2.3 |
| | 3 | 29 | 1.4 | 2.2 | 15 | 1.3 |
| | 4 | 25 | 0.89 | 1.5 | 1.3 | 1.0 |

*Results of PBMC proliferation are expressed as Stimulation Index.

As shown in Table 8, the recombinant multi-epitope construct rME/D induced a proliferative response in PBMC cells from immunized monkeys in Groups II and III comparable to that of the positive control (PHA). No proliferation was recorded after stimulation with PPD, *M. vaccae* or rGV-14B.

EXAMPLE 9

Cloning of Additional *M. Vaccae* Multi-Epitope Constructs

Additional multi-epitope constructs were constructed by cloning the eight different epitopes assayed in Example 4. The epitopes were cloned into the vectors pcDNA3-hGHla/His and pET16 described in Example 1. The different epitopes were amplified using the primers listed in Table 9 and cloned into the vectors using BamHI/XhoI restriction sites for the pcDNA3-hGHls/His constructs and EcoRI/XhoI restriction sites for the pET16 constructs.

The epitopes present in the different constructs are listed in Table 10, as well as the corresponding polynucleotide and polypeptide SEQ ID NOS: of each of the constructs. The epitopes cloned were DNA5 (SEQ ID NO: 13), DNA9A (SEQ ID NO: 14), DNA26 (SEQ ID NO: 15), DNA27 (SEQ ID NO: 16), DNA29 (SEQ ID NO: 17), DNA37 (SEQ ID NO: 18), DNA44 (SEQ ID NO: 20) and DNA45 (SEQ ID NO: 21).

TABLE 9

Primers used to amplify constructs MED1–MED8

| | SEQ ID NOS: of primer pair for modified pET16 vector | | SEQ ID NOS: of primer pair for pcDNA3-hGHla/His vector | |
|---|---|---|---|---|
| Construct | 5' primer SEQ ID NO: | 3' primer SEQ ID NO: | 5' primer SEQ ID NO: | 3' primer SEQ ID NO: |
| MED1 | 112 | 98 | 113 | 98 |
| MED2 | 112 | 99 | 113 | 99 |
| MED3 | 112 | 100 | 113 | 106 |
| MED4 | 112 | 101 | 113 | 107 |
| MED5 | 112 | 102 | 113 | 108 |
| MED6 | 112 | 103 | 113 | 109 |
| MED7 | 112 | 104 | 113 | 110 |
| MED8 | 112 | 105 | 114 | 111 |

TABLE 10

Additional single and multi-epitope constructs

| Polynucleotide SEQ ID NO: | Construct Name | Epitopes in Construct | Polypeptide SEQ ID NO: |
|---|---|---|---|
| 82 | MED1 | DNA9A | 90 |
| 83 | MED2 | DNA9A-DNA44 | 91 |
| 84 | MED3 | DNA9A-DNA44-DNA26 | 92 |
| 85 | MED4 | DNA9A-DNA44-DNA26-DNA45 | 93 |
| 86 | MED5 | DNA9A-DNA44-DNA26-DNA45-DNA37 | 94 |
| 87 | MED6 | DNA9A-DNA44-DNA26-DNA45-DNA37-DNA27 | 95 |
| 88 | MED7 | DNA9A-DNA44-DNA26-DNA45-DNA37-DNA27-DNA29 | 96 |
| 89 | MED8 | DNA9A-DNA44-DNA26-DNA45-DNA37-DNA27-DNA29-DNA5 | 97 |

Although the present invention has been described in some detail by way of illustration and example for purposes of clarity of understanding, changes and modifications can be carried out without departing from the scope of the invention which is intended to be limited only by the scope of the appended claims.

I claim:

1. An isolated polypeptide comprising an amino acid sequence having at least 95% identity to SEQ ID NO: 71, wherein the polypeptide possesses at least one property selected from the group consisting of:

(i) an ability to stimulate proliferation of T cells from individuals exposed to *Mycobacterium tuberculosis*, and (ii) an ability to stimulate interferon-gamma secretion from T cells from individuals exposed to *Mycobacterium tuberculosis.*

2. A composition comprising at least one polypeptide according to claim 1, and at least one component selected from the group consisting of: physiologically acceptable carriers and immunostimulants.

3. A fusion protein comprising at least one polypeptide according to claim 1.

4. A composition comprising at least one fusion protein according to claim 3 and at least one component selected from the group consisting of: physiologically acceptable carriers and immunostimulants.

5. The composition of claim 4, wherein the composition further comprises a flt3 ligand.

* * * * *

SEQUENCE LISTING

```
<160> NUMBER OF SEQ ID NOS: 114

<210> SEQ ID NO 1
<211> LENGTH: 29
```

-continued

<212> TYPE: DNA
<213> ORGANISM: Artificial Sequence
<220> FEATURE:
<223> OTHER INFORMATION: Made in a lab

<400> SEQUENCE: 1
gagagagaaa gcttatggct acaggctcc 29

<210> SEQ ID NO 2
<211> LENGTH: 30
<212> TYPE: DNA
<213> ORGANISM: Artificial Sequence
<220> FEATURE:
<223> OTHER INFORMATION: Made in a lab

<400> SEQUENCE: 2
aaggaagggg atcccgaagc cacagctgcc 30

<210> SEQ ID NO 3
<211> LENGTH: 29
<212> TYPE: DNA
<213> ORGANISM: Artificial Sequence
<220> FEATURE:
<223> OTHER INFORMATION: Made in a lab

<400> SEQUENCE: 3
aaggaagggg atccgaagcc acagctgcc 29

<210> SEQ ID NO 4
<211> LENGTH: 31
<212> TYPE: DNA
<213> ORGANISM: Artificial Sequence
<220> FEATURE:
<223> OTHER INFORMATION: Made in a lab

<400> SEQUENCE: 4
aaggaagggg atcccggaag ccacagctgc c 31

<210> SEQ ID NO 5
<211> LENGTH: 146
<212> TYPE: DNA
<213> ORGANISM: Mycobacterium vaccae

<400> SEQUENCE: 5
aagcttatgg ctacaggctc ccggacgtcc ctgctcctgg cttttggcct gctctgcctg 60
ccctggcttc aagagggcag tgccttccca accattccct tatccaggct ttttgacaac 120
gctatgcagc tgtggcttcg ggatcc 146

<210> SEQ ID NO 6
<211> LENGTH: 145
<212> TYPE: DNA
<213> ORGANISM: Mycobacterium vaccae

<400> SEQUENCE: 6
aagcttatgg ctacaggctc ccggacgtcc ctgctcctgg cttttggcct gctctgcctg 60
ccctggcttc aagagggcag tgccttccca accattccct tatccaggct ttttgacaac 120
gctatgcagc tgtggcttcg gatcc 145

<210> SEQ ID NO 7
<211> LENGTH: 147
<212> TYPE: DNA
<213> ORGANISM: Mycobacterium vaccae -continued

<400> SEQUENCE: 7
aagcttatgg ctacaggctc ccggacgtcc ctgctcctgg cttttggcct gctctgcctg 60
ccctggcttc aagagggcag tgccttccca accattccct tatccaggct ttttgacaac 120
gctatgcagc tgtggcttcc gggatcc 147

<210> SEQ ID NO 8
<211> LENGTH: 39
<212> TYPE: DNA
<213> ORGANISM: Mycobacterium vaccae

<400> SEQUENCE: 8
atcgccgcca ccggcccggt gcccggcacc gcgtggatc 39

<210> SEQ ID NO 9
<211> LENGTH: 96
<212> TYPE: DNA
<213> ORGANISM: Mycobacterium vaccae

<400> SEQUENCE: 9
gttcgtcagt acccgaagct cttgagagct aaggccaatt gggaagatac ttggaccttc 60
ccatcaatag aggaaaagca tcgccctagg ggatcc 96

<210> SEQ ID NO 10
<211> LENGTH: 75
<212> TYPE: DNA
<213> ORGANISM: Mycobacterium vaccae

<400> SEQUENCE: 10
gtagcgggcc cggtgtttcg agtgaacttg ggcagggcaa tcccatcgcg cgcagcccgc 60
gcagcggaaa tccac 75

<210> SEQ ID NO 11
<211> LENGTH: 114
<212> TYPE: DNA
<213> ORGANISM: Mycobacterium vaccae

<400> SEQUENCE: 11
atcacgcagg taggccgtcc agccgtactc ttcgccccag aacagcggtg ccgtcgccgc 60
gcagaccagc ggtcctgccg ccagatacac ccaggcggtg gccggcatgt ccag 114

<210> SEQ ID NO 12
<211> LENGTH: 33
<212> TYPE: DNA
<213> ORGANISM: Mycobacterium vaccae

<400> SEQUENCE: 12
atcgtggcca gcgcgcgcgg cacggtggag atc 33

<210> SEQ ID NO 13
<211> LENGTH: 210
<212> TYPE: DNA
<213> ORGANISM: Mycobacterium vaccae

<400> SEQUENCE: 13
atcgccgcca ccggcccggt gcccggcacc gcgtggatcg ttcgtcagta cccgaagctc 60
ttgagagcta aggccaattg ggaagatact tggaccttcc catcaataga ggaaaagcat 120
cgccctaggg gatccgtagc gggcccggtg tttcgagtga acttgggcag ggcaatccca 180
tcgcgcgcag cccgcgcagc ggaaatccac 210

-continued

```
<210> SEQ ID NO 14
<211> LENGTH: 697
<212> TYPE: DNA
<213> ORGANISM: Mycobacterium vaccae

<400> SEQUENCE: 14

atctactcga ccttcgccga ccgggcgtac ccgggtggcc tgacgtactc cggccatccg     60

ctggcgaccg cctgcgcggt cgcgacgatc aacgcgatgg aagacgaagg catggtggcc    120

aacgctgccc gcatcggcga gcaggtgctc ggaccgggtc tgcgcgatct cgccgcccgg    180

caccgttcgg tcggcgaagt ccgcggcctc ggcgtcttct gggcggatct cggtgaggtc    240

gtcctgcggc gactggaatg ccacgttgtt gacgacgatg tccagtccgc caagctgttt    300

caccgtgtcc tcgaccaccg cgcggcagtg cgccggctcg gccaggtcgc cgggcaggcg    360

gaccgcccgc tgtccggcct cttcgatcag tgccagcgca tcccgaaccg cggcggcgta    420

cgcgtcggcg tcggcgccgc gcacggccgg gcacggggcc acctcccgct ccgggcaggc    480

gggtccgtgg accgcagcac ggccgagtcg tttggtacag gtgcgcaccc cgctgaaccg    540

ggccatcagc gccgccgcct cggtcgcgtc gctgcgggac cggaacgggc ccaccgcgct    600

gtcggtgcgc ggcgtgcgga cggtggagaa ccgggggaag ggttcgtcgg tcagcgtcac    660

ccaccaccac cggtgcggga acttcgaccg ccggttg                             697


<210> SEQ ID NO 15
<211> LENGTH: 291
<212> TYPE: DNA
<213> ORGANISM: Mycobacterium vaccae

<400> SEQUENCE: 15

atcagttcgg ccctggtcgc cagcccgccg agggcagcca gttccgctcc ggcgtcgatc     60

gggttgggtc cgtccggcca gcacaccagc atccacccga ggtcgagcaa cgggtccccg    120

acggtgcaca tctcccagtc gatgaacgcc gcgagctcgg ggacgtcgcg gcgcagcagc    180

acgttgttca gatggcagtc gccgtgcatg atcccgggtt cggcgtcgtc gggcctgcgc    240

gagtccagcc agtcggcgag cacatgcacc gacgggaacg actcgggcgc g             291


<210> SEQ ID NO 16
<211> LENGTH: 147
<212> TYPE: DNA
<213> ORGANISM: Mycobacterium vaccae

<400> SEQUENCE: 16

atcacgcagg taggccgtcc agccgtactc ttcgccccag aacagcggtg ccgtcgccgc     60

gcagaccagc ggtcctgccg ccagatacac ccaggcggtg gccggcatgt ccagatcgtg    120

gccagcgcgc gcggcacggt ggagatc                                        147


<210> SEQ ID NO 17
<211> LENGTH: 138
<212> TYPE: DNA
<213> ORGANISM: Mycobacterium vaccae

<400> SEQUENCE: 17

atcgcgcggc tgtgcgggaa ggacgaggcc gtagcggcgt tgcactacgt cgccccggtt     60

ggcgagaagc aggactacat cgaccgagcc ttgcgcaaca tcgggccgta tctgccagct    120

gaggttcccg ctctcgtc                                                  138
```

-continued

<210> SEQ ID NO 18
<211> LENGTH: 261
<212> TYPE: DNA
<213> ORGANISM: Mycobacterium vaccae

<400> SEQUENCE: 18
gatcggcagg catcacgaac agtaagcggt gttccggttg aatccaatgt gctgtcagca 60
ggcatccgat gccgaacacc gaccacgcga gcagtcgcaa tctgtctcgc gaccctggcg 120
tcacgcggcg tcgtggctcc gcaacccgcc ggcgatgtcg cgcgcgccgc tgcggccggc 180
tctccatggc cggttcgttc agtcgctcgt ccggtggctg ttctgcgaac gggcccgccg 240
ccccgtcgtc cgtccgatac g 261

<210> SEQ ID NO 19
<211> LENGTH: 279
<212> TYPE: DNA
<213> ORGANISM: Mycobacterium vaccae

<400> SEQUENCE: 19
gatctcgttg cgcgtccgcg agatctgcga ccggtacgac ctgccctaca ccaccgggtc 60
cttcctggcg cagtacggca agtcgtggcg cacgatcgcg aaactgtcgc tgccggacaa 120
gttcctgcgc gacaccgccg acgacgcccc ggagacccgc agcgagcgga tgttcgccga 180
actggatccg tcggagcggc gcgggctgaa gtcggccatc gccgcggtgc ggtcgcgccg 240
gcgcgccaag gtcgctgcga aagccgcgaa gatcgcgat 279

<210> SEQ ID NO 20
<211> LENGTH: 132
<212> TYPE: DNA
<213> ORGANISM: Mycobacterium vaccae

<400> SEQUENCE: 20
gatccagaac gggccggtct gcgggttgag gtcctcggtg cccagtgccg tcgacgcgac 60
gtcgtcggcg ctggtgatgc ggccgccgta ggcgtcctcg gtccacaacg tcagcaccgt 120
gcccgggcgg at 132

<210> SEQ ID NO 21
<211> LENGTH: 177
<212> TYPE: DNA
<213> ORGANISM: Mycobacterium vaccae

<400> SEQUENCE: 21
gatcagctcg gggagccggg tgcccagcaa cgccagcgtg ggaagcaccg agaccggcgc 60
gatgtgcccg cgcagcagcg cccagccgtg caccccgcgg gaccgggccc cgcggaccgc 120
gtcggagtcg accccggccg ccaccgccgc gcgcgtggtc agcatcagcc acgggat 177

<210> SEQ ID NO 22
<211> LENGTH: 15
<212> TYPE: DNA
<213> ORGANISM: Artificial Sequence
<220> FEATURE:
<223> OTHER INFORMATION: Made in a lab

<400> SEQUENCE: 22
cgcagctgtg gcttc 15

<210> SEQ ID NO 23
<211> LENGTH: 22

-continued

<212> TYPE: DNA
<213> ORGANISM: Artificial Sequence
<220> FEATURE:
<223> OTHER INFORMATION: Made in a lab

<400> SEQUENCE: 23
ttacttaggt tactagtgga tc 22

<210> SEQ ID NO 24
<211> LENGTH: 23
<212> TYPE: DNA
<213> ORGANISM: Artificial Sequence
<220> FEATURE:
<223> OTHER INFORMATION: Made in a lab

<400> SEQUENCE: 24
cgatctactc gaccttcgcc gac 23

<210> SEQ ID NO 25
<211> LENGTH: 24
<212> TYPE: DNA
<213> ORGANISM: Artificial Sequence
<220> FEATURE:
<223> OTHER INFORMATION: Made in a lab

<400> SEQUENCE: 25
ttacgcccag aagacgccga ggcc 24

<210> SEQ ID NO 26
<211> LENGTH: 26
<212> TYPE: DNA
<213> ORGANISM: Artificial Sequence
<220> FEATURE:
<223> OTHER INFORMATION: Made in a lab

<400> SEQUENCE: 26
gatcccatca ccatcaccat cactga 26

<210> SEQ ID NO 27
<211> LENGTH: 26
<212> TYPE: DNA
<213> ORGANISM: Artificial Sequence
<220> FEATURE:
<223> OTHER INFORMATION: Made in a lab

<400> SEQUENCE: 27
ggtagtggta gtggtagtga ctttaa 26

<210> SEQ ID NO 28
<211> LENGTH: 20
<212> TYPE: DNA
<213> ORGANISM: Artificial Sequence
<220> FEATURE:
<223> OTHER INFORMATION: Made in a lab

<400> SEQUENCE: 28
atggctacag gctcccggac 20

<210> SEQ ID NO 29
<211> LENGTH: 34
<212> TYPE: DNA
<213> ORGANISM: Artificial Sequence
<220> FEATURE:
<223> OTHER INFORMATION: Made in a lab

<400> SEQUENCE: 29

-continued gagagagaga tctgtggatt tccgctgcgc gggc 34

<210> SEQ ID NO 30
<211> LENGTH: 34
<212> TYPE: DNA
<213> ORGANISM: Artificial Sequence
<220> FEATURE:
<223> OTHER INFORMATION: Made in a lab

<400> SEQUENCE: 30
gagagagaga tctcgcgccc gagtcgttcc cgtc 34

<210> SEQ ID NO 31
<211> LENGTH: 34
<212> TYPE: DNA
<213> ORGANISM: Artificial Sequence
<220> FEATURE:
<223> OTHER INFORMATION: Made in a lab

<400> SEQUENCE: 31
gagagagaga tctgatctcc accgtgccgc gcgc 34

<210> SEQ ID NO 32
<211> LENGTH: 34
<212> TYPE: DNA
<213> ORGANISM: Artificial Sequence
<220> FEATURE:
<223> OTHER INFORMATION: Made in a lab

<400> SEQUENCE: 32
gagagagaga tctgacgaga gcgggaacct cagc 34

<210> SEQ ID NO 33
<211> LENGTH: 34
<212> TYPE: DNA
<213> ORGANISM: Artificial Sequence
<220> FEATURE:
<223> OTHER INFORMATION: Made in a lab

<400> SEQUENCE: 33
gagagagaga tctatcgcga tcttcgcggc tttc 34

<210> SEQ ID NO 34
<211> LENGTH: 34
<212> TYPE: DNA
<213> ORGANISM: Artificial Sequence
<220> FEATURE:
<223> OTHER INFORMATION: Made in a lab

<400> SEQUENCE: 34
gagagagaga tctatccgcc cgggcacggt gctg 34

<210> SEQ ID NO 35
<211> LENGTH: 34
<212> TYPE: DNA
<213> ORGANISM: Artificial Sequence
<220> FEATURE:
<223> OTHER INFORMATION: Made in a lab

<400> SEQUENCE: 35
gagagagaga tctatcccgt ggctgatgct gacc 34

<210> SEQ ID NO 36
<211> LENGTH: 36
<212> TYPE: DNA
<213> ORGANISM: Artificial Sequence -continued
<220> FEATURE:
<223> OTHER INFORMATION: Made in a lab

<400> SEQUENCE: 36
gagagagaga tctcgtatcg gacggacgac gggacg 36

<210> SEQ ID NO 37
<211> LENGTH: 35
<212> TYPE: DNA
<213> ORGANISM: Artificial Sequence
<220> FEATURE:
<223> OTHER INFORMATION: Made in a lab

<400> SEQUENCE: 37
gagagagagg atcccaaccg gcggtcgaag ttccc 35

<210> SEQ ID NO 38
<211> LENGTH: 36
<212> TYPE: DNA
<213> ORGANISM: Artificial Sequence
<220> FEATURE:
<223> OTHER INFORMATION: Made in a lab

<400> SEQUENCE: 38
aaggaaggaa aaggatccgg gaatggttgg gaaggc 36

<210> SEQ ID NO 39
<211> LENGTH: 126
<212> TYPE: DNA
<213> ORGANISM: Artificial Sequence
<220> FEATURE:
<223> OTHER INFORMATION: Made in a lab

<400> SEQUENCE: 39
aagcttatgg ctacaggctc ccggacgtcc ctgctcctgg cttttggcct gctctgcctg 60
ccctggcttc aagagggcag tgccttccca accattcccg gatcccacca tcatcaccat 120
cactga 126

<210> SEQ ID NO 40
<211> LENGTH: 35
<212> TYPE: DNA
<213> ORGANISM: Artificial Sequence
<220> FEATURE:
<223> OTHER INFORMATION: Made in a lab

<400> SEQUENCE: 40
gagagagaga tctatctact cgaccttcgc cgacc 35

<210> SEQ ID NO 41
<211> LENGTH: 37
<212> TYPE: DNA
<213> ORGANISM: Artificial Sequence
<220> FEATURE:
<223> OTHER INFORMATION: Made in a lab

<400> SEQUENCE: 41
aaggaaggaa ggatcccgcc cagaagacgc cgaggcc 37

<210> SEQ ID NO 42
<211> LENGTH: 34
<212> TYPE: DNA
<213> ORGANISM: Artificial Sequence
<220> FEATURE:
<223> OTHER INFORMATION: Made in a lab -continued

<400> SEQUENCE: 42
gagagagaga tctatcagtt cggccctggt cgcc 34

<210> SEQ ID NO 43
<211> LENGTH: 37
<212> TYPE: DNA
<213> ORGANISM: Artificial Sequence
<220> FEATURE:
<223> OTHER INFORMATION: Made in a lab

<400> SEQUENCE: 43
aaggaaggaa ggatcccgcg cccgagtcgt tcccgtc 37

<210> SEQ ID NO 44
<211> LENGTH: 35
<212> TYPE: DNA
<213> ORGANISM: Artificial Sequence
<220> FEATURE:
<223> OTHER INFORMATION: Made in a lab

<400> SEQUENCE: 44
gagagagaga tctgatcggc aggcatcacg aacag 35

<210> SEQ ID NO 45
<211> LENGTH: 37
<212> TYPE: DNA
<213> ORGANISM: Artificial Sequence
<220> FEATURE:
<223> OTHER INFORMATION: Made in a lab

<400> SEQUENCE: 45
aaggaaggaa ggatcccgta tcggacggac gacgggg 37

<210> SEQ ID NO 46
<211> LENGTH: 34
<212> TYPE: DNA
<213> ORGANISM: Artificial Sequence
<220> FEATURE:
<223> OTHER INFORMATION: Made in a lab

<400> SEQUENCE: 46
gagagagaga tctgatccag aacgggccgg tctg 34

<210> SEQ ID NO 47
<211> LENGTH: 37
<212> TYPE: DNA
<213> ORGANISM: Artificial Sequence
<220> FEATURE:
<223> OTHER INFORMATION: Made in a lab

<400> SEQUENCE: 47
aaggaaggaa ggatccatcc gcccgggcac ggtgctg 37

<210> SEQ ID NO 48
<211> LENGTH: 35
<212> TYPE: DNA
<213> ORGANISM: Artificial Sequence
<220> FEATURE:
<223> OTHER INFORMATION: Made in a lab

<400> SEQUENCE: 48
gagagagaga tctgatcagc tcggggagcc gggtg 35

<210> SEQ ID NO 49
<211> LENGTH: 37

-continued

<212> TYPE: DNA
<213> ORGANISM: Artificial Sequence
<220> FEATURE:
<223> OTHER INFORMATION: Made in a lab

<400> SEQUENCE: 49
aaggaaggaa ggatccatcc cgtggctgat gctgacc 37

<210> SEQ ID NO 50
<211> LENGTH: 22
<212> TYPE: DNA
<213> ORGANISM: Artificial Sequence
<220> FEATURE:
<223> OTHER INFORMATION: Made in a lab

<400> SEQUENCE: 50
tatcgccgcc accggcccgg tg 22

<210> SEQ ID NO 51
<211> LENGTH: 22
<212> TYPE: DNA
<213> ORGANISM: Artificial Sequence
<220> FEATURE:
<223> OTHER INFORMATION: Made in a lab

<400> SEQUENCE: 51
cgtggatttc cgctgcgcgg gc 22

<210> SEQ ID NO 52
<211> LENGTH: 33
<212> TYPE: DNA
<213> ORGANISM: Artificial Sequence
<220> FEATURE:
<223> OTHER INFORMATION: Made in a lab

<400> SEQUENCE: 52
gagagagaga tctatcacgc aggtaggccg tcc 33

<210> SEQ ID NO 53
<211> LENGTH: 37
<212> TYPE: DNA
<213> ORGANISM: Artificial Sequence
<220> FEATURE:
<223> OTHER INFORMATION: Made in a lab

<400> SEQUENCE: 53
aaggaaggaa ggatccgatc tccaccgtgc cgcgcgc 37

<210> SEQ ID NO 54
<211> LENGTH: 35
<212> TYPE: DNA
<213> ORGANISM: Artificial Sequence
<220> FEATURE:
<223> OTHER INFORMATION: Made in a lab

<400> SEQUENCE: 54
gagagagaga tctatcgcgc ggctgtgcgg gaagg 35

<210> SEQ ID NO 55
<211> LENGTH: 37
<212> TYPE: DNA
<213> ORGANISM: Artificial Sequence
<220> FEATURE:
<223> OTHER INFORMATION: Made in a lab

<400> SEQUENCE: 55

-continued aaggaaggaa ggatccgacg agagcgggaa cctcagc 37

<210> SEQ ID NO 56
<211> LENGTH: 1749
<212> TYPE: DNA
<213> ORGANISM: Artificial Sequence
<220> FEATURE:
<223> OTHER INFORMATION: Made in a lab

<400> SEQUENCE: 56
atggctacag gctcccggac gtccctgctc ctggcttttg gcctgctctg cctgccctgg 60
cttcaagagg gcagtgcctt cccaaccatt cccggatcta tctactcgac cttcgccgac 120
cgggcgtacc cgggtggcct gacgtactcc ggccatccgc tggcgaccgc ctgcgcggtc 180
gcgacgatca acgcgatgga agacgaaggc atggtggcca acgctgcccg catcggcgag 240
caggtgctcg gaccgggtct gcgcgatctc gccgcccggc accgttcggt cggcgaagtc 300
cgcggcctcg gcgtcttctg ggcgggatct gatccagaac gggccggtct gcgggttgag 360
gtcctcggtg cccagtgccg tcgacgcgac gtcgtcggcg ctggtgatgc ggccgccgta 420
ggcgtcctcg gtccacaacg tcagcaccgt gcccgggcgg atggatctga tcggcaggca 480
tcacgaacag taagcggtgt tccggttgaa tccaatgtgc tgtcagcagg catccgatgc 540
cgaacaccga ccacgcgagc agtcgcaatc tgtctcgcga ccctggcgtc acgcggcgtc 600
gtggctccgc aacccgccgg cgatgtcgcg cgcgccgctg cggccggctc tccatggccg 660
gttcgttcag tcgctcgtcc ggtggctgtt ctgcgaacgg gcccgccgcc ccgtcgtccg 720
tccgatacgg gatctgatca gctcggggag ccgggtgccc agcaacgcca gcgtgggaag 780
caccgagacc ggcgcgatgt gcccgcgcag cagcgcccag ccgtgcaccc cgcgggaccg 840
ggccccgcgg accgcgtcgg agtcgacccc ggccgccacc gccgcgcgcg tggtcagcat 900
cagccacggg atggatctat cagttcggcc ctggtcgcca gcccgccgag ggcagccagt 960
tccgctccgg cgtcgatcgg gttgggtccg tccggccagc acaccagcat ccacccgagg 1020
tcgagcaacg ggtccccgac ggtgcacatc tcccagtcga tgaacgccgc gagctcgggg 1080
acgtcgcggc gcagcagcac gttgttcaga tggcagtcgc cgtgcatgat cccgggttcg 1140
gcgtcgtcgg gcctgcgcga gtccagccag tcggcgagca catgcaccga cgggaacgac 1200
tcgggcgcgg gatctatcac gcaggtaggc cgtccagccg tactcttcgc cccagaacag 1260
cggtgccgtc gccgcgcaga ccagcggtcc tgccgccaga tacacccagg cggtggccgg 1320
catgtccaga tcgtggccag cgcgcgcggc acggtggaga tcggatctat cgcgcggctg 1380
tgcgggaagg acgaggccgt agcggcgttg cactacgtcg ccccggttgg cgagaagcag 1440
gactacatcg accgagcctt gcgcaacatc gggccgtatc tgccagctga ggttcccgct 1500
ctcgtcggat ctatcgccgc caccggcccg gtgcccggca ccgcgtggat cgttcgtcag 1560
tacccgaagc tcttgagagc taaggccaat tgggaagata cttggacctt cccatcaata 1620
gaggaaaagc atcgccctag gggatccgta gcgggcccgg tgtttcgagt gaacttgggc 1680
agggcaatcc catcgcgcgc agcccgcgca gcggaaatcc acggatccca tcaccatcac 1740
catcactga 1749

<210> SEQ ID NO 57
<211> LENGTH: 1749
<212> TYPE: DNA
<213> ORGANISM: Artificial Sequence
<220> FEATURE:
<223> OTHER INFORMATION: Made in a lab -continued

<400> SEQUENCE: 57
atggctacag gctcccggac gtccctgctc ctggcttttg gcctgctctg cctgccctgg 60
cttcaagagg gcagtgcctt cccaaccatt cccggatcta tctactcgac cttcgccgac 120
cgggcgtacc cgggtggcct gacgtactcc ggccatccgc tggcgaccgc ctgcgcggtc 180
gcgacgatca acgcgatgga agacgaaggc atggtggcca acgctgcccg catcggcgag 240
caggtgctcg gaccgggtct gcgcgatctc gccgcccggc accgttcggt cggcgaagtc 300
cgcggcctcg gcgtcttctg ggcgggatct atcagttcgg ccctggtcgc cagcccgccg 360
agggcagcca gttccgctcc ggcgtcgatc gggttgggtc cgtccggcca gcacaccagc 420
atccacccga ggtcgagcaa cggtccccg acggtgcaca tctcccagtc gatgaacgcc 480
gcgagctcgg ggacgtcgcg gcgcagcagc acgttgttca gatggcagtc gccgtgcatg 540
atcccgggtt cggcgtcgtc gggcctgcgc gagtccagcc agtcggcgag cacatgcacc 600
gacgggaacg actcgggcgc gggatctgat cggcaggcat cacgaacagt aagcggtgtt 660
ccggttgaat ccaatgtgct gtcagcaggc atccgatgcc gaacaccgac cacgcgagca 720
gtcgcaatct gtctcgcgac cctggcgtca cgcggcgtcg tggctccgca acccgccggc 780
gatgtcgcgc gcgccgctgc ggccggctct ccatggccgg ttcgttcagt cgctcgtccg 840
gtggctgttc tgcgaacggg cccgccgccc cgtcgtccgt ccgatacggg atctgatcag 900
ctcggggagc cgggtgccca gcaacgccag cgtgggaagc accgagaccg gcgcgatgtg 960
cccgcgcagc agcgcccagc cgtgcacccc gcgggaccgg gccccgcgga ccgcgtcgga 1020
gtcgaccccg gccgccaccg ccgcgcgcgt ggtcagcatc agccacggga tggatctatc 1080
acgcaggtag gccgtccagc cgtactcttc gccccagaac agcggtgccg tcgccgcgca 1140
gaccagcggt cctgccgcca gatacaccca ggcggtggcc ggcatgtcca gatcgtggcc 1200
agcgcgcgcg gcacggtgga gatcggatct atcgcgcggc tgtgcgggaa ggacgaggcc 1260
gtagcggcgt tgcactacgt cgccccggtt ggcgagaagc aggactacat cgaccgagcc 1320
ttgcgcaaca tcgggccgta tctgccagct gaggttcccg ctctcgtcgg atctgatcca 1380
gaacgggccg gtctgcgggt tgaggtcctc ggtgcccagt gccgtcgacg cgacgtcgtc 1440
ggcgctggtg atgcggccgc cgtaggcgtc ctcggtccac aacgtcagca ccgtgcccgg 1500
gcggatggat ctatcgccgc caccggcccg gtgcccggca ccgcgtggat cgttcgtcag 1560
tacccgaagc tcttgagagc taaggccaat tgggaagata cttggacctt cccatcaata 1620
gaggaaaagc atcgccctag gggatccgta gcgggcccgg tgtttcgagt gaacttgggc 1680
agggcaatcc catcgcgcgc agcccgcgca gcggaaatcc acggatccca tcaccatcac 1740
catcactga 1749

<210> SEQ ID NO 58
<211> LENGTH: 1749
<212> TYPE: DNA
<213> ORGANISM: Artificial Sequence
<220> FEATURE:
<223> OTHER INFORMATION: Made in a lab

<400> SEQUENCE: 58
atggctacag gctcccggac gtccctgctc ctggcttttg gcctgctctg cctgccctgg 60
cttcaagagg gcagtgcctt cccaaccatt cccggatcta tctactcgac cttcgccgac 120
cgggcgtacc cgggtggcct gacgtactcc ggccatccgc tggcgaccgc ctgcgcggtc 180

-continued

```
gcgacgatca acgcgatgga agacgaaggc atggtggcca acgctgcccg catcggcgag    240

caggtgctcg gaccgggtct gcgcgatctc gccgcccggc accgttcggt cggcgaagtc    300

cgcggcctcg gcgtcttctg ggcgggatct gatccagaac gggccggtct gcgggttgag    360

gtcctcggtg cccagtgccg tcgacgcgac gtcgtcggcg ctggtgatgc ggccgccgta    420

ggcgtcctcg gtccacaacg tcagcaccgt gcccgggcgg atggatctat cagttcggcc    480

ctggtcgcca gcccgccgag ggcagccagt tccgctccgg cgtcgatcgg gttgggtccg    540

tccggccagc acaccagcat ccacccgagg tcgagcaacg ggtccccgac ggtgcacatc    600

tcccagtcga tgaacgccgc gagctcgggg acgtcgcggc gcagcagcac gttgttcaga    660

tggcagtcgc cgtgcatgat cccgggttcg gcgtcgtcgg gcctgcgcga gtccagccag    720

tcggcgagca catgcaccga cgggaacgac tcgggcgcgg gatctgatca gctcggggag    780

ccgggtgccc agcaacgcca gcgtgggaag caccgagacc ggcgcgatgt gcccgcgcag    840

cagcgcccag ccgtgcaccc cgcgggaccg ggccccgcgg accgcgtcgg agtcgacccc    900

ggccgccacc gccgcgcgcg tggtcagcat cagccacggg atggatctga tcggcaggca    960

tcacgaacag taagcggtgt tccggttgaa tccaatgtgc tgtcagcagg catccgatgc   1020

cgaacaccga ccacgcgagc agtcgcaatc tgtctcgcga ccctggcgtc acgcggcgtc   1080

gtggctccgc aacccgccgg cgatgtcgcg cgcgccgctg cggccggctc tccatggccg   1140

gttcgttcag tcgctcgtcc ggtggctgtt ctgcgaacgg gcccgccgcc ccgtcgtccg   1200

tccgatacgg gatctatcac gcaggtaggc cgtccagccg tactcttcgc cccagaacag   1260

cggtgccgtc gccgcgcaga ccagcggtcc tgccgccaga tacacccagg cggtggccgg   1320

catgtccaga tcgtggccag cgcgcgcggc acggtggaga tcggatctat cgcgcggctg   1380

tgcgggaagg acgaggccgt agcggcgttg cactacgtcg ccccggttgg cgagaagcag   1440

gactacatcg accgagcctt gcgcaacatc gggccgtatc tgccagctga ggttcccgct   1500

ctcgtcggat ctatcgccgc caccggcccg gtgcccggca ccgcgtggat cgttcgtcag   1560

tacccgaagc tcttgagagc taaggccaat tgggaagata cttggacctt cccatcaata   1620

gaggaaaagc atcgccctag gggatccgta gcgggcccgg tgtttcgagt gaacttgggc   1680

agggcaatcc catcgcgcgc agcccgcgca gcggaaatcc acggatccca tcaccatcac   1740

catcactga                                                           1749
```

<210> SEQ ID NO 59
<211> LENGTH: 23
<212> TYPE: DNA
<213> ORGANISM: Artificial Sequence
<220> FEATURE:
<223> OTHER INFORMATION: Made in a lab

<400> SEQUENCE: 59

```
cgatctactc gaccttcgcc gac                                             23
```

<210> SEQ ID NO 60
<211> LENGTH: 24
<212> TYPE: DNA
<213> ORGANISM: Artificial Sequence
<220> FEATURE:
<223> OTHER INFORMATION: Made in a lab

<400> SEQUENCE: 60

```
tcagtggatt tccgctgcgc gggc                                            24
```

-continued

<210> SEQ ID NO 61
<211> LENGTH: 46
<212> TYPE: PRT
<213> ORGANISM: Mycobacterium vaccae

<400> SEQUENCE: 61

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
            20                  25                  30

Ser Arg Leu Phe Asp Asn Ala Met Gln Leu Trp Leu Arg Asp
        35                  40                  45

<210> SEQ ID NO 62
<211> LENGTH: 46
<212> TYPE: PRT
<213> ORGANISM: Mycobacterium vaccae

<400> SEQUENCE: 62

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
            20                  25                  30

Ser Arg Leu Phe Asp Asn Ala Met Gln Leu Trp Leu Arg Ile
        35                  40                  45

<210> SEQ ID NO 63
<211> LENGTH: 46
<212> TYPE: PRT
<213> ORGANISM: Mycobacterium vaccae

<400> SEQUENCE: 63

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
            20                  25                  30

Ser Arg Leu Phe Asp Asn Ala Met Gln Leu Trp Leu Pro Gly
        35                  40                  45

<210> SEQ ID NO 64
<211> LENGTH: 13
<212> TYPE: PRT
<213> ORGANISM: Mycobacterium vaccae

<400> SEQUENCE: 64

Ile Ala Ala Thr Gly Pro Val Pro Gly Thr Ala Trp Ile
1               5                   10

<210> SEQ ID NO 65
<211> LENGTH: 32
<212> TYPE: PRT
<213> ORGANISM: Mycobacterium vaccae

<400> SEQUENCE: 65

Val Arg Gln Tyr Pro Lys Leu Leu Arg Ala Lys Ala Asn Trp Glu Asp
1               5                   10                  15

Thr Trp Thr Phe Pro Ser Ile Glu Glu Lys His Arg Pro Arg Gly Ser
            20                  25                  30

<210> SEQ ID NO 66
<211> LENGTH: 25
<212> TYPE: PRT

-continued

<213> ORGANISM: Mycobacterium vaccae

<400> SEQUENCE: 66

Val Ala Gly Pro Val Phe Arg Val Asn Leu Gly Arg Ala Ile Pro Ser
1 5 10 15

Arg Ala Ala Arg Ala Ala Glu Ile His
20 25

<210> SEQ ID NO 67
<211> LENGTH: 38
<212> TYPE: PRT
<213> ORGANISM: Mycobacterium vaccae

<400> SEQUENCE: 67

Ile Thr Gln Val Gly Arg Pro Ala Val Leu Phe Ala Pro Glu Gln Arg
1 5 10 15

Cys Arg Arg Arg Ala Asp Gln Arg Ser Cys Arg Gln Ile His Pro Gly
20 25 30

Gly Gly Arg His Val Gln
35

<210> SEQ ID NO 68
<211> LENGTH: 11
<212> TYPE: PRT
<213> ORGANISM: Mycobacterium vaccae

<400> SEQUENCE: 68

Ile Val Ala Ser Ala Arg Gly Thr Val Glu Ile
1 5 10

<210> SEQ ID NO 69
<211> LENGTH: 70
<212> TYPE: PRT
<213> ORGANISM: Mycobacteerium vaccae

<400> SEQUENCE: 69

Ile Ala Ala Thr Gly Pro Val Pro Gly Thr Ala Trp Ile Val Arg Gln
1 5 10 15

Tyr Pro Lys Leu Leu Arg Ala Lys Ala Asn Trp Glu Asp Thr Trp Thr
20 25 30

Phe Pro Ser Ile Glu Glu Lys His Arg Pro Arg Gly Ser Val Ala Gly
35 40 45

Pro Val Phe Arg Val Asn Leu Gly Arg Ala Ile Pro Ser Arg Ala Ala
50 55 60

Arg Ala Ala Glu Ile His
65 70

<210> SEQ ID NO 70
<211> LENGTH: 75
<212> TYPE: PRT
<213> ORGANISM: Mycobacterium vaccae

<400> SEQUENCE: 70

Ile Tyr Ser Thr Phe Ala Asp Arg Ala Tyr Pro Gly Gly Leu Thr Tyr
1 5 10 15

Ser Gly His Pro Leu Ala Thr Ala Cys Ala Val Ala Thr Ile Asn Ala
20 25 30

Met Glu Asp Glu Gly Met Val Ala Asn Ala Ala Arg Ile Gly Glu Gln
35 40 45

Val Leu Gly Pro Gly Leu Arg Asp Leu Ala Ala Arg His Arg Ser Val

-continued

```
    50                  55                  60

Gly Glu Val Arg Gly Leu Gly Val Phe Trp Ala
65                  70                  75


<210> SEQ ID NO 71
<211> LENGTH: 97
<212> TYPE: PRT
<213> ORGANISM: Mycobacterium vaccae

<400> SEQUENCE: 71

Ile Ser Ser Ala Leu Val Ala Ser Pro Pro Arg Ala Ala Ser Ser Ala
 1               5                  10                  15

Pro Ala Ser Ile Gly Leu Gly Pro Ser Gly Gln His Thr Ser Ile His
            20                  25                  30

Pro Arg Ser Ser Asn Gly Ser Pro Thr Val His Ile Ser Gln Ser Met
        35                  40                  45

Asn Ala Ala Ser Ser Gly Thr Ser Arg Arg Ser Ser Thr Leu Phe Arg
    50                  55                  60

Trp Gln Ser Pro Cys Met Ile Pro Gly Ser Ala Ser Ser Gly Leu Arg
65                  70                  75                  80

Glu Ser Ser Gln Ser Ala Ser Thr Cys Thr Asp Gly Asn Asp Ser Gly
                85                  90                  95

Ala


<210> SEQ ID NO 72
<211> LENGTH: 49
<212> TYPE: PRT
<213> ORGANISM: Mycobacterium vaccae

<400> SEQUENCE: 72

Ile Thr Gln Val Gly Arg Pro Ala Val Leu Phe Ala Pro Glu Gln Arg
 1               5                  10                  15

Cys Arg Arg Arg Ala Asp Gln Arg Ser Cys Arg Gln Ile His Pro Gly
            20                  25                  30

Gly Gly Arg His Val Gln Ile Val Ala Ser Ala Arg Gly Thr Val Glu
        35                  40                  45

Ile


<210> SEQ ID NO 73
<211> LENGTH: 46
<212> TYPE: PRT
<213> ORGANISM: Mycobacterium vaccae

<400> SEQUENCE: 73

Ile Ala Arg Leu Cys Gly Lys Asp Glu Ala Val Ala Ala Leu His Tyr
 1               5                  10                  15

Val Ala Pro Val Gly Glu Lys Gln Asp Tyr Ile Asp Arg Ala Leu Arg
            20                  25                  30

Asn Ile Gly Pro Tyr Leu Pro Ala Glu Val Pro Ala Leu Val
        35                  40                  45


<210> SEQ ID NO 74
<211> LENGTH: 87
<212> TYPE: PRT
<213> ORGANISM: Mycobacterium vaccae

<400> SEQUENCE: 74

Asp Arg Gln Ala Ser Arg Thr Val Ser Gly Val Pro Val Glu Ser Asn
 1               5                  10                  15
```

-continued

```
Val Leu Ser Ala Gly Ile Arg Cys Arg Thr Pro Thr Thr Arg Ala Val
            20                  25                  30

Ala Ile Cys Leu Ala Thr Leu Ala Ser Arg Gly Val Val Ala Pro Gln
        35                  40                  45

Pro Ala Gly Asp Val Ala Arg Ala Ala Ala Ala Gly Ser Pro Trp Pro
    50                  55                  60

Val Arg Ser Val Ala Arg Pro Val Ala Val Leu Arg Thr Gly Pro Pro
65                  70                  75                  80

Pro Arg Arg Pro Ser Asp Thr
                85


<210> SEQ ID NO 75
<211> LENGTH: 93
<212> TYPE: PRT
<213> ORGANISM: Mycobacterium vaccae

<400> SEQUENCE: 75

Asp Leu Val Ala Arg Pro Arg Asp Leu Arg Pro Val Arg Pro Ala Leu
 1               5                  10                  15

His His Arg Val Leu Pro Gly Ala Val Arg Gln Val Val Ala His Asp
            20                  25                  30

Arg Glu Thr Val Ala Ala Gly Gln Val Pro Ala Arg His Arg Arg Arg
        35                  40                  45

Arg Pro Gly Asp Pro Gln Arg Ala Asp Val Arg Arg Thr Gly Ser Val
    50                  55                  60

Gly Ala Ala Arg Ala Glu Val Gly His Arg Arg Gly Ala Val Ala Pro
65                  70                  75                  80

Ala Arg Gln Gly Arg Cys Glu Ser Arg Glu Asp Arg Asp
                85                  90


<210> SEQ ID NO 76
<211> LENGTH: 44
<212> TYPE: PRT
<213> ORGANISM: Mycobacterium vaccae

<400> SEQUENCE: 76

Asp Pro Glu Arg Ala Gly Leu Arg Val Glu Val Leu Gly Ala Gln Cys
 1               5                  10                  15

Arg Arg Arg Asp Val Val Gly Ala Gly Asp Ala Ala Ala Val Gly Val
            20                  25                  30

Leu Gly Pro Gln Arg Gln His Arg Ala Arg Ala Asp
        35                  40


<210> SEQ ID NO 77
<211> LENGTH: 59
<212> TYPE: PRT
<213> ORGANISM: Mycobacterium vaccae

<400> SEQUENCE: 77

Asp Gln Leu Gly Glu Pro Gly Ala Gln Gln Arg Gln Arg Gly Lys His
 1               5                  10                  15

Arg Asp Arg Arg Asp Val Pro Ala Gln Gln Arg Pro Ala Val His Pro
            20                  25                  30

Ala Gly Pro Gly Pro Ala Asp Arg Val Gly Val Asp Pro Gly Arg His
        35                  40                  45

Arg Arg Ala Arg Gly Gln His Gln Pro Arg Asp
    50                  55
```

-continued

<210> SEQ ID NO 78
<211> LENGTH: 39
<212> TYPE: PRT
<213> ORGANISM: Artificial Sequence
<220> FEATURE:
<223> OTHER INFORMATION: Made in a lab

<400> SEQUENCE: 78

```
Met Ala Thr Gly Ser Arg Thr Ser Leu Leu Leu Ala Phe Gly Leu Leu
 1               5                  10                  15

Cys Leu Pro Trp Leu Gln Glu Gly Ser Ala Phe Pro Thr Ile Pro Gly
            20                  25                  30

Ser His His His His His His
        35
```

<210> SEQ ID NO 79
<211> LENGTH: 582
<212> TYPE: PRT
<213> ORGANISM: Artificial Sequence
<220> FEATURE:
<223> OTHER INFORMATION: Made in a lab

<400> SEQUENCE: 79

```
Met Ala Thr Gly Ser Arg Thr Ser Leu Leu Leu Ala Phe Gly Leu Leu
 1               5                  10                  15

Cys Leu Pro Trp Leu Gln Glu Gly Ser Ala Phe Pro Thr Ile Pro Gly
            20                  25                  30

Ser Ile Tyr Ser Thr Phe Ala Asp Arg Ala Tyr Pro Gly Gly Leu Thr
        35                  40                  45

Tyr Ser Gly His Pro Leu Ala Thr Ala Cys Ala Val Ala Thr Ile Asn
    50                  55                  60

Ala Met Glu Asp Glu Gly Met Val Ala Asn Ala Ala Arg Ile Gly Glu
65                  70                  75                  80

Gln Val Leu Gly Pro Gly Leu Arg Asp Leu Ala Ala Arg His Arg Ser
                85                  90                  95

Val Gly Glu Val Arg Gly Leu Gly Val Phe Trp Ala Gly Ser Asp Pro
            100                 105                 110

Glu Arg Ala Gly Leu Arg Val Glu Val Leu Gly Ala Gln Cys Arg Arg
        115                 120                 125

Arg Asp Val Val Gly Ala Gly Asp Ala Ala Ala Val Gly Val Leu Gly
    130                 135                 140

Pro Gln Arg Gln His Arg Ala Arg Ala Asp Gly Ser Asp Arg Gln Ala
145                 150                 155                 160

Ser Arg Thr Val Ser Gly Val Pro Val Glu Ser Asn Val Leu Ser Ala
                165                 170                 175

Gly Ile Arg Cys Arg Thr Pro Thr Thr Arg Ala Val Ala Ile Cys Leu
            180                 185                 190

Ala Thr Leu Ala Ser Arg Gly Val Val Ala Pro Gln Pro Ala Gly Asp
        195                 200                 205

Val Ala Arg Ala Ala Ala Ala Gly Ser Pro Trp Pro Val Arg Ser Val
    210                 215                 220

Ala Arg Pro Val Ala Val Leu Arg Thr Gly Pro Pro Pro Arg Arg Pro
225                 230                 235                 240

Ser Asp Thr Gly Ser Asp Gln Leu Gly Glu Pro Gly Ala Gln Gln Arg
                245                 250                 255

Gln Arg Gly Lys His Arg Asp Arg Arg Asp Val Pro Ala Gln Gln Arg
            260                 265                 270
```

-continued

```
Pro Ala Val His Pro Ala Gly Pro Gly Pro Ala Asp Arg Val Gly Val
        275                 280                 285

Asp Pro Gly Arg His Arg Arg Ala Arg Gly Gln His Gln Pro Arg Asp
    290                 295                 300

Gly Ser Ile Ser Ser Ala Leu Val Ala Ser Pro Pro Arg Ala Ala Ser
305                 310                 315                 320

Ser Ala Pro Ala Ser Ile Gly Leu Gly Pro Ser Gly Gln His Thr Ser
                325                 330                 335

Ile His Pro Arg Ser Ser Asn Gly Ser Pro Thr Val His Ile Ser Gln
            340                 345                 350

Ser Met Asn Ala Ala Ser Ser Gly Thr Ser Arg Arg Ser Ser Thr Leu
        355                 360                 365

Phe Arg Trp Gln Ser Pro Cys Met Ile Pro Gly Ser Ala Ser Ser Gly
    370                 375                 380

Leu Arg Glu Ser Ser Gln Ser Ala Ser Thr Cys Thr Asp Gly Asn Asp
385                 390                 395                 400

Ser Gly Ala Gly Ser Ile Thr Gln Val Gly Arg Pro Ala Val Leu Phe
                405                 410                 415

Ala Pro Glu Gln Arg Cys Arg Arg Arg Ala Asp Gln Arg Ser Cys Arg
            420                 425                 430

Gln Ile His Pro Gly Gly Gly Arg His Val Gln Ile Val Ala Ser Ala
        435                 440                 445

Arg Gly Thr Val Glu Ile Gly Ser Ile Ala Arg Leu Cys Gly Lys Asp
    450                 455                 460

Glu Ala Val Ala Ala Leu His Tyr Val Ala Pro Val Gly Glu Lys Gln
465                 470                 475                 480

Asp Tyr Ile Asp Arg Ala Leu Arg Asn Ile Gly Pro Tyr Leu Pro Ala
                485                 490                 495

Glu Val Pro Ala Leu Val Gly Ser Ile Ala Ala Thr Gly Pro Val Pro
            500                 505                 510

Gly Thr Ala Trp Ile Val Arg Gln Tyr Pro Lys Leu Leu Arg Ala Lys
        515                 520                 525

Ala Asn Trp Glu Asp Thr Trp Thr Phe Pro Ser Ile Glu Glu Lys His
    530                 535                 540

Arg Pro Arg Gly Ser Val Ala Gly Pro Val Phe Arg Val Asn Leu Gly
545                 550                 555                 560

Arg Ala Ile Pro Ser Arg Ala Ala Arg Ala Ala Glu Ile His Gly Ser
                565                 570                 575

His His His His His His
            580


<210> SEQ ID NO 80
<211> LENGTH: 582
<212> TYPE: PRT
<213> ORGANISM: Artificial Sequence
<220> FEATURE:
<223> OTHER INFORMATION: Made in a lab

<400> SEQUENCE: 80

Met Ala Thr Gly Ser Arg Thr Ser Leu Leu Leu Ala Phe Gly Leu Leu
 1               5                  10                  15

Cys Leu Pro Trp Leu Gln Glu Gly Ser Ala Phe Pro Thr Ile Pro Gly
            20                  25                  30

Ser Ile Tyr Ser Thr Phe Ala Asp Arg Ala Tyr Pro Gly Gly Leu Thr
        35                  40                  45
```

-continued

```
Tyr Ser Gly His Pro Leu Ala Thr Ala Cys Ala Val Ala Thr Ile Asn
    50                  55                  60

Ala Met Glu Asp Glu Gly Met Val Ala Asn Ala Ala Arg Ile Gly Glu
65                  70                  75                  80

Gln Val Leu Gly Pro Gly Leu Arg Asp Leu Ala Ala Arg His Arg Ser
                85                  90                  95

Val Gly Glu Val Arg Gly Leu Gly Val Phe Trp Ala Gly Ser Ile Ser
            100                 105                 110

Ser Ala Leu Val Ala Ser Pro Pro Arg Ala Ala Ser Ser Ala Pro Ala
        115                 120                 125

Ser Ile Gly Leu Gly Pro Ser Gly Gln His Thr Ser Ile His Pro Arg
    130                 135                 140

Ser Ser Asn Gly Ser Pro Thr Val His Ile Ser Gln Ser Met Asn Ala
145                 150                 155                 160

Ala Ser Ser Gly Thr Ser Arg Arg Ser Ser Thr Leu Phe Arg Trp Gln
                165                 170                 175

Ser Pro Cys Met Ile Pro Gly Ser Ala Ser Ser Gly Leu Arg Glu Ser
            180                 185                 190

Ser Gln Ser Ala Ser Thr Cys Thr Asp Gly Asn Asp Ser Gly Ala Gly
        195                 200                 205

Ser Asp Arg Gln Ala Ser Arg Thr Val Ser Gly Val Pro Val Glu Ser
    210                 215                 220

Asn Val Leu Ser Ala Gly Ile Arg Cys Arg Thr Pro Thr Thr Arg Ala
225                 230                 235                 240

Val Ala Ile Cys Leu Ala Thr Leu Ala Ser Arg Gly Val Val Ala Pro
                245                 250                 255

Gln Pro Ala Gly Asp Val Ala Arg Ala Ala Ala Ala Gly Ser Pro Trp
            260                 265                 270

Pro Val Arg Ser Val Ala Arg Pro Val Ala Val Leu Arg Thr Gly Pro
        275                 280                 285

Pro Pro Arg Arg Pro Ser Asp Thr Gly Ser Asp Gln Leu Gly Glu Pro
    290                 295                 300

Gly Ala Gln Gln Arg Gln Arg Gly Lys His Arg Asp Arg Arg Asp Val
305                 310                 315                 320

Pro Ala Gln Gln Arg Pro Ala Val His Pro Ala Gly Pro Gly Pro Ala
                325                 330                 335

Asp Arg Val Gly Val Asp Pro Gly Arg His Arg Arg Ala Arg Gly Gln
            340                 345                 350

His Gln Pro Arg Asp Gly Ser Ile Thr Gln Val Gly Arg Pro Ala Val
        355                 360                 365

Leu Phe Ala Pro Glu Gln Arg Cys Arg Arg Arg Ala Asp Gln Arg Ser
    370                 375                 380

Cys Arg Gln Ile His Pro Gly Gly Gly Arg His Val Gln Ile Val Ala
385                 390                 395                 400

Ser Ala Arg Gly Thr Val Glu Ile Gly Ser Ile Ala Arg Leu Cys Gly
                405                 410                 415

Lys Asp Glu Ala Val Ala Ala Leu His Tyr Val Ala Pro Val Gly Glu
            420                 425                 430

Lys Gln Asp Tyr Ile Asp Arg Ala Leu Arg Asn Ile Gly Pro Tyr Leu
        435                 440                 445

Pro Ala Glu Val Pro Ala Leu Val Gly Ser Asp Pro Glu Arg Ala Gly
    450                 455                 460
```

-continued

```
Leu Arg Val Glu Val Leu Gly Ala Gln Cys Arg Arg Arg Asp Val Val
465                 470                 475                 480

Gly Ala Gly Asp Ala Ala Ala Val Gly Val Leu Gly Pro Gln Arg Gln
                485                 490                 495

His Arg Ala Arg Ala Asp Gly Ser Ile Ala Ala Thr Gly Pro Val Pro
            500                 505                 510

Gly Thr Ala Trp Ile Val Arg Gln Tyr Pro Lys Leu Leu Arg Ala Lys
        515                 520                 525

Ala Asn Trp Glu Asp Thr Trp Thr Phe Pro Ser Ile Glu Glu Lys His
    530                 535                 540

Arg Pro Arg Gly Ser Val Ala Gly Pro Val Phe Arg Val Asn Leu Gly
545                 550                 555                 560

Arg Ala Ile Pro Ser Arg Ala Ala Arg Ala Ala Glu Ile His Gly Ser
                565                 570                 575

His His His His His His
            580


<210> SEQ ID NO 81
<211> LENGTH: 582
<212> TYPE: PRT
<213> ORGANISM: Artificial Sequence
<220> FEATURE:
<223> OTHER INFORMATION: Made in a lab

<400> SEQUENCE: 81

Met Ala Thr Gly Ser Arg Thr Ser Leu Leu Leu Ala Phe Gly Leu Leu
 1               5                  10                  15

Cys Leu Pro Trp Leu Gln Glu Gly Ser Ala Phe Pro Thr Ile Pro Gly
            20                  25                  30

Ser Ile Tyr Ser Thr Phe Ala Asp Arg Ala Tyr Pro Gly Gly Leu Thr
        35                  40                  45

Tyr Ser Gly His Pro Leu Ala Thr Ala Cys Ala Val Ala Thr Ile Asn
    50                  55                  60

Ala Met Glu Asp Glu Gly Met Val Ala Asn Ala Ala Arg Ile Gly Glu
65                  70                  75                  80

Gln Val Leu Gly Pro Gly Leu Arg Asp Leu Ala Ala Arg His Arg Ser
                85                  90                  95

Val Gly Glu Val Arg Gly Leu Gly Val Phe Trp Ala Gly Ser Asp Pro
            100                 105                 110

Glu Arg Ala Gly Leu Arg Val Glu Val Leu Gly Ala Gln Cys Arg Arg
        115                 120                 125

Arg Asp Val Val Gly Ala Gly Asp Ala Ala Ala Val Gly Val Leu Gly
    130                 135                 140

Pro Gln Arg Gln His Arg Ala Arg Ala Asp Gly Ser Ile Ser Ser Ala
145                 150                 155                 160

Leu Val Ala Ser Pro Pro Arg Ala Ala Ser Ser Ala Pro Ala Ser Ile
                165                 170                 175

Gly Leu Gly Pro Ser Gly Gln His Thr Ser Ile His Pro Arg Ser Ser
            180                 185                 190

Asn Gly Ser Pro Thr Val His Ile Ser Gln Ser Met Asn Ala Ala Ser
        195                 200                 205

Ser Gly Thr Ser Arg Arg Ser Ser Thr Leu Phe Arg Trp Gln Ser Pro
    210                 215                 220

Cys Met Ile Pro Gly Ser Ala Ser Ser Gly Leu Arg Glu Ser Ser Gln
225                 230                 235                 240
```

-continued

```
Ser Ala Ser Thr Cys Thr Asp Gly Asn Asp Ser Gly Ala Gly Ser Asp
                245                 250                 255

Gln Leu Gly Glu Pro Gly Ala Gln Gln Arg Gln Arg Gly Lys His Arg
            260                 265                 270

Asp Arg Arg Asp Val Pro Ala Gln Gln Arg Pro Ala Val His Pro Ala
        275                 280                 285

Gly Pro Gly Pro Ala Asp Arg Val Gly Val Asp Pro Gly Arg His Arg
    290                 295                 300

Arg Ala Arg Gly Gln His Gln Pro Arg Asp Gly Ser Asp Arg Gln Ala
305                 310                 315                 320

Ser Arg Thr Val Ser Gly Val Pro Val Glu Ser Asn Val Leu Ser Ala
                325                 330                 335

Gly Ile Arg Cys Arg Thr Pro Thr Thr Arg Ala Val Ala Ile Cys Leu
            340                 345                 350

Ala Thr Leu Ala Ser Arg Gly Val Val Ala Pro Gln Pro Ala Gly Asp
        355                 360                 365

Val Ala Arg Ala Ala Ala Ala Gly Ser Pro Trp Pro Val Arg Ser Val
    370                 375                 380

Ala Arg Pro Val Ala Val Leu Arg Thr Gly Pro Pro Pro Arg Arg Pro
385                 390                 395                 400

Ser Asp Thr Gly Ser Ile Thr Gln Val Gly Arg Pro Ala Val Leu Phe
                405                 410                 415

Ala Pro Glu Gln Arg Cys Arg Arg Arg Ala Asp Gln Arg Ser Cys Arg
            420                 425                 430

Gln Ile His Pro Gly Gly Gly Arg His Val Gln Ile Val Ala Ser Ala
        435                 440                 445

Arg Gly Thr Val Glu Ile Gly Ser Ile Ala Arg Leu Cys Gly Lys Asp
    450                 455                 460

Glu Ala Val Ala Ala Leu His Tyr Val Ala Pro Val Gly Glu Lys Gln
465                 470                 475                 480

Asp Tyr Ile Asp Arg Ala Leu Arg Asn Ile Gly Pro Tyr Leu Pro Ala
                485                 490                 495

Glu Val Pro Ala Leu Val Gly Ser Ile Ala Ala Thr Gly Pro Val Pro
            500                 505                 510

Gly Thr Ala Trp Ile Val Arg Gln Tyr Pro Lys Leu Leu Arg Ala Lys
        515                 520                 525

Ala Asn Trp Glu Asp Thr Trp Thr Phe Pro Ser Ile Glu Glu Lys His
    530                 535                 540

Arg Pro Arg Gly Ser Val Ala Gly Pro Val Phe Arg Val Asn Leu Gly
545                 550                 555                 560

Arg Ala Ile Pro Ser Arg Ala Ala Arg Ala Ala Glu Ile His Gly Ser
                565                 570                 575

His His His His His His
            580
```

<210> SEQ ID NO 82
<211> LENGTH: 225
<212> TYPE: DNA
<213> ORGANISM: Mycobacterium vaccae

<400> SEQUENCE: 82

```
atctactcga ccttcgccga ccgggcgtac ccgggtggcc tgacgtactc cggccatccg      60

ctggcgaccg cctgcgcggt cgcgacgatc aacgcgatgg aagacgaagg catggtggcc     120

aacgctgccc gcatcggcga gcaggtgctc ggaccgggtc tgcgcgatct cgccgcccgg     180
```

-continued

```
caccgttcgg tcggcgaagt ccgcggcctc ggcgtcttct gggcg                 225

<210> SEQ ID NO 83
<211> LENGTH: 363
<212> TYPE: DNA
<213> ORGANISM: Mycobacterium vaccae

<400> SEQUENCE: 83

atctactcga ccttcgccga ccgggcgtac ccgggtggcc tgacgtactc cggccatccg    60

ctggcgaccg cctgcgcggt cgcgacgatc aacgcgatgg aagacgaagg catggtggcc   120

aacgctgccc gcatcggcga gcaggtgctc ggaccgggtc tgcgcgatct cgccgcccgg   180

caccgttcgg tcggcgaagt ccgcggcctc ggcgtcttct gggcgggatc tgatccagaa   240

cgggccggtc tgcgggttga ggtcctcggt gcccagtgcc gtcgacgcga cgtcgtcggc   300

gctggtgatg cggccgccgt aggcgtcctc ggtccacaac gtcagcaccg tgcccgggcg   360

gat                                                                 363

<210> SEQ ID NO 84
<211> LENGTH: 660
<212> TYPE: DNA
<213> ORGANISM: Mycobacterium vaccae

<400> SEQUENCE: 84

atctactcga ccttcgccga ccgggcgtac ccgggtggcc tgacgtactc cggccatccg    60

ctggcgaccg cctgcgcggt cgcgacgatc aacgcgatgg aagacgaagg catggtggcc   120

aacgctgccc gcatcggcga gcaggtgctc ggaccgggtc tgcgcgatct cgccgcccgg   180

caccgttcgg tcggcgaagt ccgcggcctc ggcgtcttct gggcgggatc tgatccagaa   240

cgggccggtc tgcgggttga ggtcctcggt gcccagtgcc gtcgacgcga cgtcgtcggc   300

gctggtgatg cggccgccgt aggcgtcctc ggtccacaac gtcagcaccg tgcccgggcg   360

gatggatcta tcagttcggc cctggtcgcc agcccgccga gggcagccag ttccgctccg   420

gcgtcgatcg ggttgggtcc gtccggccag cacaccagca tccacccgag gtcgagcaac   480

gggtccccga cggtgcacat ctcccagtcg atgaacgccg cgagctcggg gacgtcgcgg   540

cgcagcagca cgttgttcag atggcagtcg ccgtgcatga tcccgggttc ggcgtcgtcg   600

ggcctgcgcg agtccagcca gtcggcgagc acatgcaccg acgggaacga ctcgggcgcg   660

<210> SEQ ID NO 85
<211> LENGTH: 843
<212> TYPE: DNA
<213> ORGANISM: Mycobacterium vaccae

<400> SEQUENCE: 85

atctactcga ccttcgccga ccgggcgtac ccgggtggcc tgacgtactc cggccatccg    60

ctggcgaccg cctgcgcggt cgcgacgatc aacgcgatgg aagacgaagg catggtggcc   120

aacgctgccc gcatcggcga gcaggtgctc ggaccgggtc tgcgcgatct cgccgcccgg   180

caccgttcgg tcggcgaagt ccgcggcctc ggcgtcttct gggcgggatc tgatccagaa   240

cgggccggtc tgcgggttga ggtcctcggt gcccagtgcc gtcgacgcga cgtcgtcggc   300

gctggtgatg cggccgccgt aggcgtcctc ggtccacaac gtcagcaccg tgcccgggcg   360

gatggatcta tcagttcggc cctggtcgcc agcccgccga gggcagccag ttccgctccg   420

gcgtcgatcg ggttgggtcc gtccggccag cacaccagca tccacccgag gtcgagcaac   480
```

-continued

```
gggtccccga cggtgcacat ctcccagtcg atgaacgccg cgagctcggg gacgtcgcgg    540

cgcagcagca cgttgttcag atggcagtcg ccgtgcatga tcccgggttc ggcgtcgtcg    600

ggcctgcgcg agtccagcca gtcggcgagc acatgcaccg acgggaacga ctcgggcgcg    660

ggatctgatc agctcgggga gccgggtgcc cagcaacgcc agcgtgggaa gcaccgagac    720

cggcgcgatg tgcccgcgca gcagcgccca gccgtgcacc ccgcgggacc gggccccgcg    780

gaccgcgtcg gagtcgaccc cggccgccac cgccgcgcgc gtggtcagca tcagccacgg    840

gat                                                                   843
```

<210> SEQ ID NO 86
<211> LENGTH: 1116
<212> TYPE: DNA
<213> ORGANISM: Mycobacterium vaccae

<400> SEQUENCE: 86

```
atctactcga ccttcgccga ccgggcgtac ccgggtggcc tgacgtactc cggccatccg     60

ctggcgaccg cctgcgcggt cgcgacgatc aacgcgatgg aagacgaagg catggtggcc    120

aacgctgccc gcatcggcga gcaggtgctc ggaccgggtc tgcgcgatct cgccgcccgg    180

caccgttcgg tcggcgaagt ccgcggcctc ggcgtcttct gggcgggatc tgatccagaa    240

cgggccggtc tgcgggttga ggtcctcggt gcccagtgcc gtcgacgcga cgtcgtcggc    300

gctggtgatg cggccgccgt aggcgtcctc ggtccacaac gtcagcaccg tgcccgggcg    360

gatggatcta tcagttcggc cctggtcgcc agcccgccga gggcagccag ttccgctccg    420

gcgtcgatcg ggttgggtcc gtccggccag cacaccagca tccacccgag gtcgagcaac    480

gggtccccga cggtgcacat ctcccagtcg atgaacgccg cgagctcggg gacgtcgcgg    540

cgcagcagca cgttgttcag atggcagtcg ccgtgcatga tcccgggttc ggcgtcgtcg    600

ggcctgcgcg agtccagcca gtcggcgagc acatgcaccg acgggaacga ctcgggcgcg    660

ggatctgatc agctcgggga gccgggtgcc cagcaacgcc agcgtgggaa gcaccgagac    720

cggcgcgatg tgcccgcgca gcagcgccca gccgtgcacc ccgcgggacc gggccccgcg    780

gaccgcgtcg gagtcgaccc cggccgccac cgccgcgcgc gtggtcagca tcagccacgg    840

gatggatctg atcggcaggc atcacgaaca gtaagcggtg ttccggttga atccaatgtg    900

ctgtcagcag gcatccgatg ccgaacaccg accacgcgag cagtcgcaat ctgtctcgcg    960

accctggcgt cacgcggcgt cgtggctccg caacccgccg gcgatgtcgc gcgcgccgct   1020

gcggccggct ctccatggcc ggttcgttca gtcgctcgtc cggtggctgt tctgcgaacg   1080

ggcccgccgc cccgtcgtcc gtccgatacg ggatct                             1116
```

<210> SEQ ID NO 87
<211> LENGTH: 1263
<212> TYPE: DNA
<213> ORGANISM: Mycobacterium vaccae

<400> SEQUENCE: 87

```
atctactcga ccttcgccga ccgggcgtac ccgggtggcc tgacgtactc cggccatccg     60

ctggcgaccg cctgcgcggt cgcgacgatc aacgcgatgg aagacgaagg catggtggcc    120

aacgctgccc gcatcggcga gcaggtgctc ggaccgggtc tgcgcgatct cgccgcccgg    180

caccgttcgg tcggcgaagt ccgcggcctc ggcgtcttct gggcgggatc tgatccagaa    240

cgggccggtc tgcgggttga ggtcctcggt gcccagtgcc gtcgacgcga cgtcgtcggc    300

gctggtgatg cggccgccgt aggcgtcctc ggtccacaac gtcagcaccg tgcccgggcg    360
```

-continued

```
gatggatctt cggccctggt cgccagcccg ccgagggcag ccagttccgc tccggcgtcg    420

atcgggttgg gtccgtccgg ccagcacacc agcatccacc cgaggtcgag caacgggtcc    480

ccgacggtgc acatctccca gtcgatgaac gccgcgagct cggggacgtc gcggcgcagc    540

agcacgttgt tcagatggca gtcgccgtgc atgatcccgg gttcggcgtc gtcgggcctg    600

cgcgagtcca gccagtcggc gagcacatgc accgacggga acgactcggg cgcgggatct    660

gatcagctcg gggagccggg tgcccagcaa cgccagcgtg ggaagcaccg agaccggcgc    720

gatgtgcccg cgcagcagcg cccagccgtg caccccgcgg gaccgggccc cgcggaccgc    780

gtcggagtcg accccggccg ccaccgccgc gcgcgtggtc agcatcagcc acgggatgga    840

tctgatcggc aggcatcacg aacagtaagc ggtgttccgg ttgaatccaa tgtgctgtca    900

gcaggcatcc gatgccgaac accgaccacg cgagcagtcg caatctgtct cgcgaccctg    960

gcgtcacgcg gcgtcgtggc tccgcaaccc gccggcgatg tcgcgcgcgc cgctgcggcc   1020

ggctctccat ggccggttcg ttcagtcgct cgtccggtgg ctgttctgcg aacgggcccg   1080

ccgccccgtc gtccgtccga tacgggatct atcacgcagg taggccgtcc agccgtactc   1140

ttcgccccag aacagcggtg ccgtcgccgc gcagaccagc ggtcctgccg ccagatacac   1200

ccaggcggtg gccggcatgt ccagatcgtg gccagcgcgc gcggcacggt ggagatcgga   1260

tct                                                                 1263
```

<210> SEQ ID NO 88
<211> LENGTH: 1413
<212> TYPE: DNA
<213> ORGANISM: Mycobacterium vaccae

<400> SEQUENCE: 88

```
atctactcga ccttcgccga ccgggcgtac ccgggtggcc tgacgtactc cggccatccg     60

ctggcgaccg cctgcgcggt cgcgacgatc aacgcgatgg aagacgaagg catggtggcc    120

aacgctgccc gcatcggcga gcaggtgctc ggaccgggtc tgcgcgatct cgccgcccgg    180

caccgttcgg tcggcgaagt ccgcggcctc ggcgtcttct gggcgggatc tgatccagaa    240

cgggccggtc tgcgggttga ggtcctcggt gcccagtgcc gtcgacgcga cgtcgtcggc    300

gctggtgatg cggccgccgt aggcgtcctc ggtccacaac gtcagcaccg tgcccgggcg    360

gatggatcta tcagttcggc cctggtcgcc agcccgccga gggcagccag ttccgctccg    420

gcgtcgatcg ggttgggtcc gtccggccag cacaccagca tccacccgag gtcgagcaac    480

gggtccccga cggtgcacat ctcccagtcg atgaacgccg cgagctcggg gacgtcgcgg    540

cgcagcagca cgttgttcag atggcagtcg ccgtgcatga tcccgggttc ggcgtcgtcg    600

ggcctgcgcg agtccagcca gtcggcgagc acatgcaccg acgggaacga ctcgggcgcg    660

ggatctgatc agctcgggga gccgggtgcc cagcaacgcc agcgtgggaa gcaccgagac    720

cggcgcgatg tgcccgcgca gcagcgccca gccgtgcacc ccgcgggacc gggccccgcg    780

gaccgcgtcg gagtcgaccc cggccgccac cgccgcgcgc gtggtcagca tcagccacgg    840

gatggatctg atcggcaggc atcacgaaca gtaagcggtg ttccggttga atccaatgtg    900

ctgtcagcag gcatccgatg ccgaacaccg accacgcgag cagtcgcaat ctgtctcgcg    960

accctggcgt cacgcggcgt cgtggctccg caacccgccg gcgatgtcgc gcgcgccgct   1020

gcggccggct ctccatggcc ggttcgttca gtcgctcgtc cggtggctgt tctgcgaacg   1080

ggcccgccgc cccgtcgtcc gtccgatacg ggatctatca cgcaggtagg ccgtccagcc   1140
```

-continued

```
gtactcttcg ccccagaaca gcggtgccgt cgccgcgcag accagcggtc ctgccgccag   1200

atacacccag gcggtggccg gcatgtccag atcgtggcca gcgcgcgcgg cacggtggag   1260

atcggatcta tcgcgcggct gtgcgggaag gacgaggccg tagcggcgtt gcactacgtc   1320

gccccggttg gcgagaagca ggactacatc gaccgagcct tgcgcaacat cgggccgtat   1380

ctgccagctg aggttcccgc tctcgtcgga tct                                1413
```

<210> SEQ ID NO 89
<211> LENGTH: 1623
<212> TYPE: DNA
<213> ORGANISM: Mycobacterium vaccae

<400> SEQUENCE: 89

```
atctactcga ccttcgccga ccgggcgtac ccgggtggcc tgacgtactc cggccatccg     60

ctggcgaccg cctgcgcggt cgcgacgatc aacgcgatgg aagacgaagg catggtggcc    120

aacgctgccc gcatcggcga gcaggtgctc ggaccgggtc tgcgcgatct cgccgcccgg    180

caccgttcgg tcggcgaagt ccgcggcctc ggcgtcttct gggcgggatc tgatccagaa    240

cgggccggtc tgcgggttga ggtcctcggt gcccagtgcc gtcgacgcga cgtcgtcggc    300

gctggtgatg cggccgccgt aggcgtcctc ggtccacaac gtcagcaccg tgcccgggcg    360

gatggatcta tcagttcggc cctggtcgcc agcccgccga gggcagccag ttccgctccg    420

gcgtcgatcg ggttgggtcc gtccggccag cacaccagca tccacccgag gtcgagcaac    480

gggtccccga cggtgcacat ctcccagtcg atgaacgccg cgagctcggg gacgtcgcgg    540

cgcagcagca cgttgttcag atggcagtcg ccgtgcatga tcccgggttc ggcgtcgtcg    600

ggcctgcgcg agtccagcca gtcggcgagc acatgcaccg acgggaacga ctcgggcgcg    660

ggatctgatc agctcgggga gccgggtgcc cagcaacgcc agcgtgggaa gcaccgagac    720

cggcgcgatg tgcccgcgca gcagcgccca gccgtgcacc ccgcgggacc gggccccgcg    780

gaccgcgtcg gagtcgaccc cggccgccac cgccgcgcgc gtggtcagca tcagccacgg    840

gatggatctg atcggcaggc atcacgaaca gtaagcggtg ttccggttga atccaatgtg    900

ctgtcagcag gcatccgatg ccgaacaccg accacgcgag cagtcgcaat ctgtctcgcg    960

accctggcgt cacgcggcgt cgtggctccg caacccgccg gcgatgtcgc gcgcgccgct   1020

gcggccggct ctccatggcc ggttcgttca gtcgctcgtc cggtggctgt tctgcgaacg   1080

ggcccgccgc cccgtcgtcc gtccgatacg ggatctatca cgcaggtagg ccgtccagcc   1140

gtactcttcg ccccagaaca gcggtgccgt cgccgcgcag accagcggtc ctgccgccag   1200

atacacccag gcggtggccg gcatgtccag atcgtggcca gcgcgcgcgg cacggtggag   1260

atcggatcta tcgcgcggct gtgcgggaag gacgaggccg tagcggcgtt gcactacgtc   1320

gccccggttg gcgagaagca ggactacatc gaccgagcct tgcgcaacat cgggccgtat   1380

ctgccagctg aggttcccgc tctcgtcgga tctatcgccg ccaccggccc ggtgcccggc   1440

accgcgtgga tcgttcgtca gtacccgaag ctcttgagag ctaaggccaa ttgggaagat   1500

acttggacct tcccatcaat agaggaaaag catcgcccta ggggatccgt agcgggcccg   1560

gtgtttcgag tgaacttggg cagggcaatc ccatcgcgcg cagcccgcgc agcggaaatc   1620

cac                                                                 1623
```

<210> SEQ ID NO 90
<211> LENGTH: 75
<212> TYPE: PRT
<213> ORGANISM: Mycobacterium vaccae -continued

<400> SEQUENCE: 90

```
Ile Tyr Ser Thr Phe Ala Asp Arg Ala Tyr Pro Gly Gly Leu Thr Tyr
 1              5                   10                  15

Ser Gly His Pro Leu Ala Thr Ala Cys Ala Val Ala Thr Ile Asn Ala
            20                  25                  30

Met Glu Asp Glu Gly Met Val Ala Asn Ala Ala Arg Ile Gly Glu Gln
        35                  40                  45

Val Leu Gly Pro Gly Leu Arg Asp Leu Ala Ala Arg His Arg Ser Val
    50                  55                  60

Gly Glu Val Arg Gly Leu Gly Val Phe Trp Ala
65                  70                  75
```

<210> SEQ ID NO 91
<211> LENGTH: 121
<212> TYPE: PRT
<213> ORGANISM: Mycobacterium vaccae

<400> SEQUENCE: 91

```
Ile Tyr Ser Thr Phe Ala Asp Arg Ala Tyr Pro Gly Gly Leu Thr Tyr
 1              5                   10                  15

Ser Gly His Pro Leu Ala Thr Ala Cys Ala Val Ala Thr Ile Asn Ala
            20                  25                  30

Met Glu Asp Glu Gly Met Val Ala Asn Ala Ala Arg Ile Gly Glu Gln
        35                  40                  45

Val Leu Gly Pro Gly Leu Arg Asp Leu Ala Ala Arg His Arg Ser Val
    50                  55                  60

Gly Glu Val Arg Gly Leu Gly Val Phe Trp Ala Gly Ser Asp Pro Glu
65                  70                  75                  80

Arg Ala Gly Leu Arg Val Glu Val Leu Gly Ala Gln Cys Arg Arg Arg
                85                  90                  95

Asp Val Val Gly Ala Gly Asp Ala Ala Ala Val Gly Val Leu Gly Pro
            100                 105                 110

Gln Arg Gln His Arg Ala Arg Ala Asp
        115                 120
```

<210> SEQ ID NO 92
<211> LENGTH: 220
<212> TYPE: PRT
<213> ORGANISM: Mycobacterium vaccae

<400> SEQUENCE: 92

```
Ile Tyr Ser Thr Phe Ala Asp Arg Ala Tyr Pro Gly Gly Leu Thr Tyr
 1              5                   10                  15

Ser Gly His Pro Leu Ala Thr Ala Cys Ala Val Ala Thr Ile Asn Ala
            20                  25                  30

Met Glu Asp Glu Gly Met Val Ala Asn Ala Ala Arg Ile Gly Glu Gln
        35                  40                  45

Val Leu Gly Pro Gly Leu Arg Asp Leu Ala Ala Arg His Arg Ser Val
    50                  55                  60

Gly Glu Val Arg Gly Leu Gly Val Phe Trp Ala Gly Ser Asp Pro Glu
65                  70                  75                  80

Arg Ala Gly Leu Arg Val Glu Val Leu Gly Ala Gln Cys Arg Arg Arg
                85                  90                  95

Asp Val Val Gly Ala Gly Asp Ala Ala Ala Val Gly Val Leu Gly Pro
            100                 105                 110
```

-continued

```
Gln Arg Gln His Arg Ala Arg Ala Asp Gly Ser Ile Ser Ser Ala Leu
        115                 120                 125

Val Ala Ser Pro Pro Arg Ala Ala Ser Ser Ala Pro Ala Ser Ile Gly
    130                 135                 140

Leu Gly Pro Ser Gly Gln His Thr Ser Ile His Pro Arg Ser Ser Asn
145                 150                 155                 160

Gly Ser Pro Thr Val His Ile Ser Gln Ser Met Asn Ala Ala Ser Ser
                165                 170                 175

Gly Thr Ser Arg Arg Ser Ser Thr Leu Phe Arg Trp Gln Ser Pro Cys
            180                 185                 190

Met Ile Pro Gly Ser Ala Ser Ser Gly Leu Arg Glu Ser Ser Gln Ser
        195                 200                 205

Ala Ser Thr Cys Thr Asp Gly Asn Asp Ser Gly Ala
    210                 215                 220


<210> SEQ ID NO 93
<211> LENGTH: 281
<212> TYPE: PRT
<213> ORGANISM: Mycobacterium vaccae

<400> SEQUENCE: 93

Ile Tyr Ser Thr Phe Ala Asp Arg Ala Tyr Pro Gly Gly Leu Thr Tyr
 1               5                  10                  15

Ser Gly His Pro Leu Ala Thr Ala Cys Ala Val Ala Thr Ile Asn Ala
            20                  25                  30

Met Glu Asp Glu Gly Met Val Ala Asn Ala Ala Arg Ile Gly Glu Gln
        35                  40                  45

Val Leu Gly Pro Gly Leu Arg Asp Leu Ala Ala Arg His Arg Ser Val
    50                  55                  60

Gly Glu Val Arg Gly Leu Gly Val Phe Trp Ala Gly Ser Asp Pro Glu
65                  70                  75                  80

Arg Ala Gly Leu Arg Val Glu Val Leu Gly Ala Gln Cys Arg Arg Arg
                85                  90                  95

Asp Val Val Gly Ala Gly Asp Ala Ala Ala Val Gly Val Leu Gly Pro
            100                 105                 110

Gln Arg Gln His Arg Ala Arg Ala Asp Gly Ser Ile Ser Ser Ala Leu
        115                 120                 125

Val Ala Ser Pro Pro Arg Ala Ala Ser Ser Ala Pro Ala Ser Ile Gly
    130                 135                 140

Leu Gly Pro Ser Gly Gln His Thr Ser Ile His Pro Arg Ser Ser Asn
145                 150                 155                 160

Gly Ser Pro Thr Val His Ile Ser Gln Ser Met Asn Ala Ala Ser Ser
                165                 170                 175

Gly Thr Ser Arg Arg Ser Ser Thr Leu Phe Arg Trp Gln Ser Pro Cys
            180                 185                 190

Met Ile Pro Gly Ser Ala Ser Ser Gly Leu Arg Glu Ser Ser Gln Ser
        195                 200                 205

Ala Ser Thr Cys Thr Asp Gly Asn Asp Ser Gly Ala Gly Ser Asp Gln
    210                 215                 220

Leu Gly Glu Pro Gly Ala Gln Gln Arg Gln Arg Gly Lys His Arg Asp
225                 230                 235                 240

Arg Arg Asp Val Pro Ala Gln Gln Arg Pro Ala Val His Pro Ala Gly
                245                 250                 255

Pro Gly Pro Ala Asp Arg Val Gly Val Asp Pro Gly Arg His Arg Arg
            260                 265                 270
```

-continued

```
Ala Arg Gly Gln His Gln Pro Arg Asp
        275                 280


<210> SEQ ID NO 94
<211> LENGTH: 372
<212> TYPE: PRT
<213> ORGANISM: Mycobacterium vaccae

<400> SEQUENCE: 94

Ile Tyr Ser Thr Phe Ala Asp Arg Ala Tyr Pro Gly Gly Leu Thr Tyr
 1               5                  10                  15

Ser Gly His Pro Leu Ala Thr Ala Cys Ala Val Ala Thr Ile Asn Ala
            20                  25                  30

Met Glu Asp Glu Gly Met Val Ala Asn Ala Ala Arg Ile Gly Glu Gln
        35                  40                  45

Val Leu Gly Pro Gly Leu Arg Asp Leu Ala Ala Arg His Arg Ser Val
    50                  55                  60

Gly Glu Val Arg Gly Leu Gly Val Phe Trp Ala Gly Ser Asp Pro Glu
65                  70                  75                  80

Arg Ala Gly Leu Arg Val Glu Val Leu Gly Ala Gln Cys Arg Arg Arg
                85                  90                  95

Asp Val Val Gly Ala Gly Asp Ala Ala Ala Val Gly Val Leu Gly Pro
            100                 105                 110

Gln Arg Gln His Arg Ala Arg Ala Asp Gly Ser Ile Ser Ser Ala Leu
        115                 120                 125

Val Ala Ser Pro Pro Arg Ala Ala Ser Ser Ala Pro Ala Ser Ile Gly
    130                 135                 140

Leu Gly Pro Ser Gly Gln His Thr Ser Ile His Pro Arg Ser Ser Asn
145                 150                 155                 160

Gly Ser Pro Thr Val His Ile Ser Gln Ser Met Asn Ala Ala Ser Ser
                165                 170                 175

Gly Thr Ser Arg Arg Ser Ser Thr Leu Phe Arg Trp Gln Ser Pro Cys
            180                 185                 190

Met Ile Pro Gly Ser Ala Ser Ser Gly Leu Arg Glu Ser Ser Gln Ser
        195                 200                 205

Ala Ser Thr Cys Thr Asp Gly Asn Asp Ser Gly Ala Gly Ser Asp Gln
    210                 215                 220

Leu Gly Glu Pro Gly Ala Gln Gln Arg Gln Arg Gly Lys His Arg Asp
225                 230                 235                 240

Arg Arg Asp Val Pro Ala Gln Gln Arg Pro Ala Val His Pro Ala Gly
                245                 250                 255

Pro Gly Pro Ala Asp Arg Val Gly Val Asp Pro Gly Arg His Arg Arg
            260                 265                 270

Ala Arg Gly Gln His Gln Pro Arg Asp Gly Ser Asp Arg Gln Ala Ser
        275                 280                 285

Arg Thr Val Ser Gly Val Pro Val Glu Ser Asn Val Leu Ser Ala Gly
    290                 295                 300

Ile Arg Cys Arg Thr Pro Thr Thr Arg Ala Val Ala Ile Cys Leu Ala
305                 310                 315                 320

Thr Leu Ala Ser Arg Gly Val Val Ala Pro Gln Pro Ala Gly Asp Val
                325                 330                 335

Ala Arg Ala Ala Ala Ala Gly Ser Pro Trp Pro Val Arg Ser Val Ala
            340                 345                 350

Arg Pro Val Ala Val Leu Arg Thr Gly Pro Pro Pro Arg Arg Pro Ser
```

-continued

```
        355                 360                 365

Asp Thr Gly Ser
    370


<210> SEQ ID NO 95
<211> LENGTH: 423
<212> TYPE: PRT
<213> ORGANISM: Mycobacterium vaccae

<400> SEQUENCE: 95

Ile Tyr Ser Thr Phe Ala Asp Arg Ala Tyr Pro Gly Gly Leu Thr Tyr
 1               5                  10                  15

Ser Gly His Pro Leu Ala Thr Ala Cys Ala Val Ala Thr Ile Asn Ala
            20                  25                  30

Met Glu Asp Glu Gly Met Val Ala Asn Ala Ala Arg Ile Gly Glu Gln
        35                  40                  45

Val Leu Gly Pro Gly Leu Arg Asp Leu Ala Ala Arg His Arg Ser Val
    50                  55                  60

Gly Glu Val Arg Gly Leu Gly Val Phe Trp Ala Gly Ser Asp Pro Glu
65                  70                  75                  80

Arg Ala Gly Leu Arg Val Glu Val Leu Gly Ala Gln Cys Arg Arg Arg
                85                  90                  95

Asp Val Val Gly Ala Gly Asp Ala Ala Ala Val Gly Val Leu Gly Pro
            100                 105                 110

Gln Arg Gln His Arg Ala Arg Ala Asp Gly Ser Ile Ser Ser Ala Leu
        115                 120                 125

Val Ala Ser Pro Pro Arg Ala Ala Ser Ser Ala Pro Ala Ser Ile Gly
    130                 135                 140

Leu Gly Pro Ser Gly Gln His Thr Ser Ile His Pro Arg Ser Ser Asn
145                 150                 155                 160

Gly Ser Pro Thr Val His Ile Ser Gln Ser Met Asn Ala Ala Ser Ser
                165                 170                 175

Gly Thr Ser Arg Arg Ser Ser Thr Leu Phe Arg Trp Gln Ser Pro Cys
            180                 185                 190

Met Ile Pro Gly Ser Ala Ser Ser Gly Leu Arg Glu Ser Ser Gln Ser
        195                 200                 205

Ala Ser Thr Cys Thr Asp Gly Asn Asp Ser Gly Ala Gly Ser Asp Gln
    210                 215                 220

Leu Gly Glu Pro Gly Ala Gln Gln Arg Gln Arg Gly Lys His Arg Asp
225                 230                 235                 240

Arg Arg Asp Val Pro Ala Gln Gln Arg Pro Ala Val His Pro Ala Gly
                245                 250                 255

Pro Gly Pro Ala Asp Arg Val Gly Val Asp Pro Gly Arg His Arg Arg
            260                 265                 270

Ala Arg Gly Gln His Gln Pro Arg Asp Gly Ser Asp Arg Gln Ala Ser
        275                 280                 285

Arg Thr Val Ser Gly Val Pro Val Glu Ser Asn Val Leu Ser Ala Gly
    290                 295                 300

Ile Arg Cys Arg Thr Pro Thr Thr Arg Ala Val Ala Ile Cys Leu Ala
305                 310                 315                 320

Thr Leu Ala Ser Arg Gly Val Val Ala Pro Gln Pro Ala Gly Asp Val
                325                 330                 335

Ala Arg Ala Ala Ala Ala Gly Ser Pro Trp Pro Val Arg Ser Val Ala
            340                 345                 350
```

-continued

```
Arg Pro Val Ala Val Leu Arg Thr Gly Pro Pro Pro Arg Arg Pro Ser
        355                 360                 365

Asp Thr Gly Ser Ile Thr Gln Val Gly Arg Pro Ala Val Leu Phe Ala
    370                 375                 380

Pro Glu Gln Arg Cys Arg Arg Arg Ala Asp Gln Arg Ser Cys Arg Gln
385                 390                 395                 400

Ile His Pro Gly Gly Gly Arg His Val Gln Ile Val Ala Ser Ala Arg
                405                 410                 415

Gly Thr Val Glu Ile Gly Ser
            420
```

<210> SEQ ID NO 96
<211> LENGTH: 471
<212> TYPE: PRT
<213> ORGANISM: Mycobacterium vaccae

<400> SEQUENCE: 96

```
Ile Tyr Ser Thr Phe Ala Asp Arg Ala Tyr Pro Gly Gly Leu Thr Tyr
 1               5                  10                  15

Ser Gly His Pro Leu Ala Thr Ala Cys Ala Val Ala Thr Ile Asn Ala
            20                  25                  30

Met Glu Asp Glu Gly Met Val Ala Asn Ala Ala Arg Ile Gly Glu Gln
        35                  40                  45

Val Leu Gly Pro Gly Leu Arg Asp Leu Ala Ala Arg His Arg Ser Val
    50                  55                  60

Gly Glu Val Arg Gly Leu Gly Val Phe Trp Ala Gly Ser Asp Pro Glu
65                  70                  75                  80

Arg Ala Gly Leu Arg Val Glu Val Leu Gly Ala Gln Cys Arg Arg Arg
                85                  90                  95

Asp Val Val Gly Ala Gly Asp Ala Ala Ala Val Gly Val Leu Gly Pro
            100                 105                 110

Gln Arg Gln His Arg Ala Arg Ala Asp Gly Ser Ile Ser Ser Ala Leu
        115                 120                 125

Val Ala Ser Pro Pro Arg Ala Ala Ser Ser Ala Pro Ala Ser Ile Gly
    130                 135                 140

Leu Gly Pro Ser Gly Gln His Thr Ser Ile His Pro Arg Ser Ser Asn
145                 150                 155                 160

Gly Ser Pro Thr Val His Ile Ser Gln Ser Met Asn Ala Ala Ser Ser
                165                 170                 175

Gly Thr Ser Arg Arg Ser Ser Thr Leu Phe Arg Trp Gln Ser Pro Cys
            180                 185                 190

Met Ile Pro Gly Ser Ala Ser Ser Gly Leu Arg Glu Ser Ser Gln Ser
        195                 200                 205

Ala Ser Thr Cys Thr Asp Gly Asn Asp Ser Gly Ala Gly Ser Asp Gln
    210                 215                 220

Leu Gly Glu Pro Gly Ala Gln Gln Arg Gln Arg Gly Lys His Arg Asp
225                 230                 235                 240

Arg Arg Asp Val Pro Ala Gln Gln Arg Pro Ala Val His Pro Ala Gly
                245                 250                 255

Pro Gly Pro Ala Asp Arg Val Gly Val Asp Pro Gly Arg His Arg Arg
            260                 265                 270

Ala Arg Gly Gln His Gln Pro Arg Asp Gly Ser Asp Arg Gln Ala Ser
        275                 280                 285

Arg Thr Val Ser Gly Val Pro Val Glu Ser Asn Val Leu Ser Ala Gly
    290                 295                 300
```

-continued

```
Ile Arg Cys Arg Thr Pro Thr Thr Arg Ala Val Ala Ile Cys Leu Ala
305                 310                 315                 320

Thr Leu Ala Ser Arg Gly Val Val Ala Pro Gln Pro Ala Gly Asp Val
                325                 330                 335

Ala Arg Ala Ala Ala Ala Gly Ser Pro Trp Pro Val Arg Ser Val Ala
            340                 345                 350

Arg Pro Val Ala Val Leu Arg Thr Gly Pro Pro Pro Arg Arg Pro Ser
        355                 360                 365

Asp Thr Gly Ser Ile Thr Gln Val Gly Arg Pro Ala Val Leu Phe Ala
    370                 375                 380

Pro Glu Gln Arg Cys Arg Arg Arg Ala Asp Gln Arg Ser Cys Arg Gln
385                 390                 395                 400

Ile His Pro Gly Gly Gly Arg His Val Gln Ile Val Ala Ser Ala Arg
                405                 410                 415

Gly Thr Val Glu Ile Gly Ser Ile Ala Arg Leu Cys Gly Lys Asp Glu
            420                 425                 430

Ala Val Ala Ala Leu His Tyr Val Ala Pro Val Gly Glu Lys Gln Asp
        435                 440                 445

Tyr Ile Asp Arg Ala Leu Arg Asn Ile Gly Pro Tyr Leu Pro Ala Glu
    450                 455                 460

Val Pro Ala Leu Val Gly Ser
465                 470


<210> SEQ ID NO 97
<211> LENGTH: 541
<212> TYPE: PRT
<213> ORGANISM: Mycobacterium vaccae

<400> SEQUENCE: 97

Ile Tyr Ser Thr Phe Ala Asp Arg Ala Tyr Pro Gly Gly Leu Thr Tyr
 1               5                  10                  15

Ser Gly His Pro Leu Ala Thr Ala Cys Ala Val Ala Thr Ile Asn Ala
            20                  25                  30

Met Glu Asp Glu Gly Met Val Ala Asn Ala Ala Arg Ile Gly Glu Gln
        35                  40                  45

Val Leu Gly Pro Gly Leu Arg Asp Leu Ala Ala Arg His Arg Ser Val
    50                  55                  60

Gly Glu Val Arg Gly Leu Gly Val Phe Trp Ala Gly Ser Asp Pro Glu
65                  70                  75                  80

Arg Ala Gly Leu Arg Val Glu Val Leu Gly Ala Gln Cys Arg Arg Arg
                85                  90                  95

Asp Val Val Gly Ala Gly Asp Ala Ala Ala Val Gly Val Leu Gly Pro
            100                 105                 110

Gln Arg Gln His Arg Ala Arg Ala Asp Gly Ser Ile Ser Ser Ala Leu
        115                 120                 125

Val Ala Ser Pro Pro Arg Ala Ala Ser Ser Ala Pro Ala Ser Ile Gly
    130                 135                 140

Leu Gly Pro Ser Gly Gln His Thr Ser Ile His Pro Arg Ser Ser Asn
145                 150                 155                 160

Gly Ser Pro Thr Val His Ile Ser Gln Ser Met Asn Ala Ala Ser Ser
                165                 170                 175

Gly Thr Ser Arg Arg Ser Ser Thr Leu Phe Arg Trp Gln Ser Pro Cys
            180                 185                 190

Met Ile Pro Gly Ser Ala Ser Ser Gly Leu Arg Glu Ser Ser Gln Ser
```

-continued

```
        195                 200                 205

Ala Ser Thr Cys Thr Asp Gly Asn Asp Ser Gly Ala Gly Ser Asp Gln
    210                 215                 220

Leu Gly Glu Pro Gly Ala Gln Gln Arg Gln Arg Gly Lys His Arg Asp
225                 230                 235                 240

Arg Arg Asp Val Pro Ala Gln Gln Arg Pro Ala Val His Pro Ala Gly
                245                 250                 255

Pro Gly Pro Ala Asp Arg Val Gly Val Asp Pro Gly Arg His Arg Arg
            260                 265                 270

Ala Arg Gly Gln His Gln Pro Arg Asp Gly Ser Asp Arg Gln Ala Ser
        275                 280                 285

Arg Thr Val Ser Gly Val Pro Val Glu Ser Asn Val Leu Ser Ala Gly
    290                 295                 300

Ile Arg Cys Arg Thr Pro Thr Thr Arg Ala Val Ala Ile Cys Leu Ala
305                 310                 315                 320

Thr Leu Ala Ser Arg Gly Val Val Ala Pro Gln Pro Ala Gly Asp Val
                325                 330                 335

Ala Arg Ala Ala Ala Ala Gly Ser Pro Trp Pro Val Arg Ser Val Ala
            340                 345                 350

Arg Pro Val Ala Val Leu Arg Thr Gly Pro Pro Pro Arg Arg Pro Ser
        355                 360                 365

Asp Thr Gly Ser Ile Thr Gln Val Gly Arg Pro Ala Val Leu Phe Ala
    370                 375                 380

Pro Glu Gln Arg Cys Arg Arg Arg Ala Asp Gln Arg Ser Cys Arg Gln
385                 390                 395                 400

Ile His Pro Gly Gly Gly Arg His Val Gln Ile Val Ala Ser Ala Arg
                405                 410                 415

Gly Thr Val Glu Ile Gly Ser Ile Ala Arg Leu Cys Gly Lys Asp Glu
            420                 425                 430

Ala Val Ala Ala Leu His Tyr Val Ala Pro Val Gly Glu Lys Gln Asp
        435                 440                 445

Tyr Ile Asp Arg Ala Leu Arg Asn Ile Gly Pro Tyr Leu Pro Ala Glu
    450                 455                 460

Val Pro Ala Leu Val Gly Ser Ile Ala Ala Thr Gly Pro Val Pro Gly
465                 470                 475                 480

Thr Ala Trp Ile Val Arg Gln Tyr Pro Lys Leu Leu Arg Ala Lys Ala
                485                 490                 495

Asn Trp Glu Asp Thr Trp Thr Phe Pro Ser Ile Glu Glu Lys His Arg
            500                 505                 510

Pro Arg Gly Ser Val Ala Gly Pro Val Phe Arg Val Asn Leu Gly Arg
        515                 520                 525

Ala Ile Pro Ser Arg Ala Ala Arg Ala Ala Glu Ile His
    530                 535                 540
```

<210> SEQ ID NO 98
<211> LENGTH: 33
<212> TYPE: DNA
<213> ORGANISM: Artificial Sequence
<220> FEATURE:
<223> OTHER INFORMATION: Artificial sequence

<400> SEQUENCE: 98
gtgtgtctcg agctacgccc agaagacgcc gag 33

<210> SEQ ID NO 99

-continued

<211> LENGTH: 33
<212> TYPE: DNA
<213> ORGANISM: Artificial Sequence
<220> FEATURE:
<223> OTHER INFORMATION: Artificial Sequence

<400> SEQUENCE: 99
gtgtgtctcg agctaatccg cccgggcacg gtg 33

<210> SEQ ID NO 100
<211> LENGTH: 33
<212> TYPE: DNA
<213> ORGANISM: Artificial Sequence
<220> FEATURE:
<223> OTHER INFORMATION: Artificial Sequence

<400> SEQUENCE: 100
gtgtgtctcg agtcacgcgc ccgagtcgtt ccc 33

<210> SEQ ID NO 101
<211> LENGTH: 33
<212> TYPE: DNA
<213> ORGANISM: Artificial Sequence
<220> FEATURE:
<223> OTHER INFORMATION: Artificial Sequence

<400> SEQUENCE: 101
gtgtgtctcg agtcaatccc gtggctgatg ctg 33

<210> SEQ ID NO 102
<211> LENGTH: 33
<212> TYPE: DNA
<213> ORGANISM: Artificial Sequence
<220> FEATURE:
<223> OTHER INFORMATION: Artificial Sequence

<400> SEQUENCE: 102
gtgtgtctcg agtcacgtat cggacggacg acg 33

<210> SEQ ID NO 103
<211> LENGTH: 33
<212> TYPE: DNA
<213> ORGANISM: Artificial Sequence
<220> FEATURE:
<223> OTHER INFORMATION: Artificial Sequence

<400> SEQUENCE: 103
gtgtgtctcg agtcagatct ccaccgtgcc gcg 33

<210> SEQ ID NO 104
<211> LENGTH: 33
<212> TYPE: DNA
<213> ORGANISM: Artificial Sequence
<220> FEATURE:
<223> OTHER INFORMATION: Artificial Sequence

<400> SEQUENCE: 104
gtgtgtctcg agtcagacga gagcgggaac ctc 33

<210> SEQ ID NO 105
<211> LENGTH: 33
<212> TYPE: DNA
<213> ORGANISM: Artificial Sequence
<220> FEATURE:
<223> OTHER INFORMATION: Artificial Sequence

<400> SEQUENCE: 105

-continued gtgtgtctcg agtcagtgga tttccgctgc gcg 33

<210> SEQ ID NO 106
<211> LENGTH: 33
<212> TYPE: DNA
<213> ORGANISM: Artificial Sequence
<220> FEATURE:
<223> OTHER INFORMATION: Artificial Sequence

<400> SEQUENCE: 106
gtgtgttcta gactacgcgc ccgagtcgtt ccc 33

<210> SEQ ID NO 107
<211> LENGTH: 33
<212> TYPE: DNA
<213> ORGANISM: Artificial Sequence
<220> FEATURE:
<223> OTHER INFORMATION: Artificial Sequence

<400> SEQUENCE: 107
gtgtgttcta gactaatccc gtggctgatg ctg 33

<210> SEQ ID NO 108
<211> LENGTH: 33
<212> TYPE: DNA
<213> ORGANISM: Artificial Sequence
<220> FEATURE:
<223> OTHER INFORMATION: Artificial Sequence

<400> SEQUENCE: 108
gtgtgttcta gactacgtat cggacggacg acg 33

<210> SEQ ID NO 109
<211> LENGTH: 39
<212> TYPE: DNA
<213> ORGANISM: Artificial Sequence
<220> FEATURE:
<223> OTHER INFORMATION: Artificial Sequence

<400> SEQUENCE: 109
gtgtgttcta gactaagatc cgatctccac cgtgccgcg 39

<210> SEQ ID NO 110
<211> LENGTH: 33
<212> TYPE: DNA
<213> ORGANISM: Artificial Sequence
<220> FEATURE:
<223> OTHER INFORMATION: Artificial Sequence

<400> SEQUENCE: 110
gtgtgttcta gatcagacga gagcgggaac ctc 33

<210> SEQ ID NO 111
<211> LENGTH: 33
<212> TYPE: DNA
<213> ORGANISM: Artificial Sequence
<220> FEATURE:
<223> OTHER INFORMATION: Artificial Sequence

<400> SEQUENCE: 111
gtgtgttcta gatcagtgga tttccgctgc gcg 33

<210> SEQ ID NO 112
<211> LENGTH: 32
<212> TYPE: DNA
<213> ORGANISM: Mycobacterium vaccae -continued

```
<400> SEQUENCE: 112

acacacgaat tcgcatctac tcgaccttcg cc                                    32


<210> SEQ ID NO 113
<211> LENGTH: 30
<212> TYPE: DNA
<213> ORGANISM: Artificial Sequence
<220> FEATURE:
<223> OTHER INFORMATION: Artificial Sequence

<400> SEQUENCE: 113

acacacggat ccatctactc gaccttcgcc                                       30


<210> SEQ ID NO 114
<211> LENGTH: 29
<212> TYPE: DNA
<213> ORGANISM: Artificial Sequence
<220> FEATURE:
<223> OTHER INFORMATION: Artificial Sequence

<400> SEQUENCE: 114

acacacgatc catctactcg accttcgcc                                        29
```